(12) United States Patent
Wach et al.

(10) Patent No.: US 6,174,424 B1
(45) Date of Patent: Jan. 16, 2001

(54) COUPLERS FOR OPTICAL FIBERS

(75) Inventors: Michael Leonard Wach, Byron; Eric Todd Marple, Warner Robins, both of GA (US)

(73) Assignee: Cirrex Corp., Atlanta, GA (US)

( * ) Notice: Under 35 U.S.C. 154(b), the term of this patent shall be extended for 0 days.

(21) Appl. No.: 09/267,231

(22) Filed: Mar. 12, 1999

Related U.S. Application Data

(63) Continuation of application No. 08/819,979, filed on Mar. 13, 1997, now Pat. No. 5,953,477, which is a continuation of application No. 08/561,484, filed on Nov. 20, 1995
(60) Provisional application No. 60/013,341, filed on Mar. 13, 1996, provisional application No. 60/036,504, filed on Jan. 28, 1997, and provisional application No. 60/038,395, filed on Feb. 14, 1997.

(51) Int. Cl.[7] .............................. C25D 1/02; C25D 1/00
(52) U.S. Cl. ................................. 205/73; 205/79
(58) Field of Search ........................ 427/163.1; 205/73

(56) References Cited

U.S. PATENT DOCUMENTS

| | | | |
|---|---|---|---|
| 3,187,639 | * 6/1965 | Kelly et al. | 92/47 |
| 3,796,905 | 3/1974 | Tomii et al. | 313/92 |
| 3,874,783 | 4/1975 | Cole | 350/96 |
| 3,906,241 | 9/1975 | Thompson | 250/574 |
| 3,910,677 | 10/1975 | Becker et al. | 350/96 |
| 4,191,446 | 3/1980 | Arditty et al. | 350/96 |
| 4,380,365 | 4/1983 | Gross | 350/96.18 |
| 4,449,535 | 5/1984 | Renault | 128/634 |
| 4,573,761 | 3/1986 | McLachlan et al. | 350/96.24 |
| 4,615,581 | 10/1986 | Morimoto | 350/96.21 |
| 4,654,532 | 3/1987 | Hirschfeld | 250/458.1 |
| 4,707,134 | 11/1987 | McLachlan et al. | 356/342 |
| 4,733,933 | * 3/1988 | Pikulski | 350/96.2 |

(List continued on next page.)

FOREIGN PATENT DOCUMENTS

| | | |
|---|---|---|
| 0185782 | 7/1986 | (EP) . |
| 0210869 | 2/1987 | (EP) . |
| 0286419 | 10/1988 | (EP) . |

OTHER PUBLICATIONS

Bojarski A., "Fiber Optic Particle Concentration Sensor", *SPIE vol. 566 Fiber Optic and Laser Sensors III*, 1985, pp. 122–125. Month Not Available.

Krohn D., "Intensity Modulated Fiber Optic Sensors Overview", *SPIE vol. 718 Fiber Optic and Laser Sensors IV*, 1986, pp. 2–11. Month Not Available.

McCann, B., "Specialty Optical Fibers Resolve Challenging Application Problems", *Lightwave*, Nov. 1994, pp. 48, 51–52.

Tan, W. et al., "Submicrometer Intracellular Chemical Optical Fiber Sensors", *Science*, vol. 258, Oct. 30, 1992, pp. 778–781.

Russo, V. et al. "Microlens—Ended Fibers: A New Fabrication Technique", Insituto di Ricerca sulle Onde Elettromagnetiche, Firenze, Italy, pp. 21–27. date not available.

Ku, R. T. "Progress in Efficient/Reliable Semiconductor Laser–to–Single–Mode Fiber Coupler Development", pp. 4–6. 1984. Month not available.

(List continued on next page.)

*Primary Examiner*—Kathryn Gorgos
*Assistant Examiner*—Erica Smith-Hicks
(74) *Attorney, Agent, or Firm*—King & Spalding

(57) ABSTRACT

Manufacturing couplers for optical fibers having thin precision dimensions for precision alignment and low-loss coupling of optical fiber segments are disclosed. The couplers can be formed by depositing material on a precision mandrel, removing the mandrel, and then further machining the couplers if necessary. Design variations include simple sleeves and sleeves having ends that are flanged outward so that the ends taper to the correct diameter.

20 Claims, 30 Drawing Sheets

U.S. PATENT DOCUMENTS

| | | | |
|---|---|---|---|
| 4,812,003 | 3/1989 | Dambach et al. | 350/96.18 |
| 4,816,670 | 3/1989 | Kitamura et al. | 250/227 |
| 4,914,284 | 4/1990 | Halldorsson et al. | 250/206.2 |
| 4,919,891 | 4/1990 | Yafuso et al. | 422/58 |
| 4,979,797 | 12/1990 | Nemeth | 350/96.29 |
| 4,995,691 | 2/1991 | Purcell, Jr. | 350/96.15 |
| 5,011,254 | 4/1991 | Edwards et al. | 350/96.18 |
| 5,011,279 | 4/1991 | Auweter et al. | 356/28.5 |
| 5,037,180 | 8/1991 | Stone | 385/123 |
| 5,074,632 | 12/1991 | Potter | 385/31 |
| 5,112,127 | 5/1992 | Carrabba et al. | 356/301 |
| 5,146,917 | 9/1992 | Wagnieres et al. | 128/397 |
| 5,166,756 | 11/1992 | McGee et al. | 356/446 |
| 5,196,005 | 3/1993 | Doiron et al. | 606/7 |
| 5,253,312 | 10/1993 | Payne et al. | 385/31 |
| 5,263,952 | 11/1993 | Grace et al. | 606/15 |
| 5,269,777 | 12/1993 | Doiron et al. | 606/7 |
| 5,308,656 * | 5/1994 | Emmons | 427/282 |
| 5,330,465 | 7/1994 | Doiron et al. | 606/7 |
| 5,402,508 | 3/1995 | O'Rourke et al. | 385/31 |
| 5,404,218 | 4/1995 | Nave et al. | 356/301 |
| 5,421,928 | 6/1995 | Knecht et al. | 156/153 |
| 5,432,880 | 7/1995 | Diner | 385/85 |
| 5,486,378 * | 1/1996 | Oestreich et al. | 427/163.2 |
| 5,529,680 * | 6/1996 | Kitada et al. | 205/67 |
| 5,636,307 * | 6/1997 | Cowen et al. | 385/102 |
| 5,710,626 | 1/1998 | O'Rourke et al. | 356/301 |
| 5,764,840 | 6/1998 | Wach | 385/123 |
| 5,939,137 * | 8/1999 | Kuck et al. | 427/163.2 |
| 5,974,837 * | 11/1999 | Abbott, III et al. | 65/432 |

OTHER PUBLICATIONS

Shintaku, Toshihiro, et al. "Connection Mechanism of Physical–Contact Optical Fiber Connectors with Spherical Convex Polished Ends", *Applied Optics*, vol. 30, No. 36, pp. 5260–5265, Dec. 1991.

Shintaku, Toshihiro, et al. "Highly Stable Physical–Contact Optical Fiber Connectors with Spherical Convex Ends", *Journal of Lightwave Technology*, vol. 11, No. 2, pp. 241–248, Feb. 1993.

Kanda, Torahiko et al. "A New Spherical Mirror–Finish Surface Machining Technology for Optical Fiber Connector", *NEC Res. & Develop*, vol. 36, No. 2, pp. 271–279, Apr. 1995.

Russo V. and Margheri, G. "Lens Ended Fiber–Fiber Connections for Power Laser Applications", *SPIE*, vol. 701 ECOOSA, pp. 220–225, 1986. month Not Available.

* cited by examiner

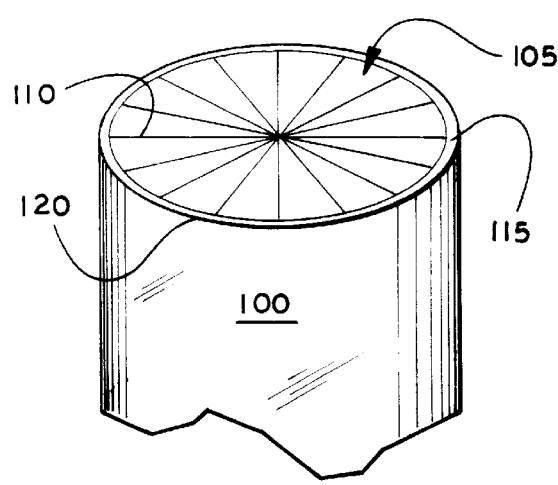
Fig_1
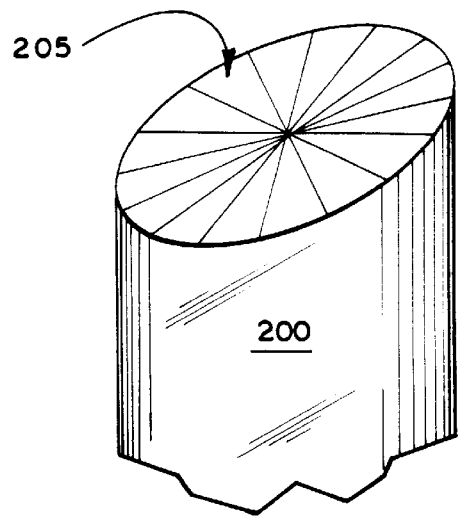
Fig_2
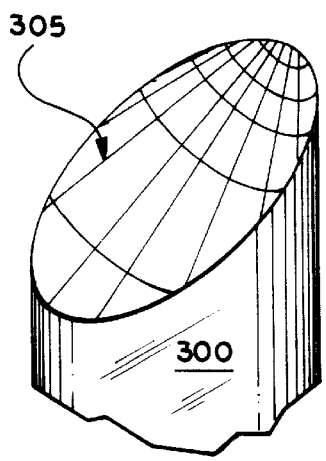
Fig_3A
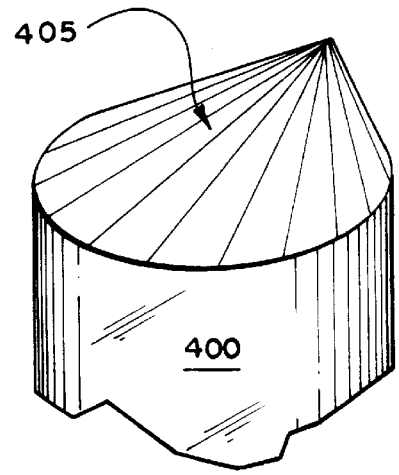
Fig_4
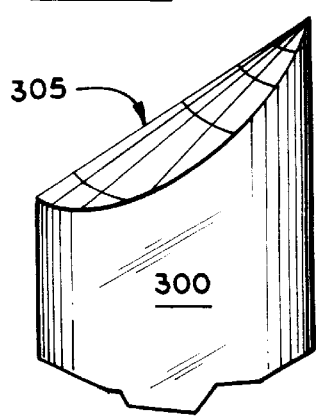
Fig_3B

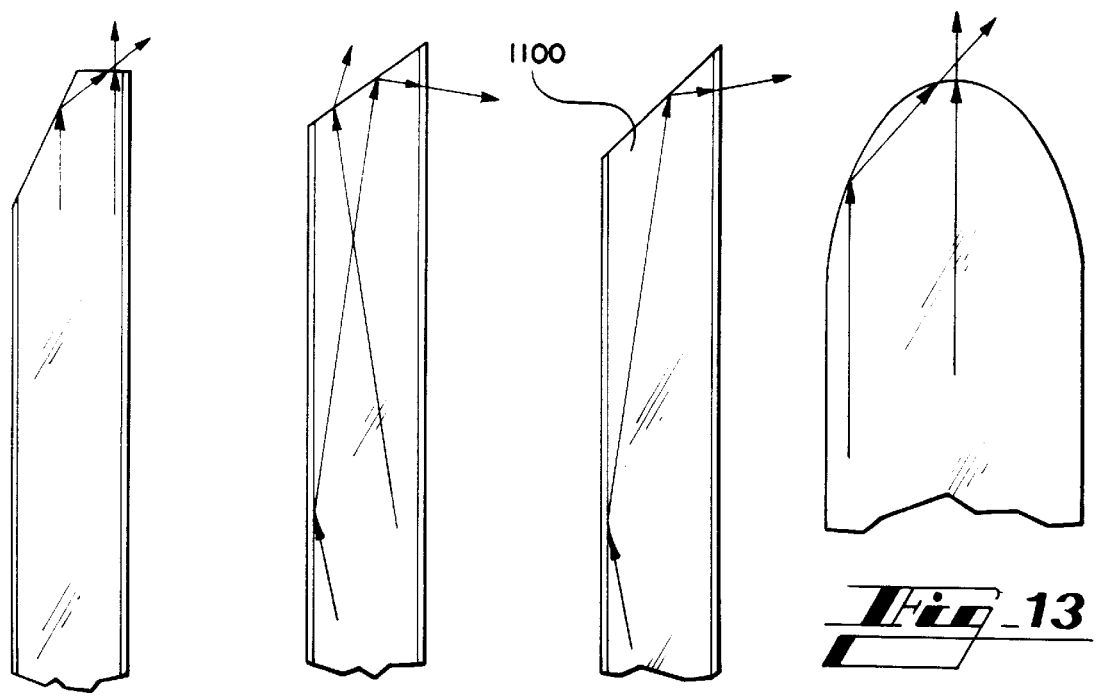
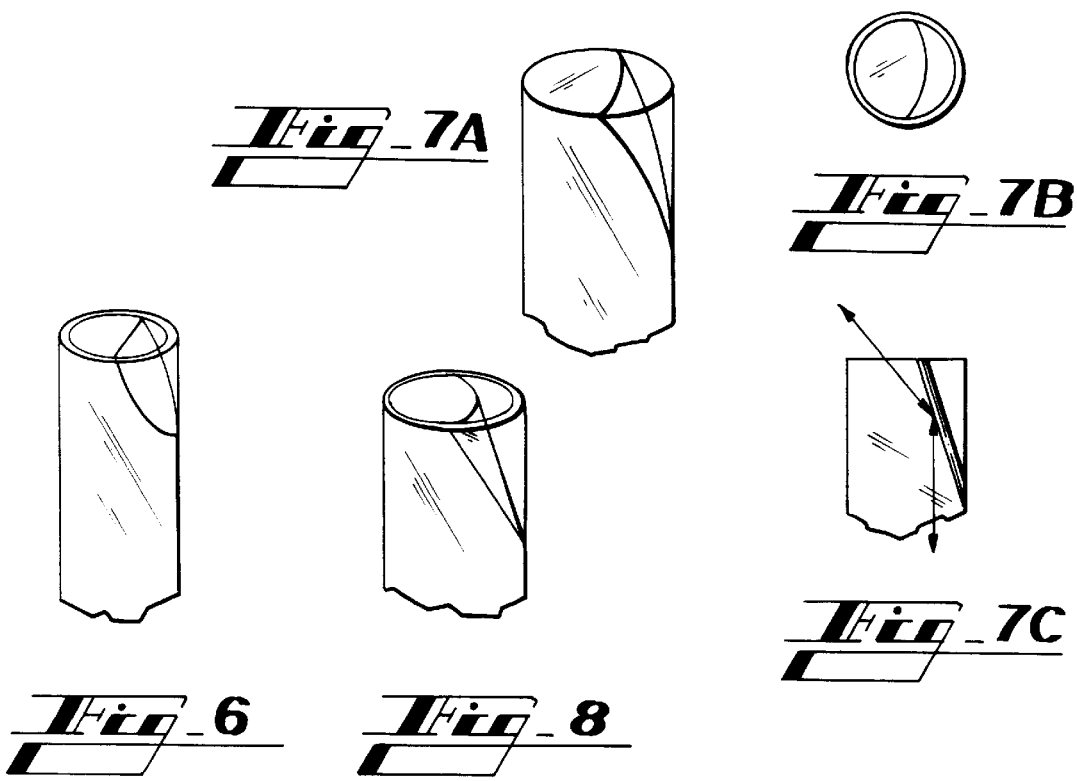

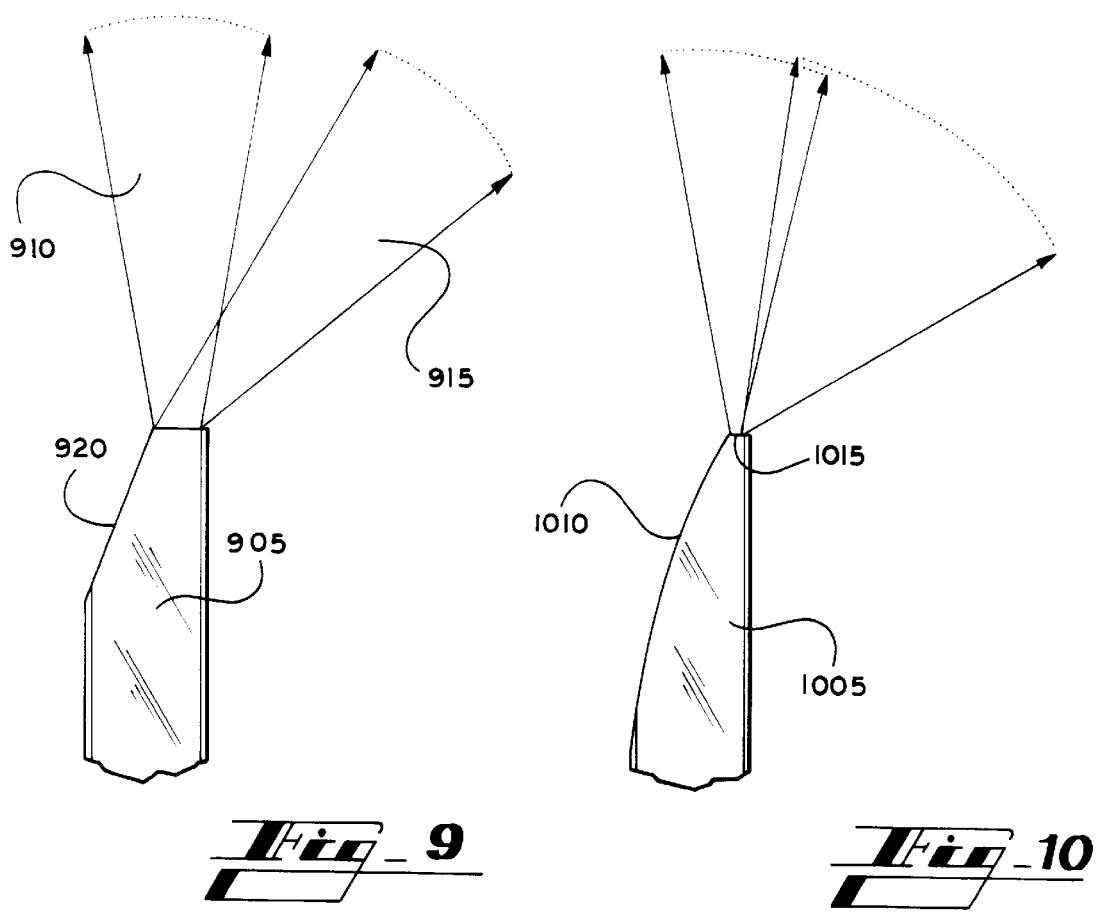
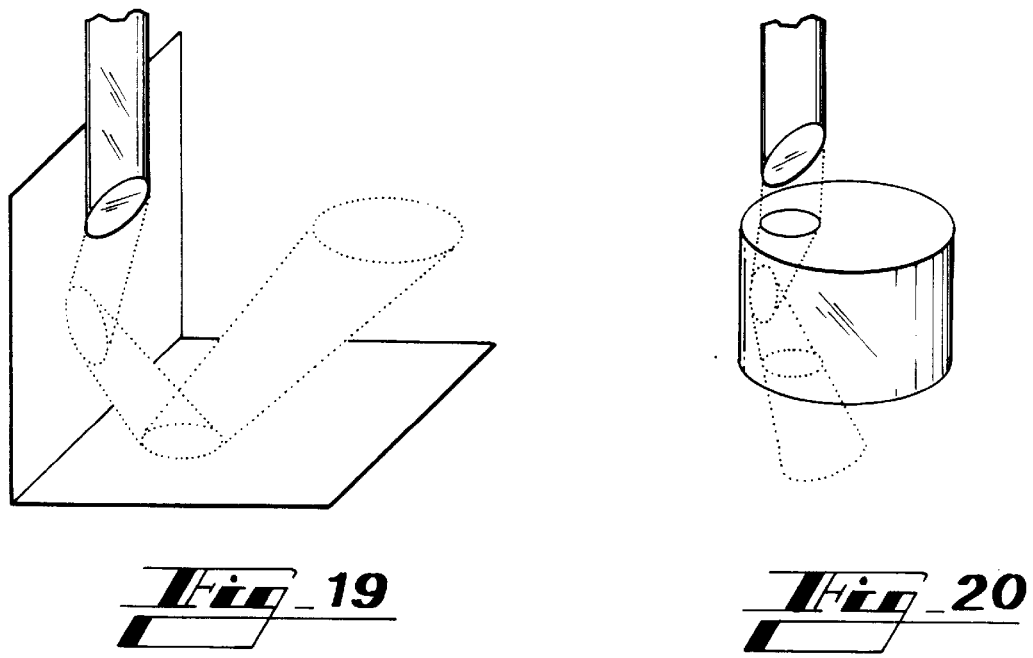

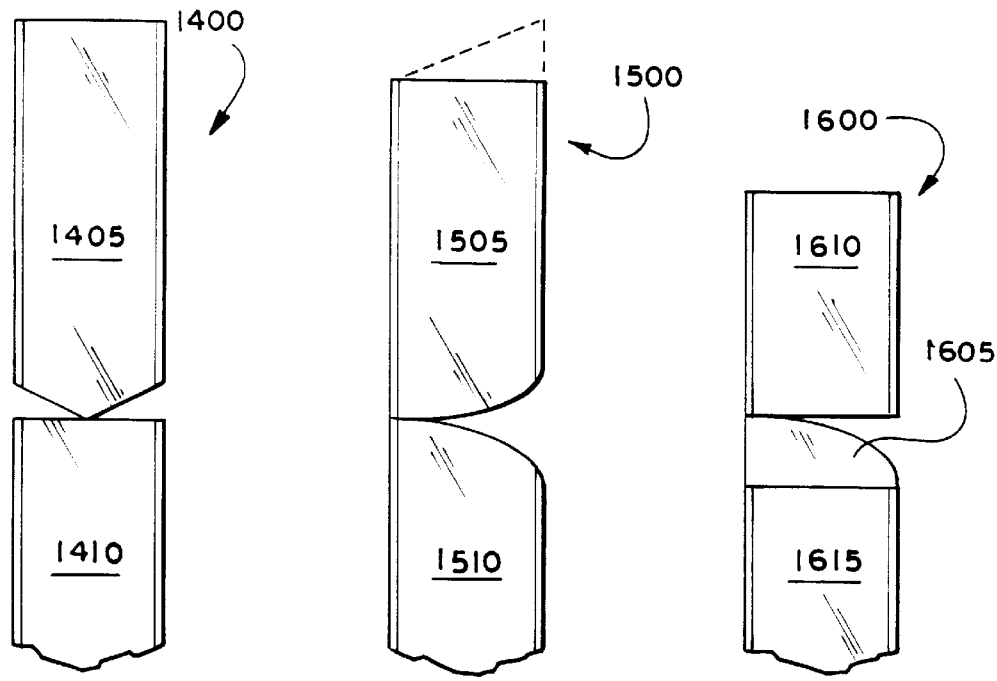
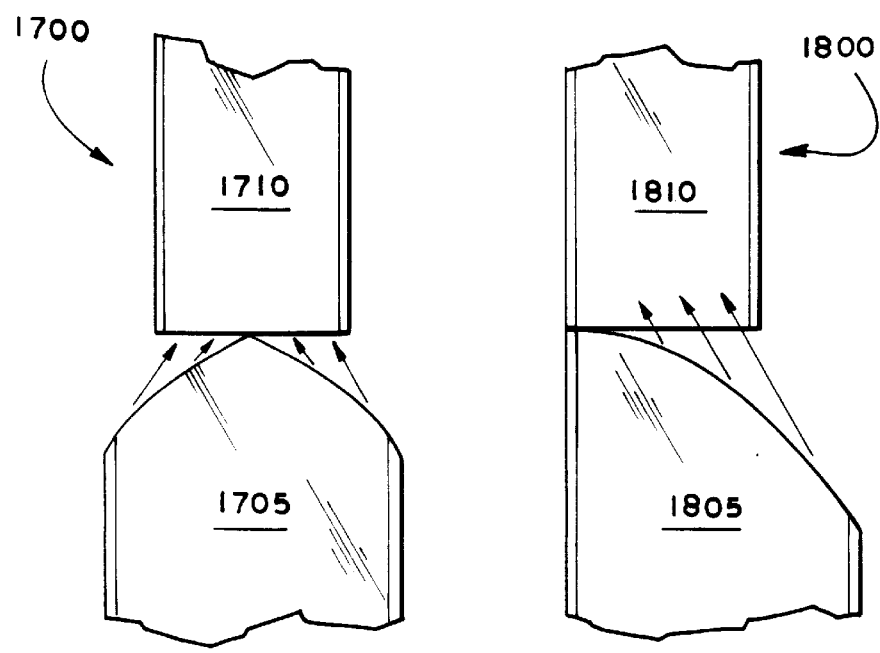

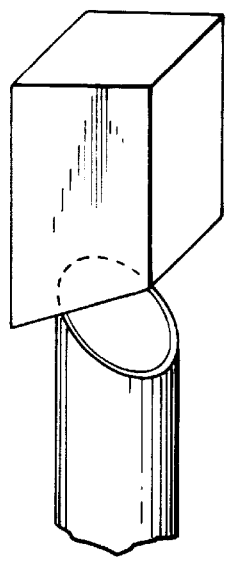
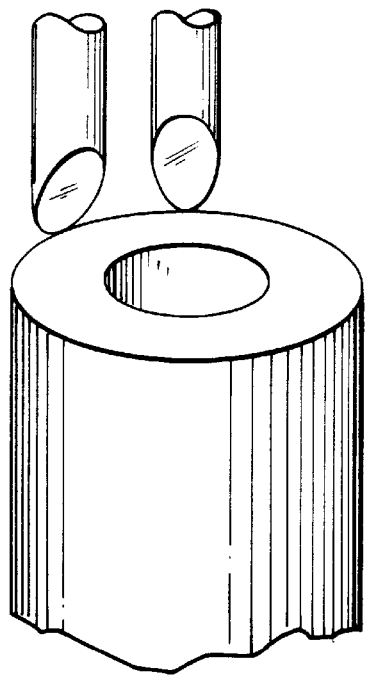
Fig_21
Fig_22
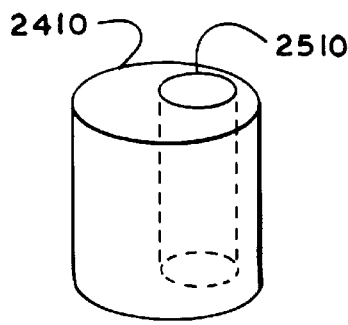
Fig_25
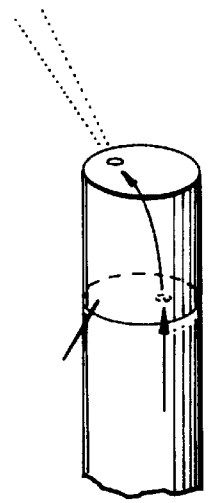
Fig_26
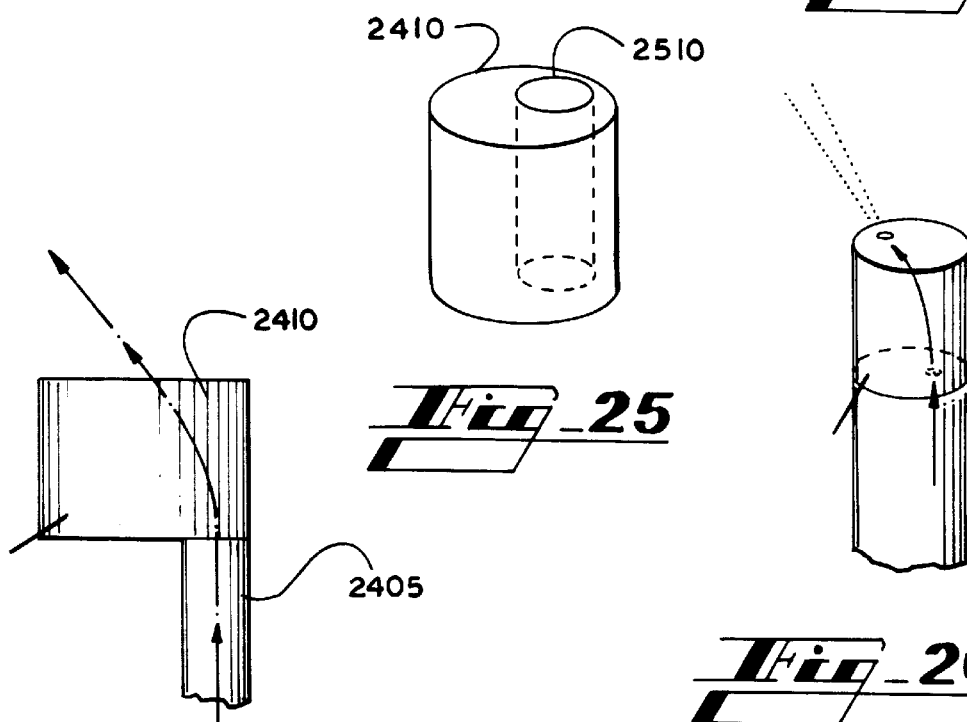
Fig_24

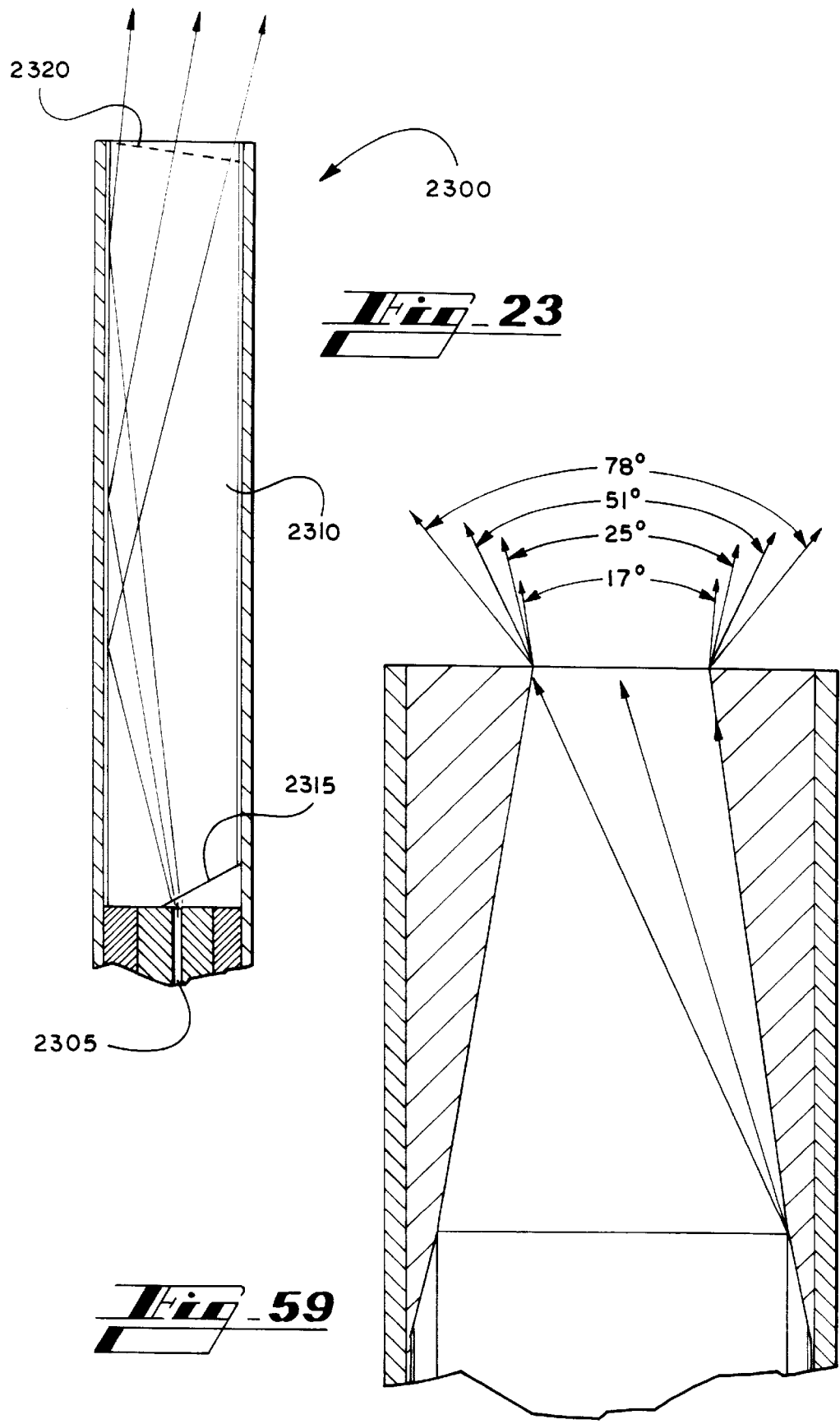

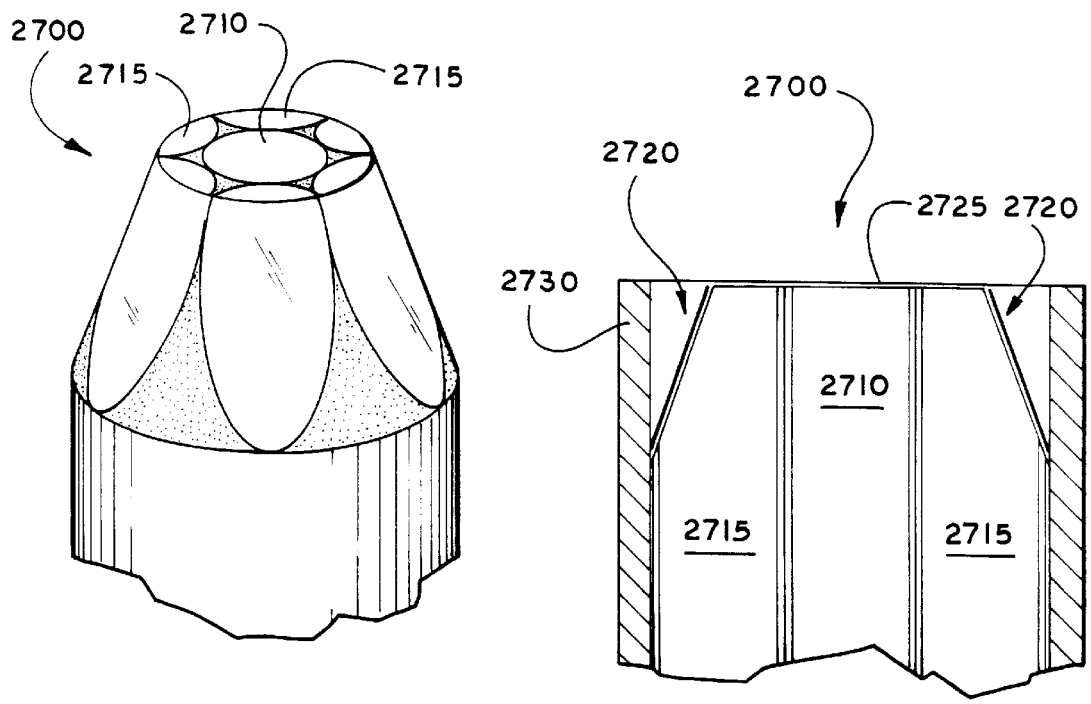
_Fig_ 27A
_Fig_ 27B
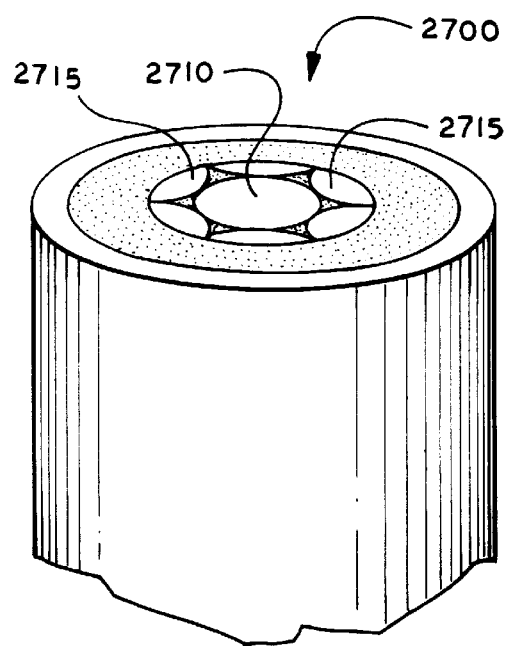
_Fig_ 27C

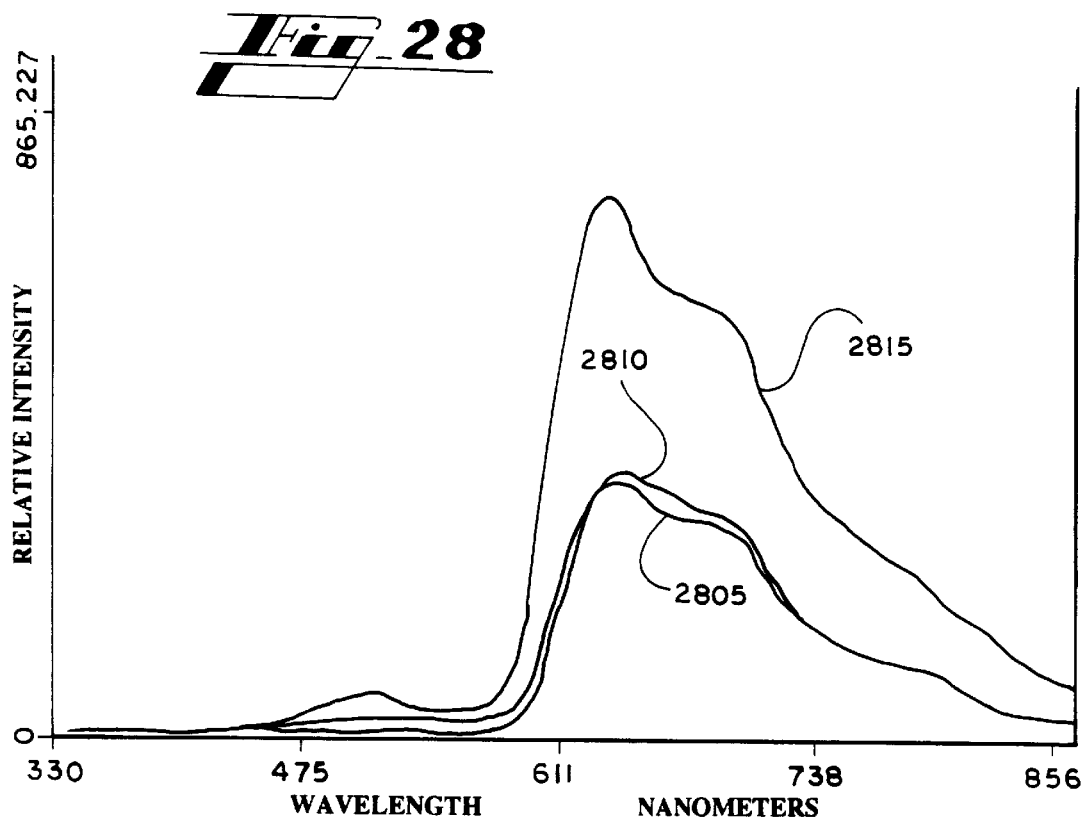
Fig_28
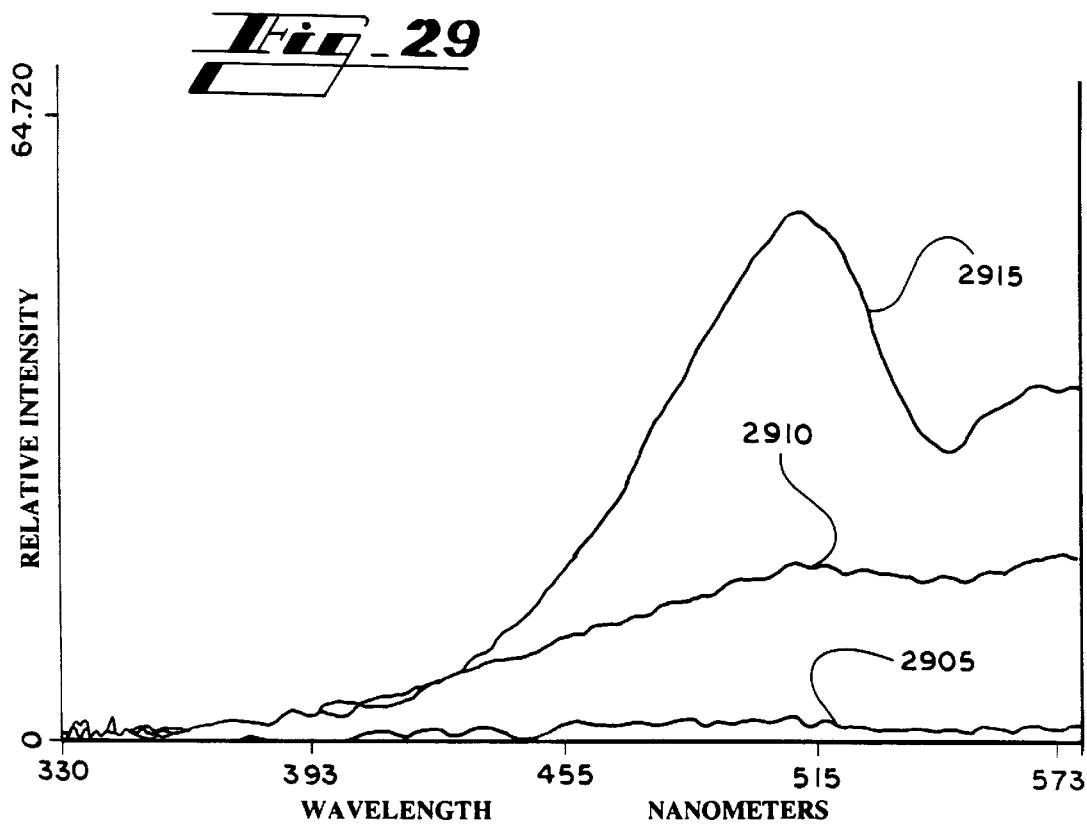
Fig_29

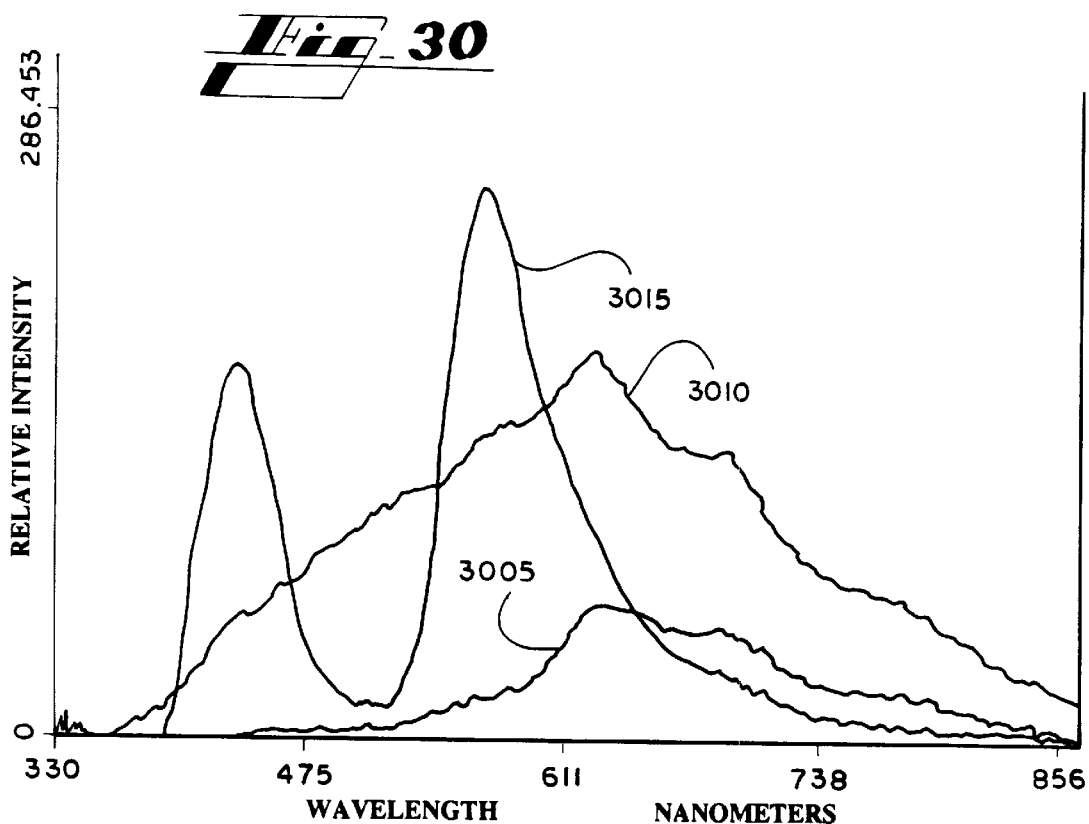
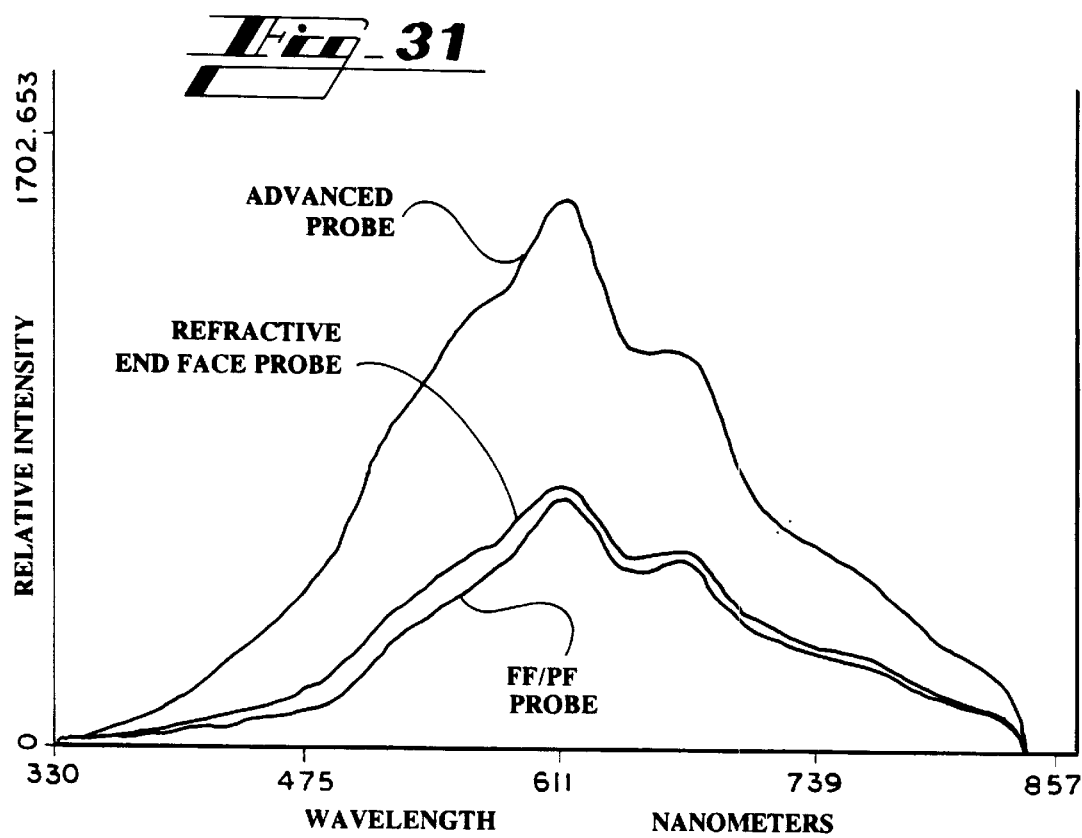

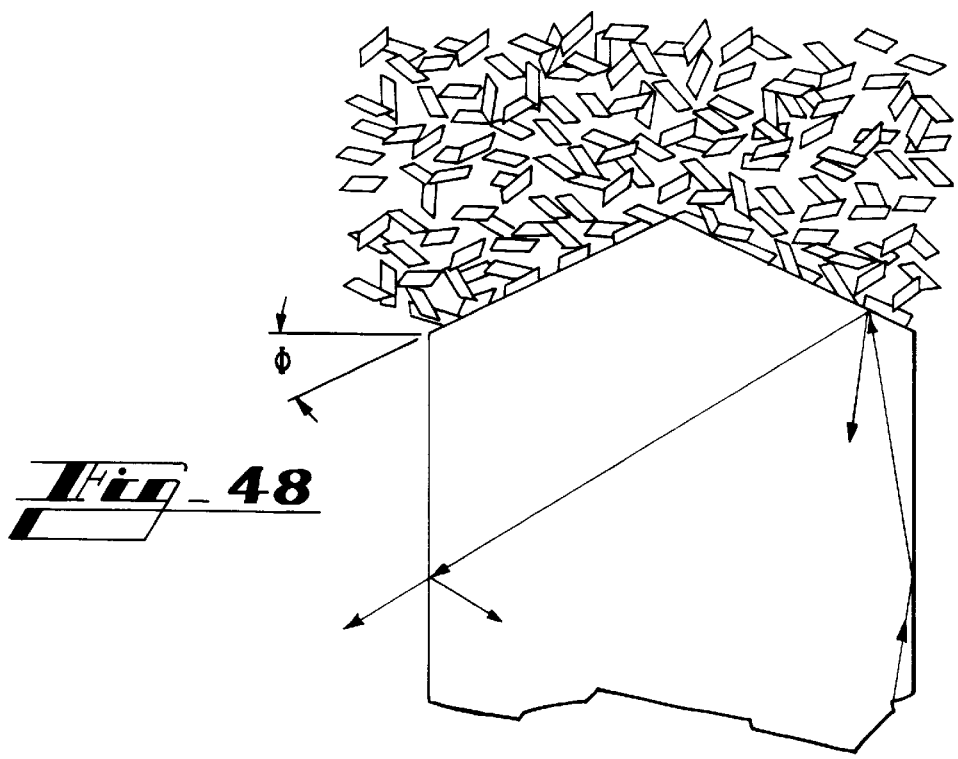
Fig_48
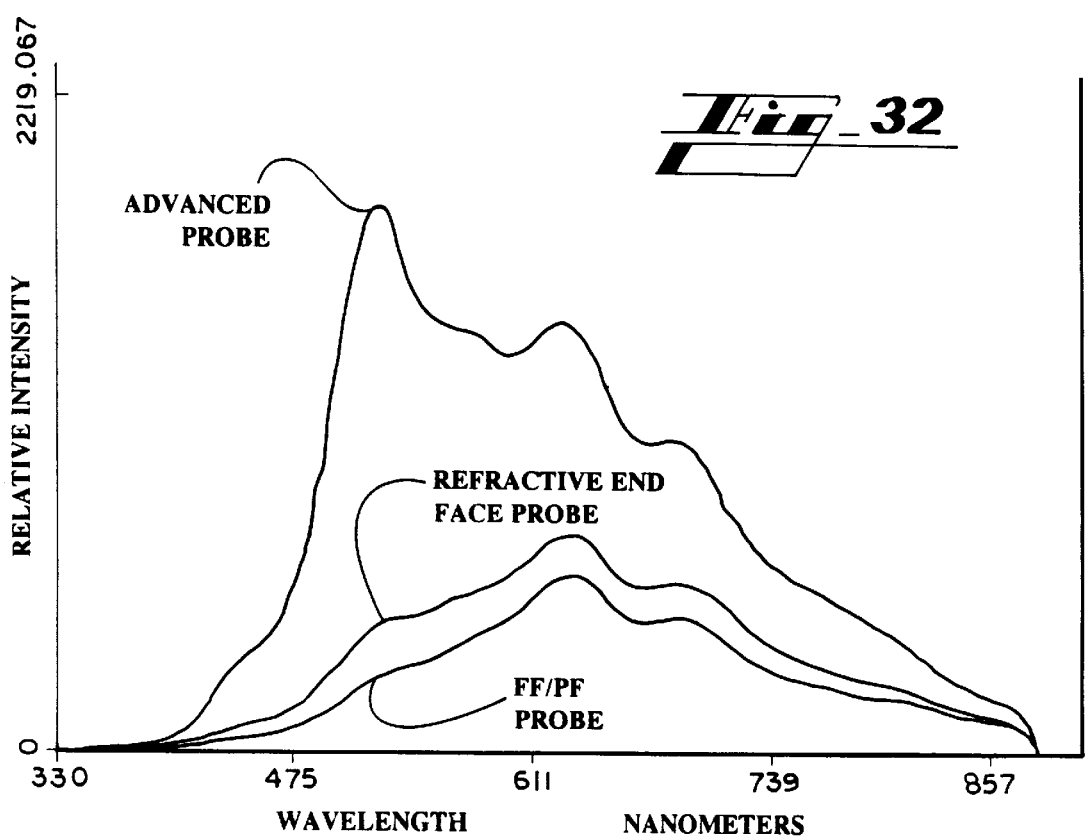
Fig_32

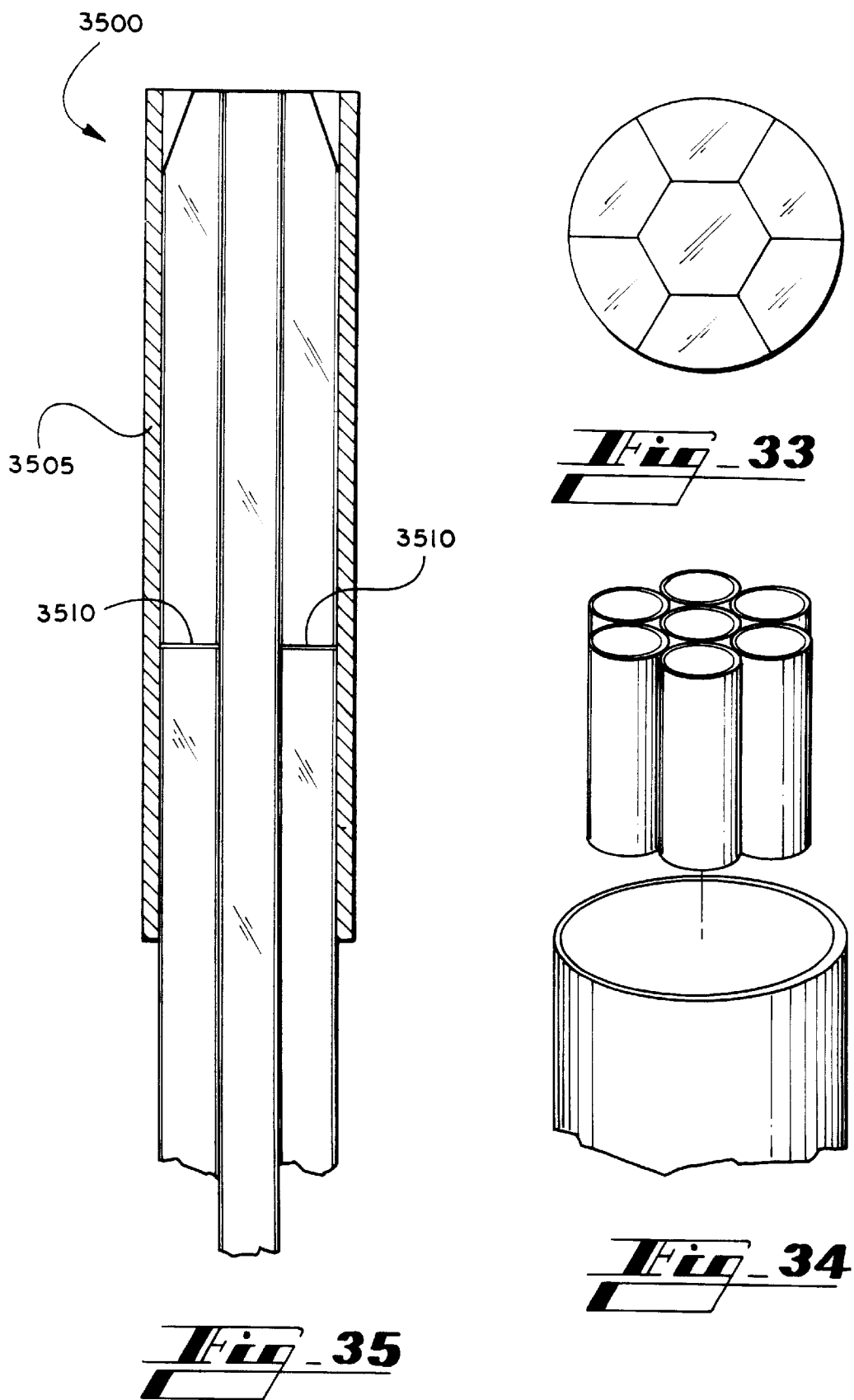

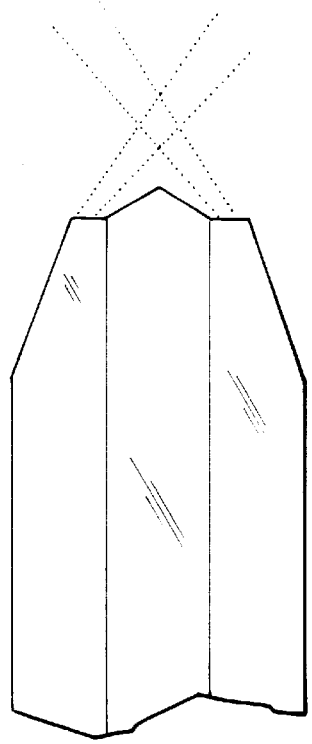
Fig_36
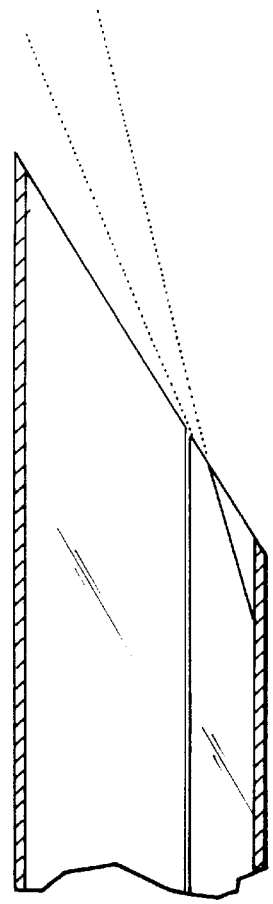
Fig_37A
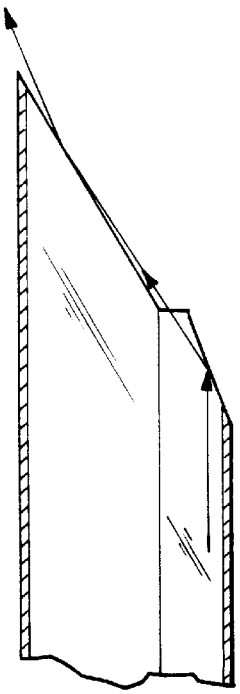
Fig_37B

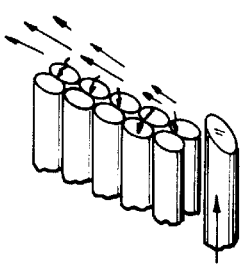
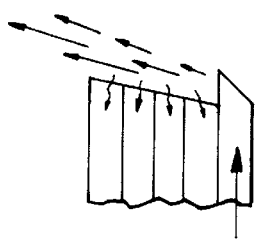
*Fig_38B*  *Fig_38D*
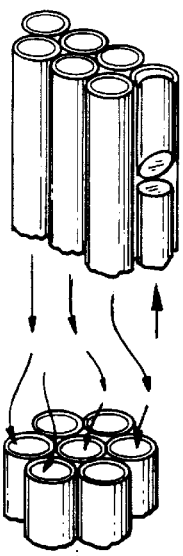
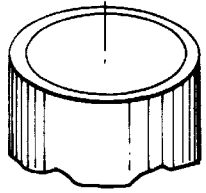
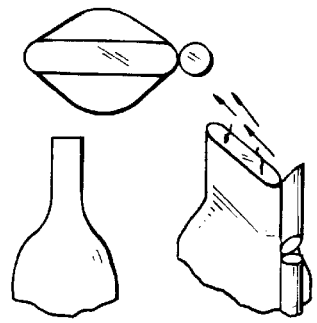
*Fig_38C*
*Fig_38E*
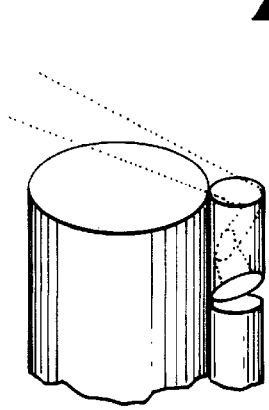
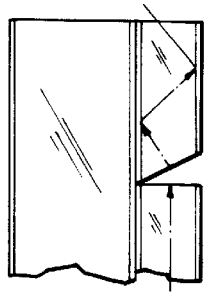
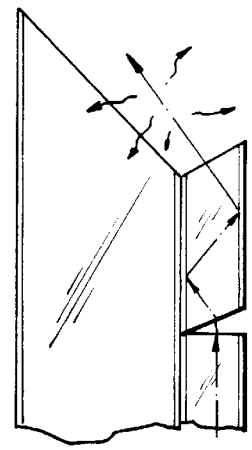
*Fig_38A*
*Fig_38H*  *Fig_38F*  *Fig_38G*

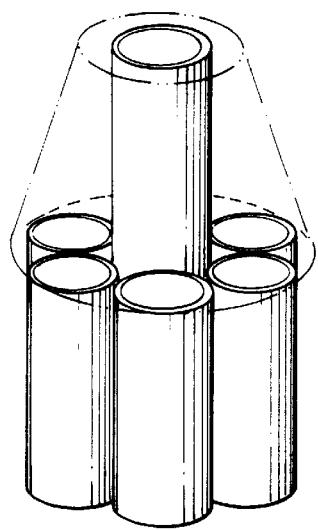
Fig_39A
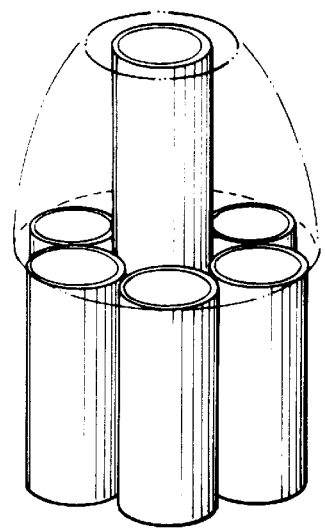
Fig_39B
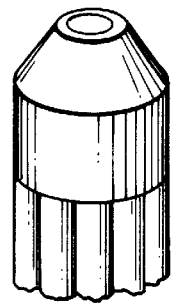
Fig_40B
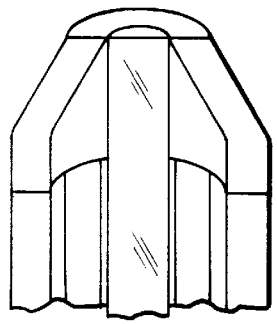
Fig_40A
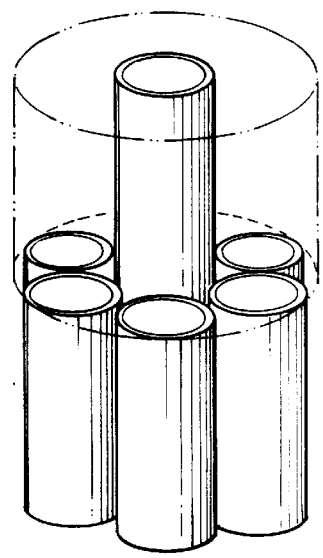
Fig_52A
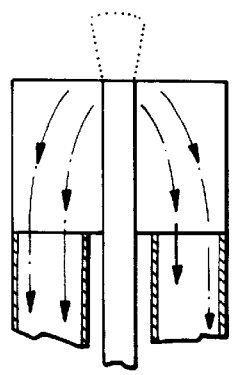
Fig_52B

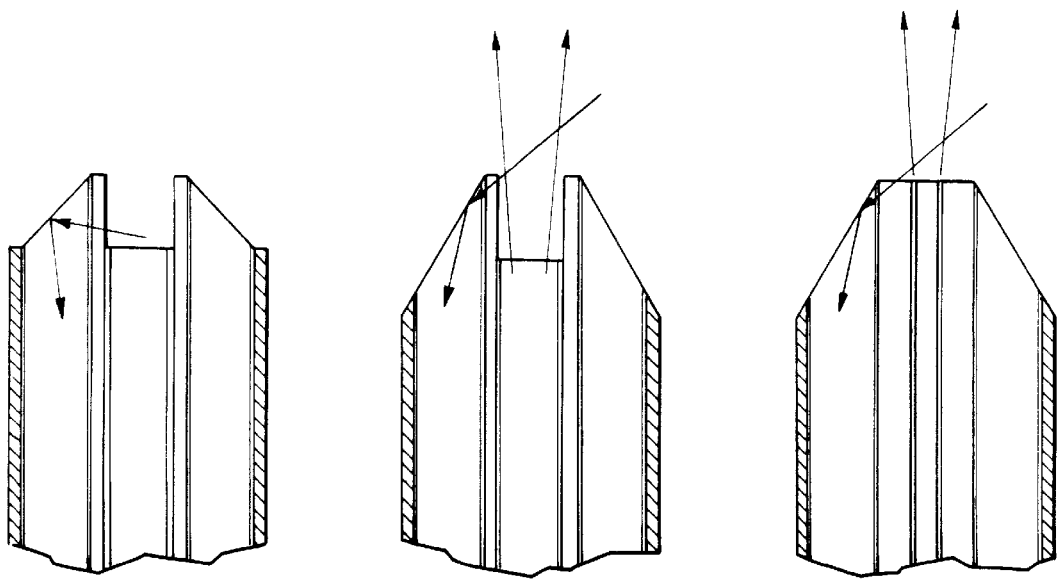
_Fig_41   _Fig_43   _Fig_44
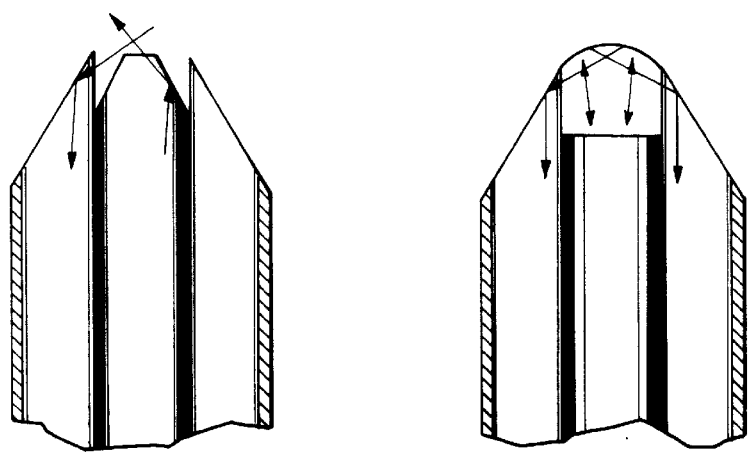
_Fig_45   _Fig_46

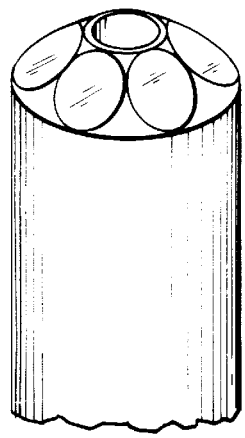
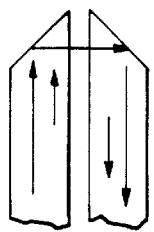
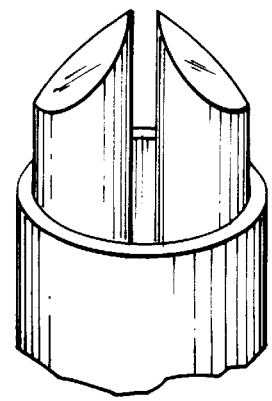
Fig_42   Fig_51A   Fig_51B
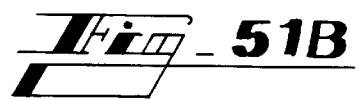
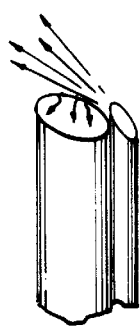
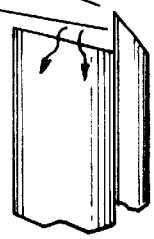
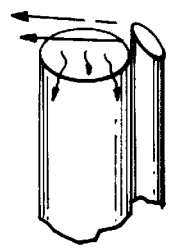
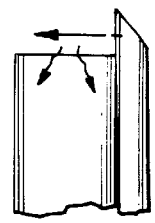
Fig_49B   Fig_49D   Fig_49A   Fig_49C
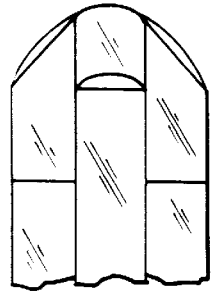
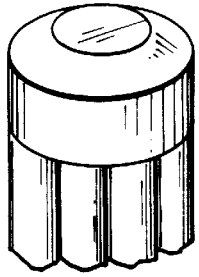
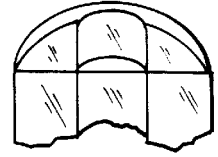
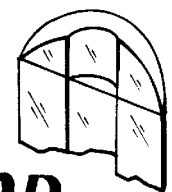
Fig_50A   Fig_50B   Fig_50C   Fig_50D

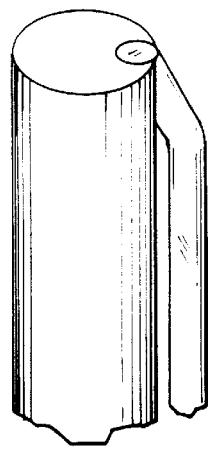
Fig_58
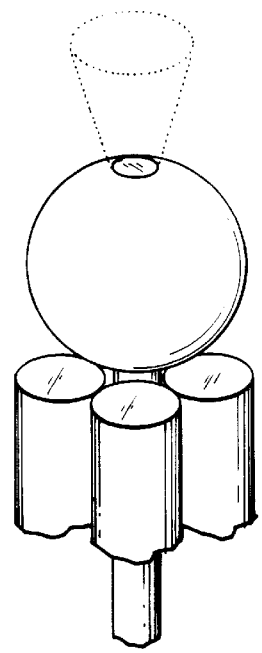
Fig_53B
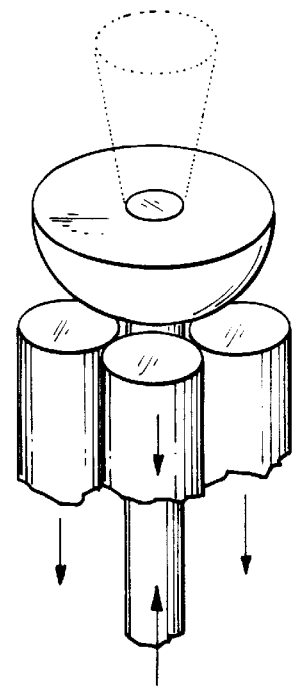
Fig_53A
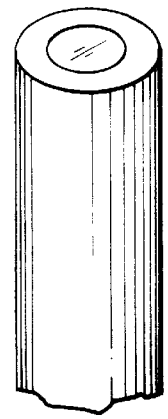
Fig_60
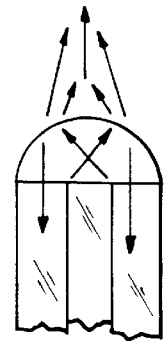
Fig_54
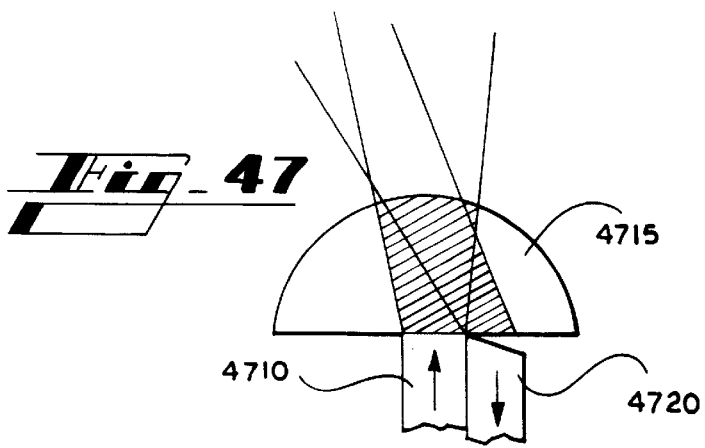
Fig_47

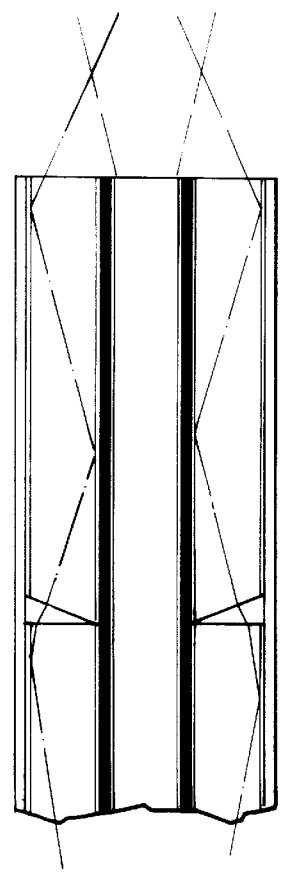
Fig_55A
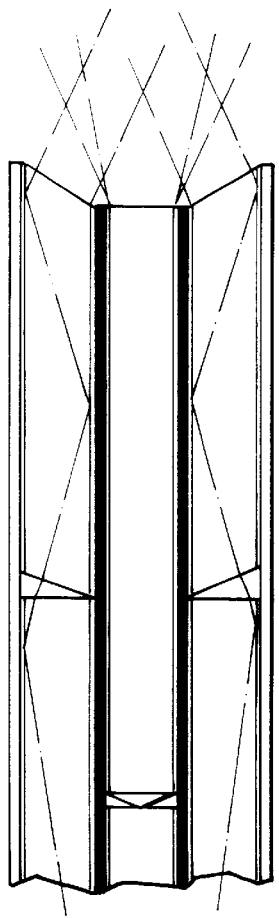
Fig_55B
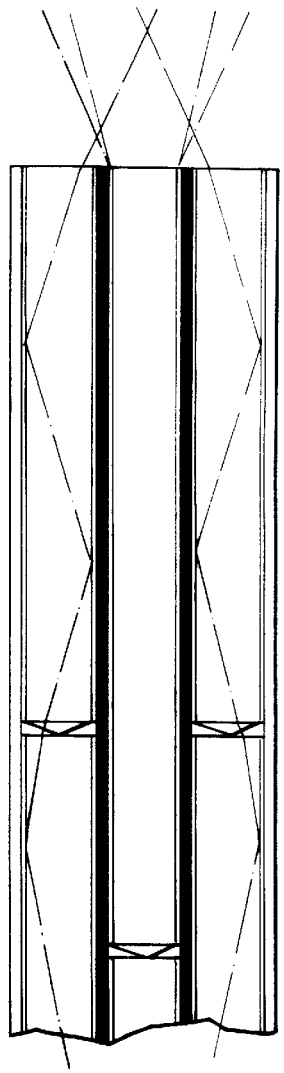
Fig_55D
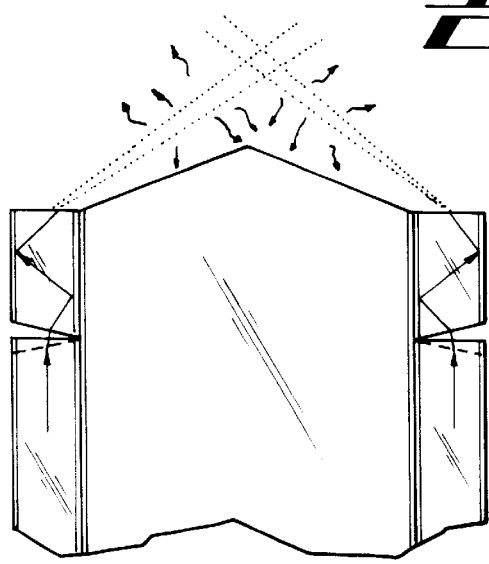
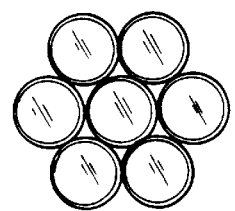
Fig_55C
Fig_55E

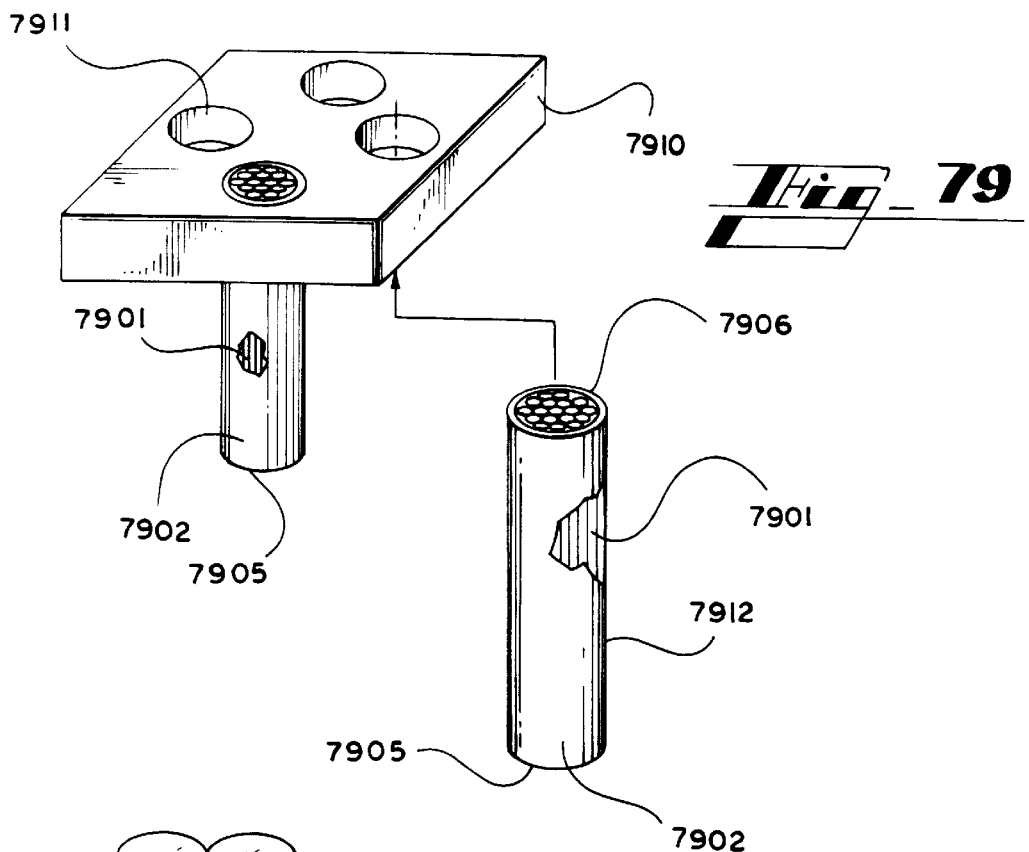
Fig_79
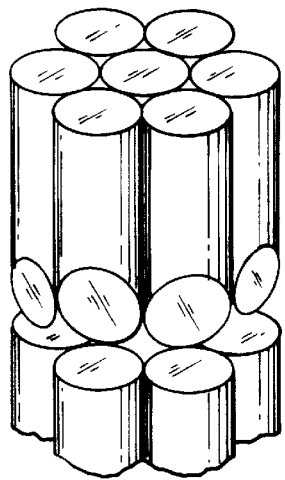
Fig_55F
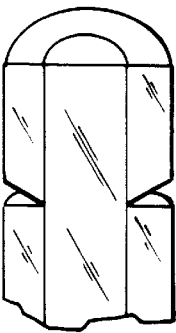
Fig_56A
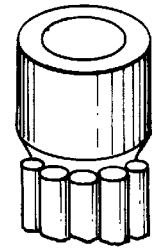
Fig_56B

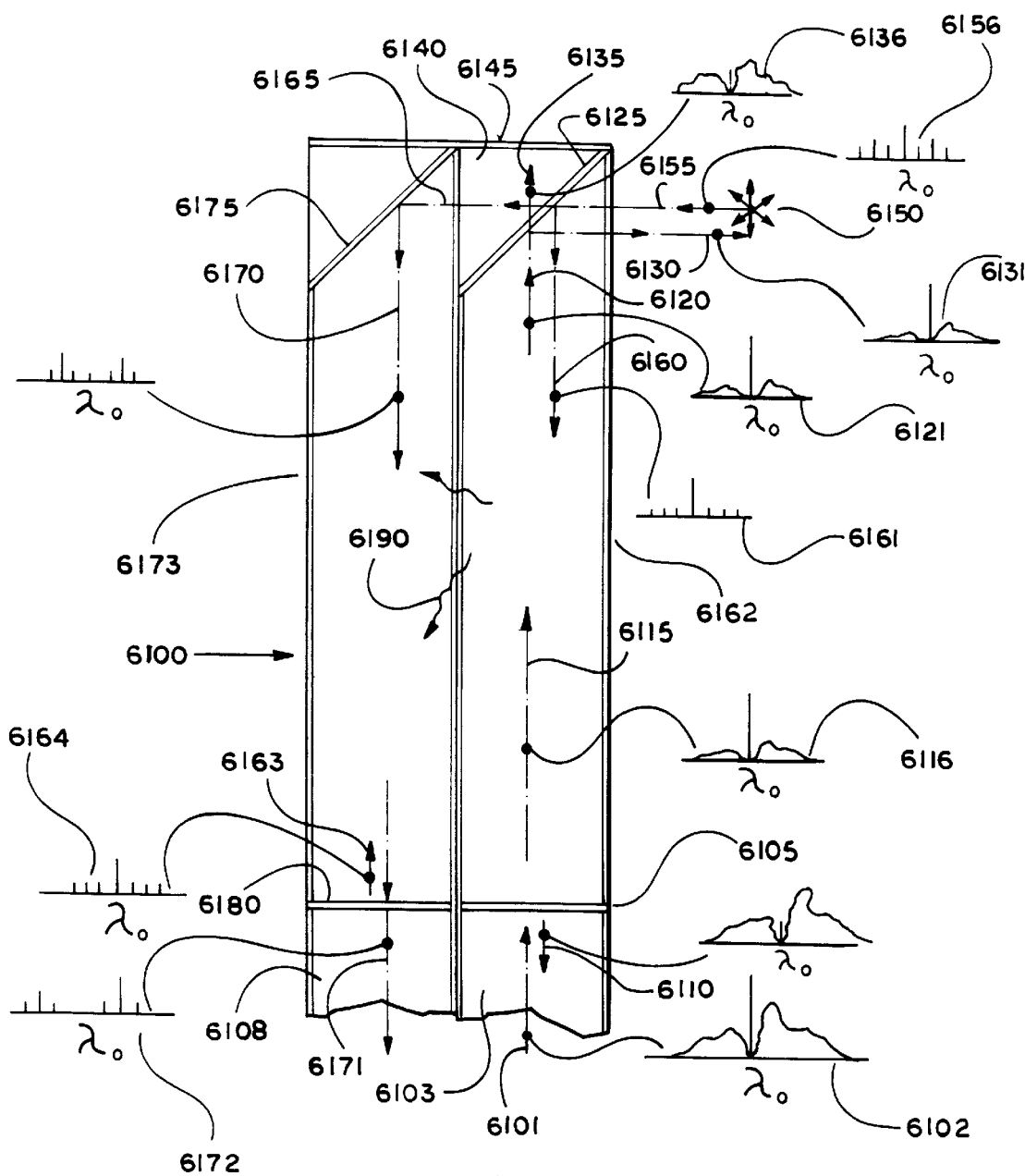
Fig_61

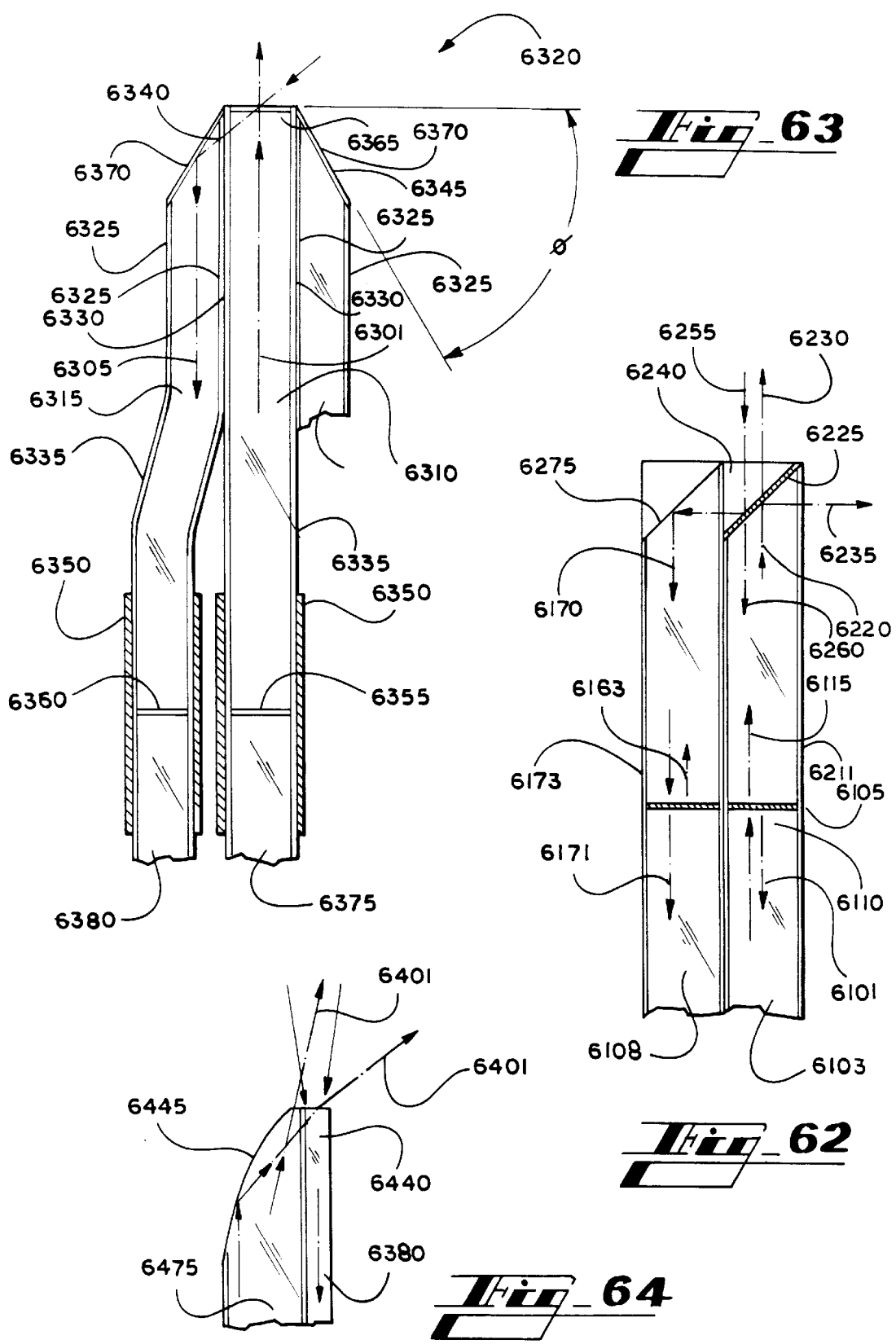

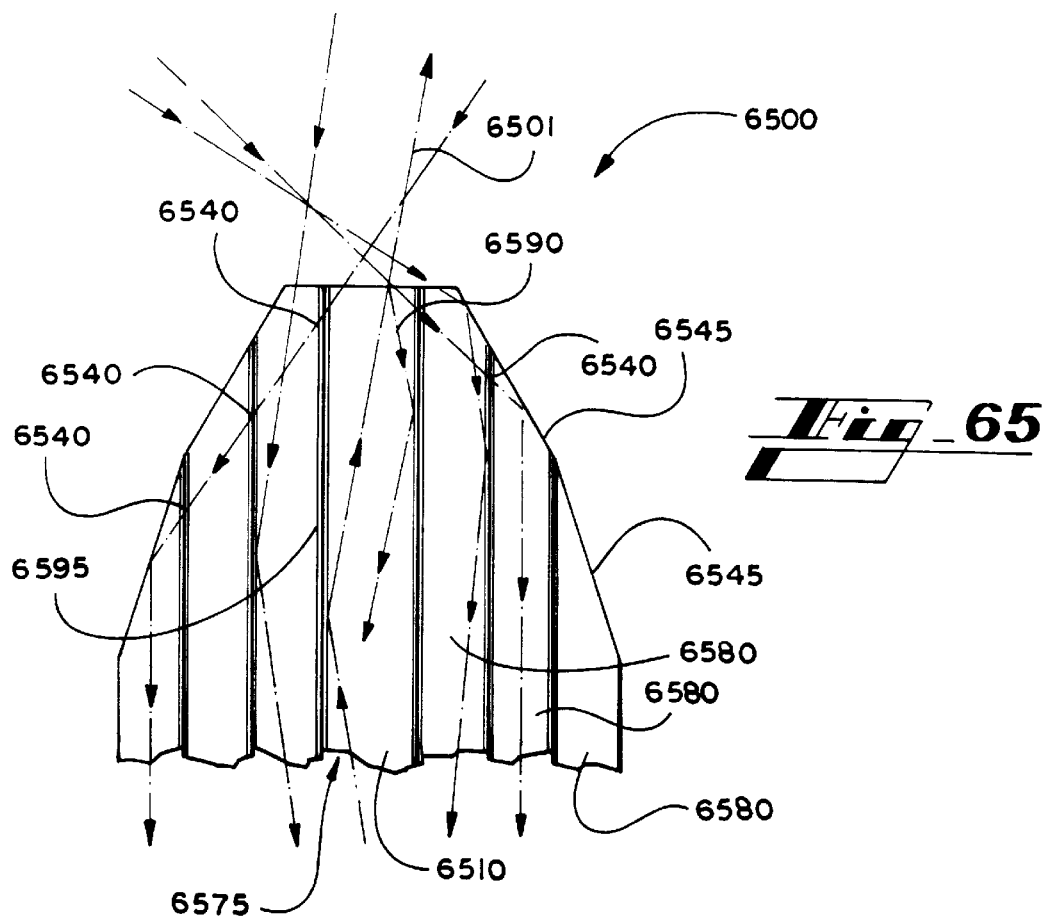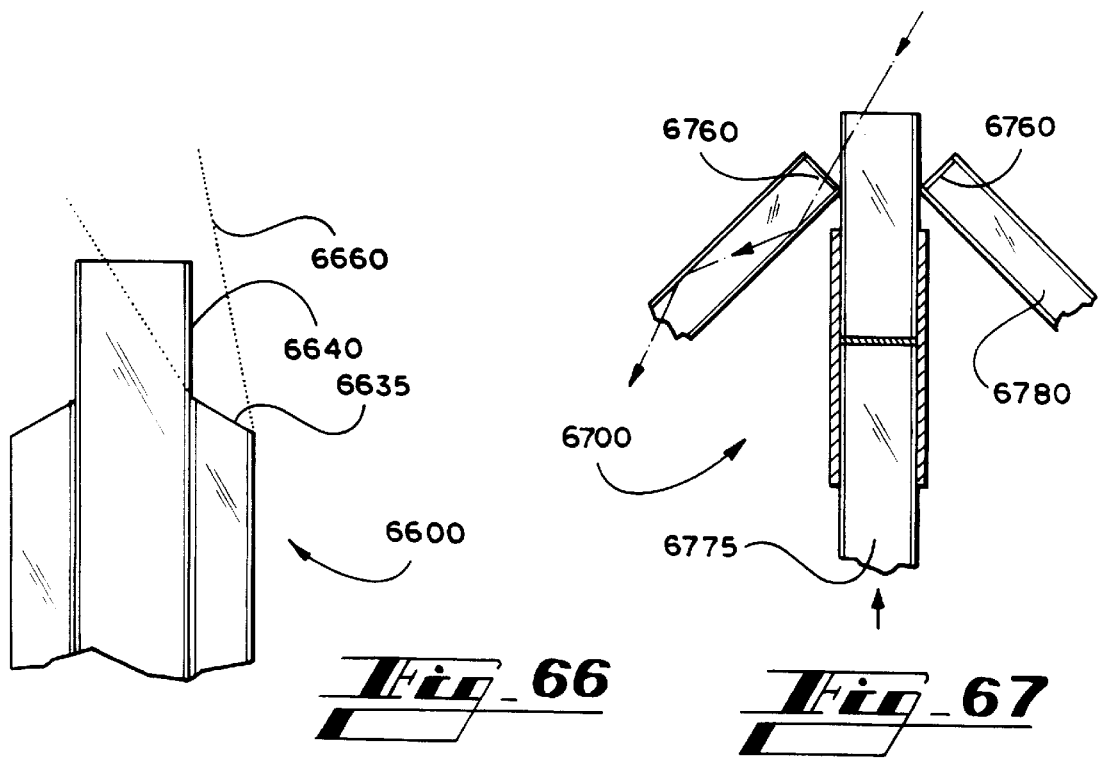

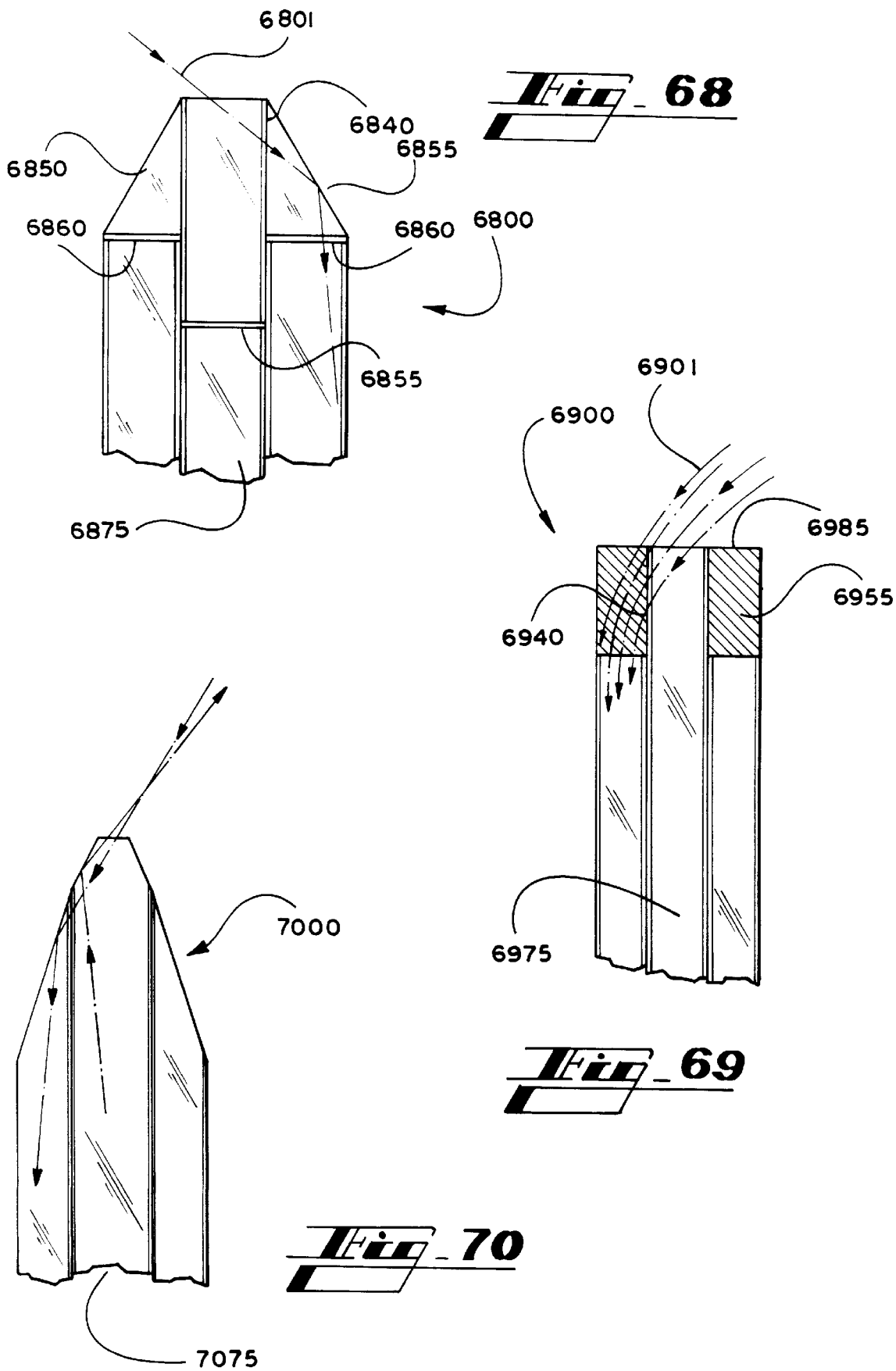

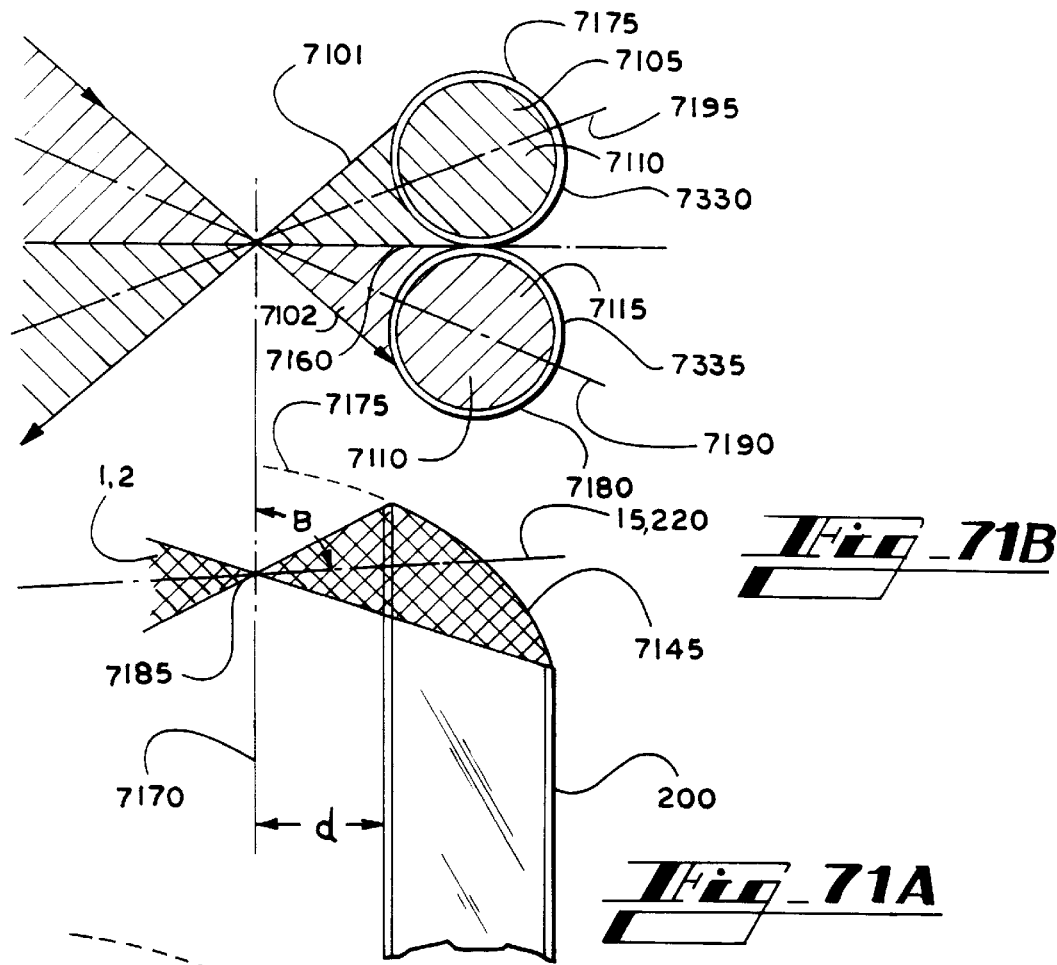
Fig. 71B
Fig. 71A
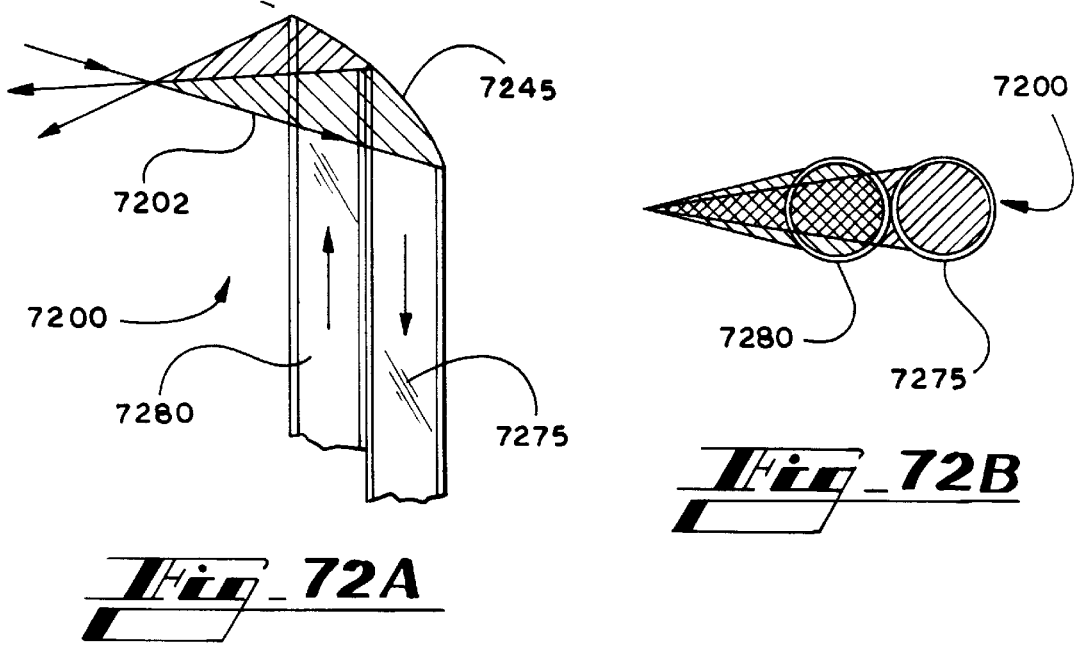
Fig. 72A
Fig. 72B

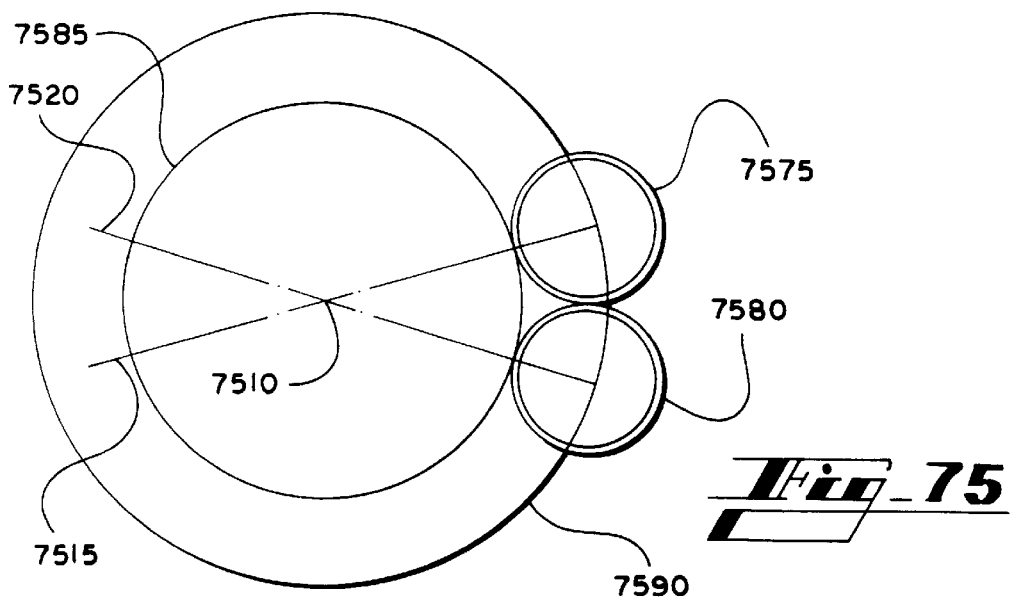
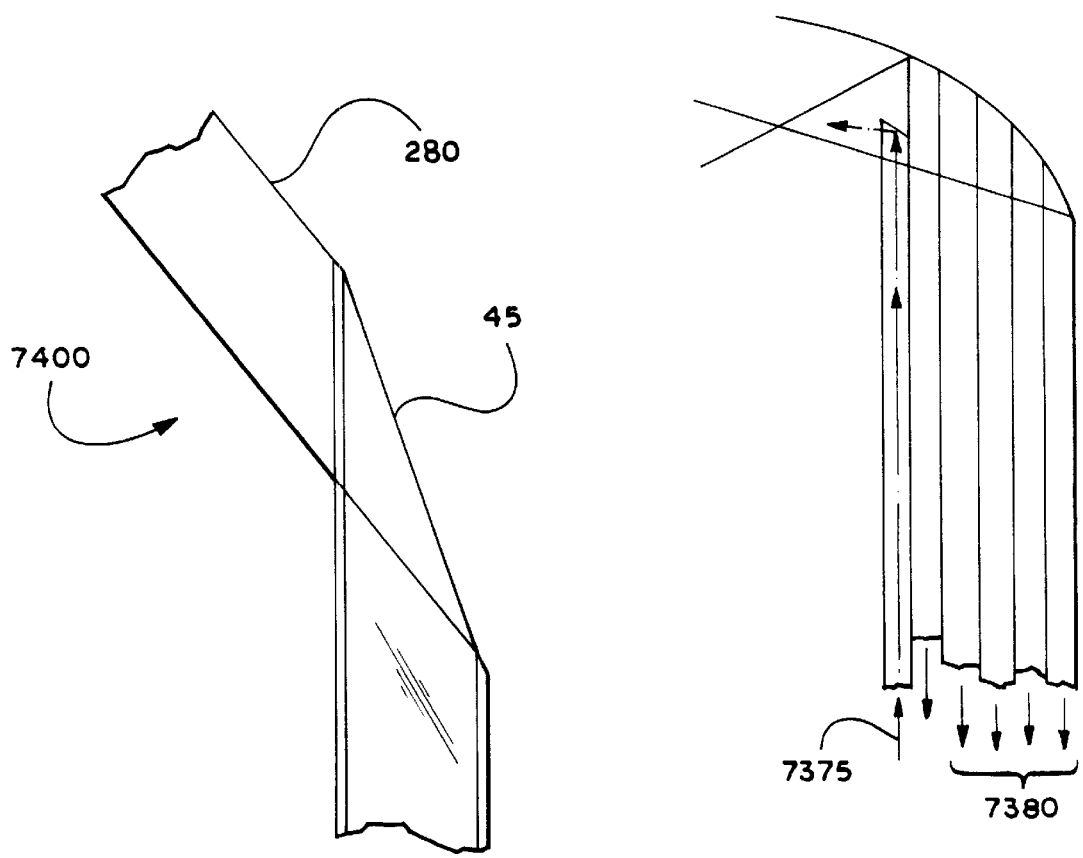

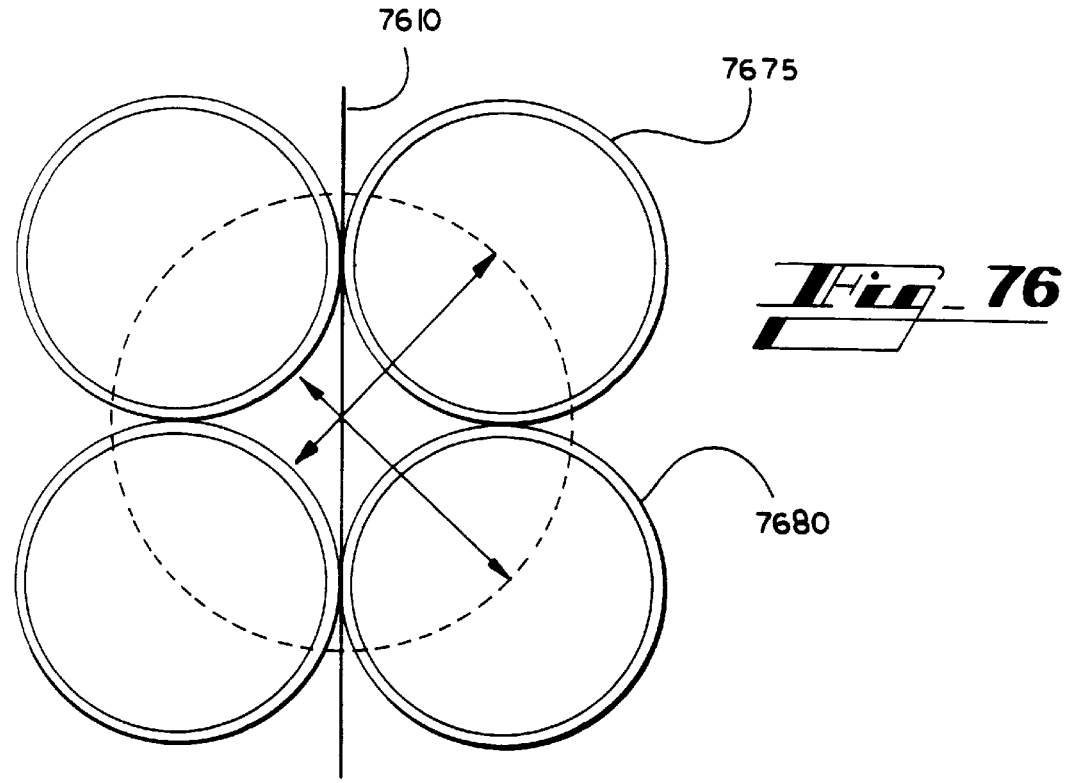
Fig_76
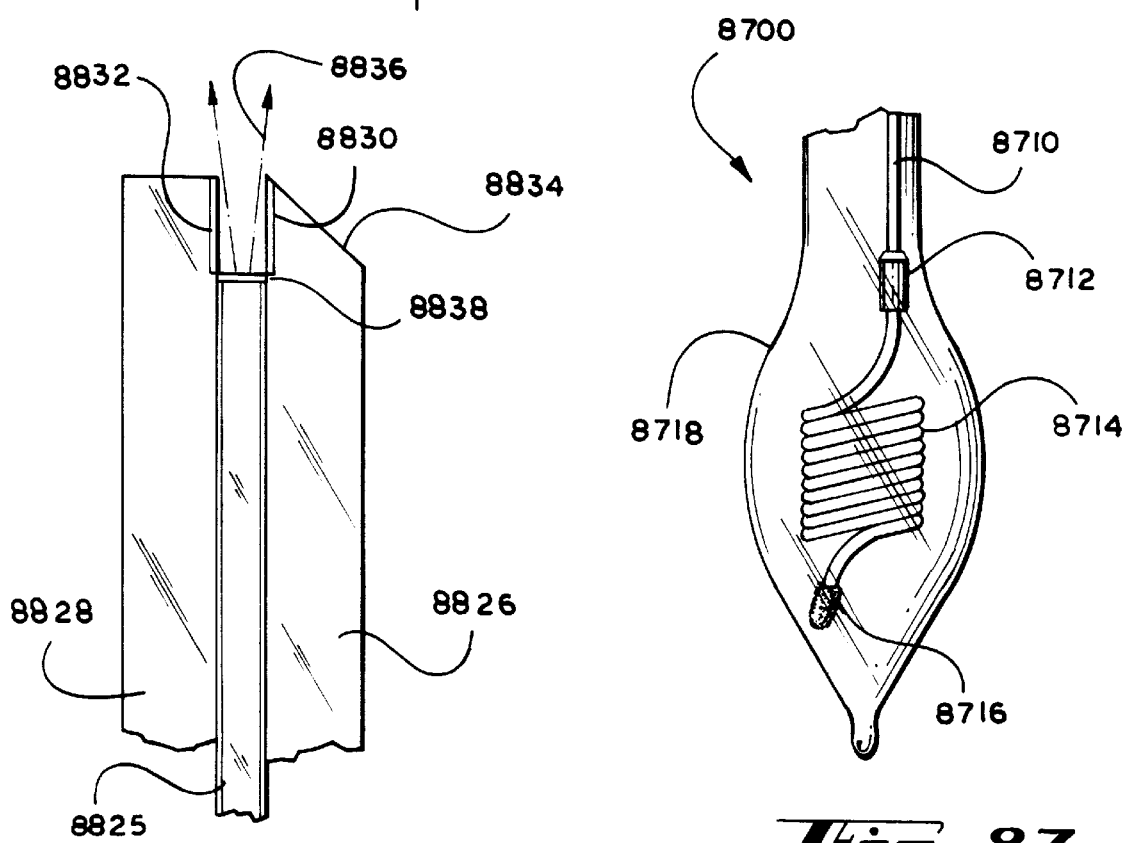
Fig_88
Fig_87

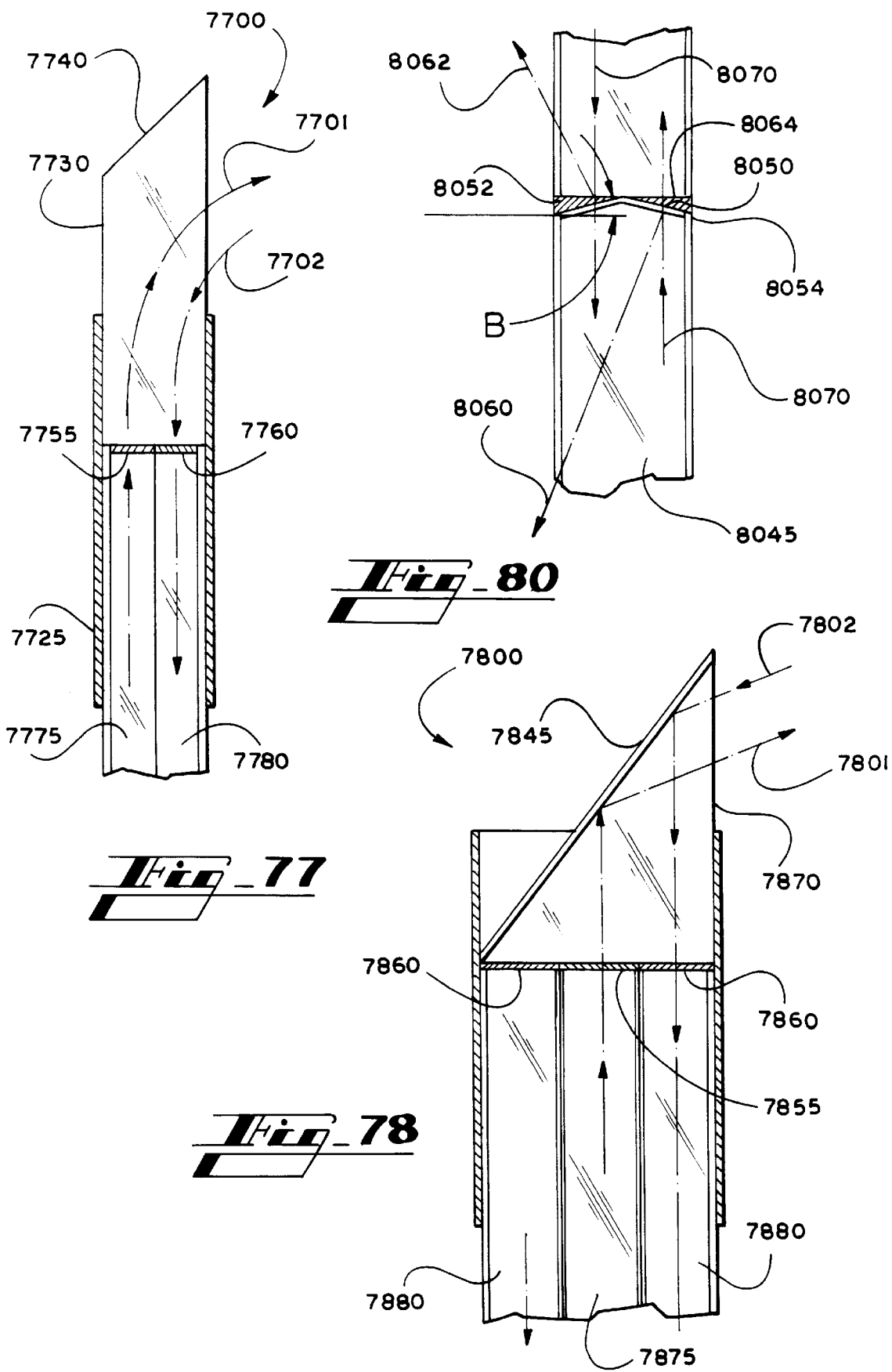

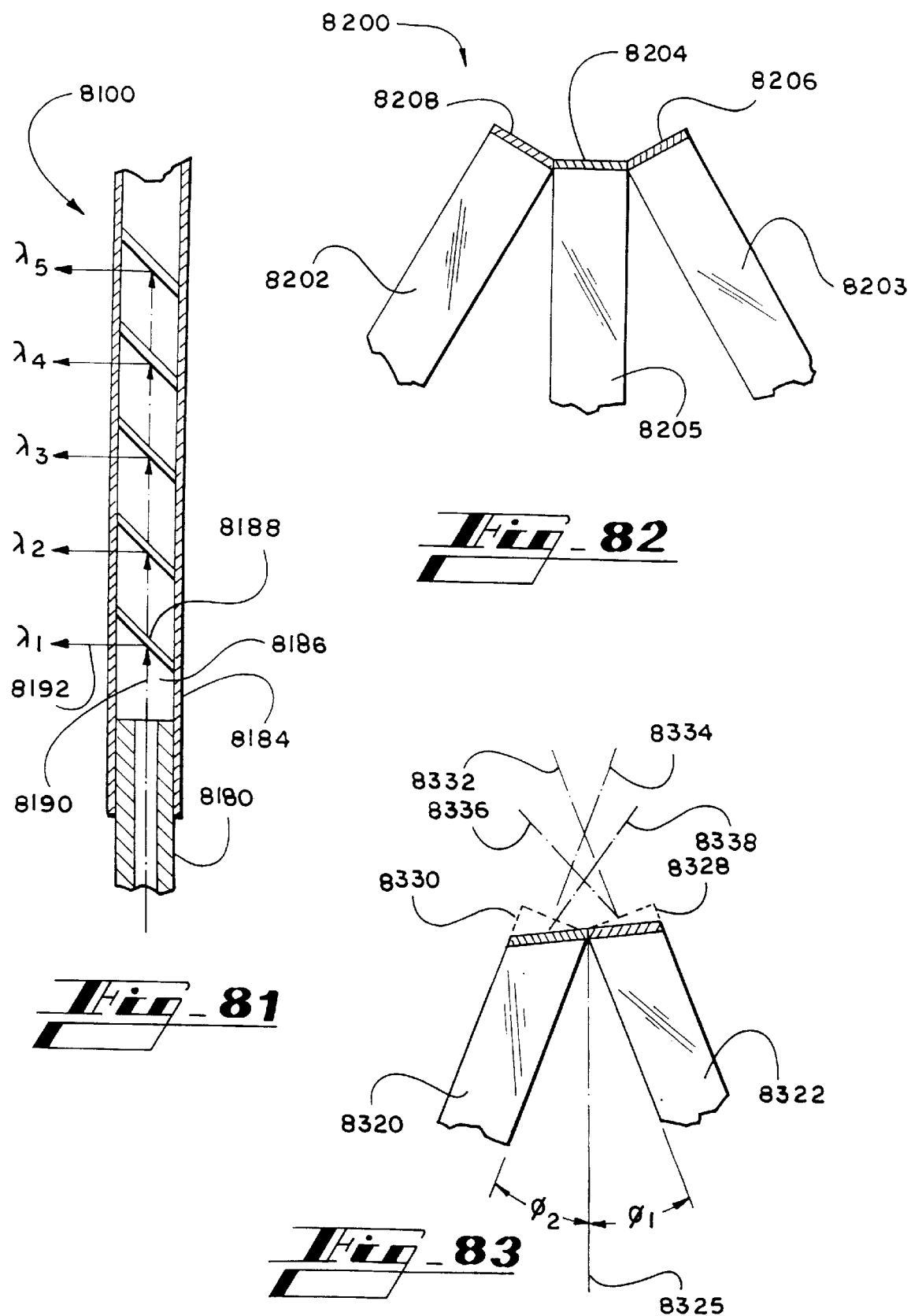

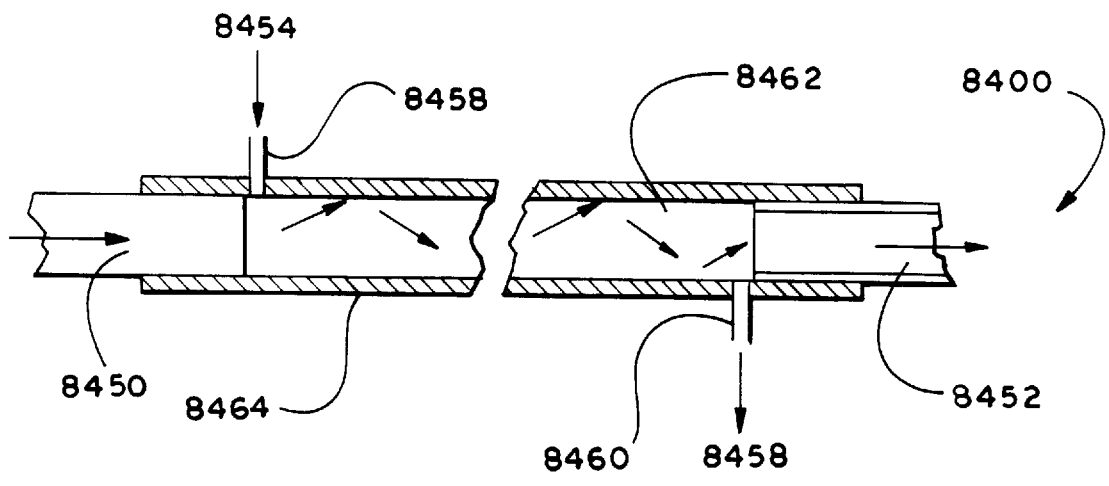
_Fig_84
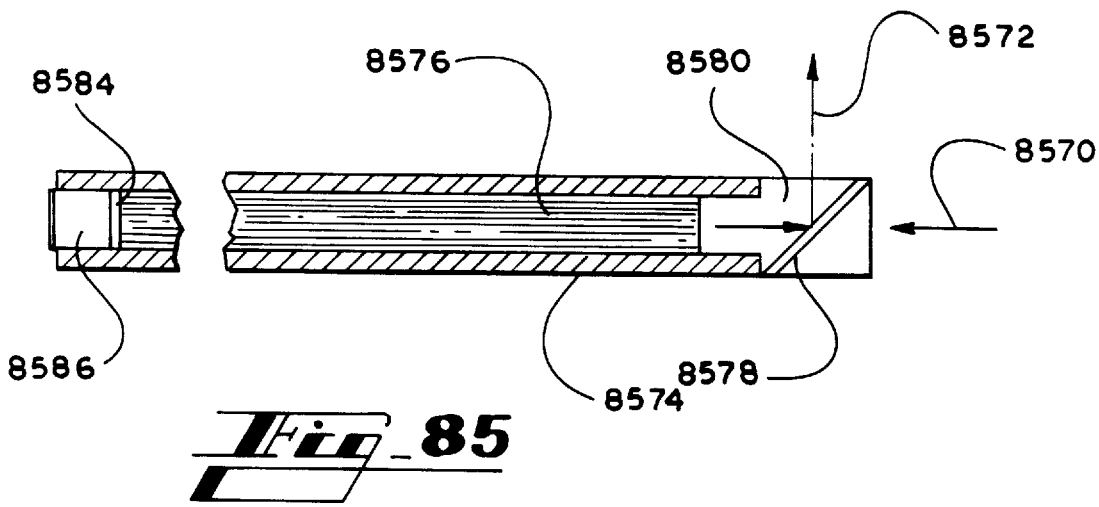
_Fig_85
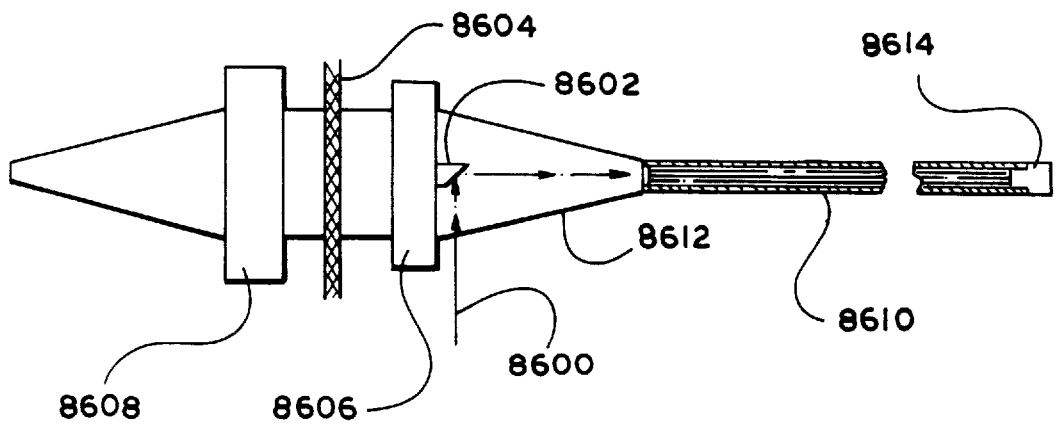
_Fig_86

COUPLERS FOR OPTICAL FIBERS

STATEMENT REGARDING RELATED APPLICATIONS

This is a continuation of U.S. patent application Ser. No. 08/819,979, entitled "Method and Apparatus for Improved Fiber Optic Management," filed Mar. 13, 1997, now U.S. Pat. No. 5,953,477 which is a continuation in part of U.S. patent application Ser. No. 08/561,484, entitled "Optical Fiber with Enhanced Light Collection and Illumination and Having Highly Controlled Emission and Acceptance Patterns," filed Nov. 20, 1995, and claims the benefit of U.S. Provisional Application Nos. 60/013,341, entitled "Fiber Optic Interface with Manipulated Delivery and Reception Sensitivities," filed Mar. 13, 1996, 60/036,504, entitled "Improved Fiber Optic Probe Assembly," filed Jan. 28, 1997, and 60/038,395, entitled "Improved Filtering of Optical Fibers and Other Related Devices," filed Feb. 14, 1997.

TABLE OF CONTENTS

STATEMENT REGARDING RELATED APPLICATIONS . . .
TECHNICAL FIELD . . .
BACKGROUND OF THE INVENTION . . .
LIGHT SCATTERING SPECTROSCOPY . . .
FLAT FACE, PARALLEL FIBER PROBES . . .
ATTEMPTS TO IMPROVE PROBE PERFORMANCE . . .
SUMMARY OF THE INVENTION . . .
BRIEF DESCRIPTION OF THE DRAWINGS . . .
DETAILED DESCRIPTION . . .
OPTICAL FIBERS IN GENERAL . . .
AN IMPROVED PROBE ASSEMBLY . . .
METHODS OF MANIPULATING LIGHT WITHIN A FIBER . . .
IMPROVED PROBE ASSEMBLY UTILIZING INTERNALLY REFLECTIVE SURFACES . . .
OPERATION OF AN EXEMPLARY PROBE ASSEMBLY . . .
PERFORMANCE OF AN EXEMPLARY PROBE ASSEMBLY . . .
COMPLEX SURFACES . . .
ADDITIONAL ASPECTS OF THE PROBE ASSEMBLY FILTERING MECHANISMS . . .
ADDITIONAL ASPECTS OF THE PROBE ASSEMBLY INSTRUMENT INTERFACE . . .
ALTERNATIVE EMBODIMENTS FIBER GEOMETRY . . .
SEPARATE ELEMENTS . . .
RELATED EMBODIMENT ALSO UTILIZING INTERNALLY REFLECTIVE SURFACES . . .
GRADIENT REFRACTIVE INDEX EMBODIMENT . . .
REFRACTIVE END PIECES APPLIED TO THE PROBE TIP . . .
PROBES EMPLOYING LIGHT MANIPULATION BETWEEN ADJOINING FIBER SEGMENTS . . .
SEPARATE METHODOLOGY . . .
A SINGLE FIBER EMBODIMENT . . .
DELIVERING AND COLLECTING LIGHT ALONG A COMMON AXIS . . .
DELIVERING AND COLLECTING LIGHT THROUGH A COMMON APERTURE . . .
FIBER OPTIC LIGHT MANIPULATION APPARATUS YIELDING SIDE VIEWING AND SIDE DELIVERY . . .
IMPROVED FILTERING TECHNIQUES FOR OPTICAL FIBERS . . .
THE FILTER APPLICATION PROCESS . . .
TOOLING . . .
FILTER DESIGN . . .
FIBER COUPLING . . .
SPECIAL CASES . . .
IMPROVED COLLECTION AND FILTERING OPTICS FOR CONFOCAL PROBES . . .
IMPROVED FILTERING . . .
AMPLIFIED RESPONSE . . .
SUMMARY OF THE DETAILED DESCRIPTION . . .
CLAIMS . . .

TECHNICAL FIELD

This invention relates generally to optical fibers, and more particularly to optical fiber probes that use manipulated delivery and reception regions to improve sensitivity to specific light-matter interactions.

BACKGROUND OF THE INVENTION

In recent years, the use of optical fibers has become increasingly widespread in a variety of applications. Optical fiber probes have been found to be especially useful for analyzing materials by employing various types of light-scattering spectroscopy.

Optical fibers offer numerous advantages over other types of source/detection equipment. In short, the fiber provides a light conduit so that the source-generating hardware and the recording apparatus are stationed independently of the subject under investigation and the point of analysis. Thus, analyses are conducted remotely in otherwise inaccessible locations. Previously unattainable information is acquired in situ, often in real time. This capability is sought in numerous industrial, environmental, and biomedical applications. The laboratory is moved on line in the industrial realm, to the field in the environmental sector, and in vivo in the biotechnical arena. Additionally, hardware and measurements are more robust, quicker, less intrusive, more rugged, less costly, and many other advantages are realized.

LIGHT SCATTERING SPECTROSCOPY

While transmission spectroscopy analyzes light passing through a substance, light-scattering spectroscopy entails illumination of a measure and and analyzing light that is scattered at angles relative to the incident source. The photon-matter interactions of the scattering events may be either elastic or inelastic. In an inelastic event, a photon's energy (wavelength) changes as a result of the light-matter interaction. In an elastic event, a photon's energy (wavelength) does not change. Absorption, the phenomena in which a fraction of photons are entirely absorbed, also plays a role in light-scattering spectroscopies. Raman, diffuse, reflectance, and fluorescence spectroscopies are of particular interest as they relate to vibrational and nonvibrational photogenic responses of a material.

The Raman effect describes a subtle light-matter interaction. Minute fractions of light illuminating a substance are Raman-scattered in random directions. Raman-scattered light is color shifted from the incident beam (usually a laser). The color (frequency) shifts are highly specific as they relate to molecular bond vibrations inducing molecular polarizability changes. Raman spectroscopy is a powerful technique for chemical analysis and monitoring. The resulting low light levels require sophisticated, expensive instrumentation and technical complexity. Suitable technology and products for on-line analysis of processes and environmental contaminants are just becoming available.

Specular reflectance relates to a surface's mirror-like aspects. Diffuse reflectance relates to light that is elastically scattered from a surface of material at diffuse angles relative to the incident team. For example, a projector screen diffusely reflects light while a glossy, new waxed car has a high specular component. Diffuse reflectance spectroscopy is important for chemical analysis as well as measuring visual perception. Among other things, it is based on particulate-scattering and absorption events.

Fluorescence relates to substances which absorb light at one wavelength then re-emit it at a longer wavelength as a result of electronic transitions. As an example, a "highlighter" felt-tip marker appears to "glow" green as it absorbs blue and ultraviolet light then emits it as green. Fluorescence provides a powerful technique for chemical monitoring.

Raman spectroscopy is a well-established laboratory technique and is generally recognized as having enormous potential for on-line monitoring and sensing. With the advent of stable lasers, cheap computing power, efficient detectors, and other new technological advancements, Raman spectroscopy is primed for widespread industrial monitoring deployment. In addition to process control monitoring, it will be utilized in specialized monitoring and sensing devices ranging from neuroimaging to environmental monitoring, to in vitro and in vivo medical testing.

Raman spectroscopy involves energizing a sample with a high-power, narrow-wavelength energy source, such as a laser. The laser photons induce low intensity light emissions as wavelengths shift from the laser's. The Raman effect is an elastic scattering of photons The emitted Raman light is collected and analyzed with a specialized instrument.

The spectral positions (colors) of the shifts provide fingerprints of the chemicals in the sample. Thus, Raman spectroscopy provides a means for chemical identification. The intensity of the shift (the spectral peak height) correlates to chemical concentration. Thus, a properly calibrated instrument provides chemical content and concentration. In practicality, Raman spectroscopy is technically complex and requires sophisticated, expensive instrumentation.

Raman spectroscopy is well suited to aqueous-based media without sample preparation. From this standpoint, it is an ideal tool for process control medical testing and environmental applications. Thus, Raman spectroscopy has great potential for real-time monitoring and is being vigorously pursued.

The basic concept for a probe-based, on-line Raman instrument is simple. Laser light is directed down an optical fiber to a remote probe. The laser light exits the fiber and illuminates the sample medium. Another fiber picks up the Raman-emitted light and returns it to the instrument for analysis.

In practicality, the engineering challenges for a robust physical probe implementation are substantial. In addition to the optical performance expected by laboratory instruments, a probe must be hardened to withstand extreme physical and chemical conditions. Optical characteristics must also remain constant as dynamic conditions change.

Optical aspects of probe engineering require particular design finesse. The Raman effect involves very weak signals. Raman emissions may be one trillionth as intense as the exciting radiation. Subsequently, the probe must be incredibly efficient in collecting and transmitting Raman-emitted light. And, the signal must not be corrupted by extraneous influences. As an example of the sensitivity, Raman instruments typically feature cosmic ray filters. The mechanisms identify and discard measurement data samples influenced by passage of a single cosmic ray photon through the detector.

A phenomenon known as the silica-Raman effect has proven especially troublesome for those engaged in remote Raman spectroscopy. As laser light is transmitted over optical fibers, a subtle light-matter interaction inherently occurs. The laser light and the silica in the glass fiber interact generating "silica-Raman" light. The extraneous silica-Raman light becomes waveguided in the fiber and hopelessly mixed with the laser light. The purity of the laser light is corrupted. Fiber fluorescence causes similar problems.

Remote Raman spectroscopy employs optical fiber between the base instrument and the remote probe or process interface. Optical fiber delivers laser light from its source to the probe. Separate fiber returns sensed light from the probe to an instrument for analysis. In both delivery and return, undesirable silica-Raman light travels in the fibers concurrently with desirable laser and sensor light. A major obstacle in fiber-optic-based Raman spectroscopy has been in separating the desirable light from the undesirable silica-Raman light.

FLAT FACE, PARALLEL FIBER PROBES

Standard optical fibers deliver and receive light within narrow angular confines. Consider a "probe" that is formed by mounting two standard, flat-face fibers (i.e., a source fiber and a collection fiber) in parallel. The functionality, operation, and limitations of this probe will be analyzed to present relevant technical requirements. The technical discussion addresses, among other things, issues of optical efficiency. Efficiency is a critical parameter concerned with the ratio between the illumination energy verses the energy of collected light.

Increased optical efficiency has significant benefits. As efficiency is increased, system performance is dramatically boosted. In sophisticated instrument systems, enormous efforts, expense and other considerations are devoted to produce small, marginal performance gains in the detector subsystem. With an optimized probe, tremendous gains are readily realized. Gains in probe efficiency vastly dominate fractional electronic and detector improvements. With increased probe performance, the overall system benefits with reduced noise, increased stability, faster response, and better repeatability. Required illumination intensity is minimized. This translates to reducing intrusive aspects and ensuring the subject under analysis is not damaged or altered. In addition, much less expensive opto-electronic components can be employed.

In the flat-face, parallel-fiber probe, the source fiber delivers illuminating light in the form of a diverging light beam. The collection fiber has a receptivity zone that is similar in shape to that of the illumination zone. However, the collection and illumination zones are offset from one another, each originating from its respective fiber face. As the zones expand outward from the fiber end faces, they begin to overlap. Under normal circumstances, only in this overlapping region can the source fiber deliver illumination and the collection fiber gather light from the target. The lack of overlap between these regions produces numerous troublesome effects. A second, though not entirely distinct, set of problems is associated with the angular orientation of light rays within the illumination and collection cones. These problems are described below.

In many common applications, the investigative medium is light-absorbing, the probe might be deployed in a chemical mixture that is slightly black but not fully opaque. For example, various biological tissues are well known as light-absorbing matrices. And, the sample need not be dark in the traditional sense. Even visually transparent media often strongly absorb ultraviolet and/or infrared light. In a light-absorbing medium, the illumination light must penetrate some distance into the environment prior to reaching a position in which the detector fiber can actively collect returning light. Since the source light is absorbed as it traverses this distance, its intensity is diminished before it reaches an active target zone. Once the illumination light reaches an active target zone, it triggers release of potentially collectible sample light from the target. Depending on the application, the sample light may be generated by any of various photonic mechanisms. Assuming a passive target, the sample light is reduced in strength from the illuminating source light. Depending on the phenomenon of interest, the attenuation is severe. Before capture by the collecting fiber, the sample light must traverse a path through the absorbing medium further reducing the signal strength by attenuation.

Initially, this problem appears readily solved by increasing the illumination intensity. While in certain cases this technique might be effective, in many circumstances, it is not feasible. As the medium absorbs source light energy, it can be irreparably damaged. Even without damage, minimum light intensity translates to minimum intrusive attributes. And, in addition to damage, photochemical reactions are inadvertently initiated in certain circumstances. Therefore, applications that will not tolerate high intensity illumination may preclude the use of a flat-face, parallel fiber probe. In addition, the goal of minimizing illumination light intensity is desirable in almost all uses that are currently being investigated.

A second problem exists in environments that involve elastic particulate-scattering media, such as slurries, mists, aerosols, paints, and various other media. Biological tissues are well known for these types of light-scattering characteristics. Most unpurified samples scatter light to a certain degree and often intensely. Although light scattering occurs by various mechanisms, Rayleigh and Mie-scattering is common and produces strong influences. As with the previous example, the illumination energy must traverse a path of attenuation prior to reaching a target zone for which the collection fiber is receptive. And, the target-generated light must likewise traverse a path through the scattering agent prior to reaching the collection fiber. As with the example of the light-absorbing sample, minimizing delivered light intensity to prevent sample damage is a factor.

For elastic light-scattering media, additional detrimental effects are observed. Assume a distinct target is stationed within the particulate-scattering medium and is positioned within the region where the illumination and light-gathering zones overlap. Illumination is elastically scattered as it traverses a path to reach the target. Although the direct pathway may lie outside of the collection fiber's receptivity zone, it is incorrect to surmise that this scattered light cannot be captured by the collecting fiber. The incorrect conclusion is based upon a single scattering event which primarily redirects a source ray to a new angular orientation. The population of angular orientations for an arbitrary single ray is statistically determined and is a function, among other things, of the characteristics of the scattering agent. These characteristics include, but are not limited to, particle size, shape, refractive index, and reflective qualities. Granted, for a single scattering event to generate a ray to be received by the collection fiber, the event must occur within the collection fiber's receptivity zone. Unfortunately, light scattering, particularly Rayleigh and Mie-scattering, often is a multiple event phenomenon. Typically, a source ray undergoes multiple scattering events and is redirected many times. Thus, the ray path is complex as it interacts with various sample particles.

As an overly simple example, consider a ray exiting the source fiber parallel to the fiber axis at a zero-degree heading, and is scattered by an event perpendicularly directing it to a 90-degree heading. At this heading, it enters the collection fiber's zone of receptivity. While in this zone, the ray undergoes a second event directing it to a new heading for intersection with the collection fiber's end face. The ray is then captured by the collection fiber.

Light captured by the collection fiber prior to undergoing intended interaction with the target is usually highly detrimental. The negative effect transcends diminishing the intensity of source illumination delivered to the target. This light becomes indiscriminately mixed with the desired light within the collection fiber. This "stray light" severely corrupts the process of various analytical measurements. Typically, the stray light becomes indistinguishable from the desired light. Stray light levels may be dependent on various environmental factors. In the aforementioned example, stray light is a function of the quantity of scattering agent present in the optical path. Assuming this quantity is an uncontrolled application variable, the effect cannot be readily eliminated by referencing of similar compensation.

The situation in which scattering medium separates an intended target from the probe tip is quite common. For example, for in vivo analysis of biological samples, various light-scattering aqueous solutions separate the probe tip from the target. For example, biological tissue is often surrounded by fluids containing scattering agents, such as tissue particulates and blood.

A distinct class of sensor measurements is concerned with analyzing particulate-scattered light to ascertain particle characteristics. In this configuration, returning light from the particles is analyzed to ascertain turbidity, particle concentration, and related parameters. These measurements are highly sought in the biotechnology field for both bioprocesses as well as in vivo and in vitro biomedical applications. Industrial applications are likewise numerous. In this instance, it is desirable to collect and analyze light that has undergone a minimal number of scattering interactions. It is understood from the previous discussion that the greater the distance from the probe end face to a zone of mutual illumination and collection, the more likely the collected light will have undergone multiple interactions. Therefore, for this application, other related criteria addressing the extent and spatial duration of the zone overlap, and various illumination and collection angles can and should be optimized.

Consider an application in clear media, which exhibits neither light absorption nor particulate scattering. As the distance from the probe end face increases, the zones of illumination and receptivity increasingly overlap and asymptotically approach full concurrence. However, it would be incorrect to assume the optimal target location is at a position removed from the probe end face, where the illumination and collection zones are basically in concurrence. An opposing factor must be considered. As distance from the probe end face increases, the relative sizes of the fibers nonlinearly decrease. At a point removed from the end face, the collection fiber possesses light-gathering abilities within a solid angle. These two opposing factors can be modeled to calculate an optimal target distance which maximizes the signal for a given set of application criteria, including beam divergence, fiber size, and fiber separation. The mechanism by which the target returns source light and the characteristics of this light are also important. Nevertheless, the solid angle effect is dominant and the collection fiber's light-gathering ability decreases dramatically as distance from the fiber end face increases. From this perspective, it is highly advantageous to be able to position the target as close to the probe end face as possible. As with the discussions of the probe's other limiting factors, intensity is a major factor.

Consider an application in which a flat face, parallel fiber probe is used for Raman analysis of a clear fluid. In this case, the medium through which the detection and collection beams are projected and the target are one and the same. As the collection and illumination zones extend from the probe tip, they overlap as previously described. Unfortunately, at a distance away from the probe tip at which significant overlap occurs, the illumination beam has diverged, and its intensity has diminished. For the collection fiber, a similar scenario exists. At a distance at which zone overlap occurs, the relative size of the collection fiber is reduced. The solid angle within which the fiber has the ability to collect light is severely reduced over that close to the collection fiber end face.

Along a similar line of reasoning, consider a probe investigating fluorescence characteristics of a liquid in a flat-bottom beaker. If the liquid is sufficiently transparent, a portion of the light penetrates the liquid to the beaker bottom and is reflected back to the detector fiber. This reflection manifests itself as stray light and corrupts the acquired data. If the probe had the ability to angularly control illumination and collection, then the stray light problem would be avoided by directing the reflections to miss the detector fiber.

The dependence of captured light intensity upon target distance from a flat face, parallel fiber probe tip is often utilized in the prior art to create a displacement sensor for position measurement. The dynamic range and characteristics of such sensors are limited by available source and detector pattern geometries.

Another important factor related to the probe is power density of the delivered illumination. Power density may be expressed in watts per unit area. Power density in the medium is highest at the surface of the illuminating optical fiber and decreases as the source beam diverges. Thus, fibers that do not rapidly diverge maintain power density as the source beam is projected into the medium. Unfortunately, the source beam must diverge in order to deliver illumination light into the collection fiber's zone of receptivity. For a given quantity of light injected into the proximal end of a source fiber, power density at the fiber's distal end face at the probe tip decreases as the fiber core diameter increases. As previously described, the lower the power density, the less intrusive the probe and the less potentially damaging the source energy.

In addition to the described criteria, the angular orientation of rays within the illumination and collection zones are of interest. Depending on the intended application, this aspect is critically important. For a flat face, parallel fiber probe, emitted illumination rays are oriented within the divergence angle of the illumination pattern and centered about the fiber's axis. The fiber axis is, therefore, the average angular orientation of the emitted light rays. A similar scenario exists for the receiving/collection fiber.

Consider gathering light from a theoretical point source positioned a short distance from a collection fiber end face. The fiber's cone-shaped collection pattern (extends outward from its end face. If the point source is positioned outside the (collection pattern, no light is collected by the fiber. At this position, light rays incident on the fiber end face are not properly angularly oriented for collection. Similarly, if the point source is positioned within the collection pattern, a portion of the point source rays are collected. For a given stand-off distance of the point source from the collection fiber end face, the fraction of collected light varies across the collection pattern. With the point source at the center axis of the pattern, the fraction collected is maximum. Moving at a right angle to the center axis of the fiber, the zone of maximum collection extends across a portion of the collection pattern. Moving further towards the outer boundary of the collection pattern, the fraction of collected light is reduced. This reduction in collected light is due to the fact that near the edges of the collection pattern most of the point source rays striking the fiber end face are improperly angularly oriented for collection. The described scenario is important in modeling and understanding the effects of collection and illumination zone overlap in fiber optic probes. In the described flat face, parallel fiber probe, the overlap occurs only in the outer fringes of the conical illumination and collection zones. The center, more critical regions of the illumination and collection patterns do not coincide with one another. Thus, efficiency is poor.

For many measurements, the angular orientation of illumination and collection light is crucial. As previously described, Rayleigh and Mie-scattered light is often angularly biased and the bias orientation is analytically important. Similarly, for measurements related to visual perception, the angular orientation is often crucial. Gloss is measured at specific angles of illumination and collection. Various material parameters such as paper brightness are likewise measured. For color measurements, illumination and receptive angles are often specified according to the material under analysis and various industry-specific standards. Often, diffuse illumination is desired. Perfectly diffuse illumination has no angular bias; the target is illuminated by light rays incident from all directions. Perfectly diffuse illumination is never fully attainable; nevertheless, it can be approached.

In addition to visually oriented measurement such as color, texture, smoothness, and gloss, diffuse reflectance measurements are widely utilized in analytical measurements. In many of these measurements, it is desirous to minimize the specular component of reflection. In so doing, collection of source light that has not undergone the desired interaction with the target is minimized. This characteristic is desired for diffuse reflectance measurements in the visible, ultraviolet, near-infrared, and infrared regions. It is also often desired for general light-scattering measurements including fluorescence and Raman spectroscopy. It is readily seen that a flat face, parallel fiber probe is limited in its capability to deliver diffuse illumination. These measurements are highly sought for a variety of industrial and biomedical applications.

In addition to attaining light-diffusion-related measurements based upon illumination of a target with highly diffuse light, another technique is of interest. In this technique, light is angularly directed at the target such that the specular light from the target surface is reflected away from the light-collection device. By this means, the collector is only receptive to light that the target scatters in a non-specular fashion and the light-collection device is not receptive to specular light. It is readily seen that a flat face, parallel fiber probe lacks the capability for angular light control to achieve this goal.

Consider a flat reflective surface placed in front of the flat face, parallel fiber probe so that it is perpendicular to the fibers. If the surface is positioned within the region of overlapping receptivity and illumination, then the collection fiber receives and transmits source light projected from the reflective surface. However, the received light is a small fraction of that available. Because the angle of incidence equals the angle of reflection, the majority of the light is directly reflected back and away from the collection fiber. The axis of the reflected light remains concurrent with the source fiber's axis. The fact that the optical axis of the illumination from the source fiber remains fixed prevents manipulating the optical patterns to change the percentage of surface-reflected light from the collection fiber.

As previously described, light reaching the collection fiber is a function of the distance from the flat reflective surface to the probe end face. This distance dependence can be utilized for the purpose of displacement sensing. However, the lack of ability to manipulate the optical axis of the illumination and collection cones limits the controllability of the measurement dynamics. It further limits the overall ability to achieve specific application goals, such as linearity, dynamic range, sensitivity and related criteria. And as previously mentioned, the capability to manipulate the angle and axis of illumination incidence facilitates the ability to maximize or minimize, desirable or undesirable surface reflections. This capability, which a flat face, parallel fiber probe lacks, can be utilized to significant advantage.

In certain sensing applications, the parameter under investigation responds inadequately to light of desirable wavelengths. For example, suppose an arbitrary chemical has an infrared signature suitable for photonic sensor development, but the appropriate infrared light does. not readily transmit with conventional optical fibers. In many situations such as these, visible light and standard optical fibers may be successfully utilized. This may be accomplished by introducing an indicator material that undergoes a visible color change upon interaction with the chemical species of interest.

To successfully employ indicator-based fiber optic sensors, fiber must illuminate the chemical indicator and collect light from it. Although this sensor methodology encompasses many techniques, one method involves coating the fiber end face with the indicator material. If a single fiber's end face is coated and the fiber is utilized as a bi-directional light conduit, poor isolation between delivered and collected photons can result.

Due to shortcomings associated with a flat face, parallel fiber probe and it, ability to control illumination and collection, complications arise in illuminating and collecting indicator light. A probe able to project illumination light onto a clearly defined indicator zone is highly preferred over a flat face, parallel fiber probe. For many situations, the ideal probe's desirable features include the capability to project illumination light directly onto a collection fiber whose end face coated with the indicator. In this superior configuration, only light interacting with the indicator reaches the detector—thereby eliminating stray light.

The preceding discussion has focused on a probe consisting of two parallel-mounted fibers (one source and one detector fiber). The progression and correlation to bundles of fibers in various configurations is readily appreciated and followed by those skilled in the art. Although bundles potentially overcome some of the pre-described limitations, significant limitations remain. And, the usage of bundles introduces additional problems and undesirable characteristics.

ATTEMPTS TO IMPROVE PROBE PERFORMANCE

From the preceding discussion, it is apparent that the ability to direct and manipulate illumination and receptivity zones of optical fibers is highly desired. Several prior art techniques have been employed to manipulate a probe's illumination and receptivity characteristics and to address the input/output constraints of optical fibers. For the reasons set out below, these methods are limited in terms of their effectiveness for many desired Raman instrumentation applications.

One approach employs optical fibers with varying numerical apertures in order to gain better control over the entry/exit characteristics. For example, by employing fibers with higher numerical apertures, the light-gathering ability is increased. This approach includes several drawbacks. First, the required fiber materials have characteristics not suitable for high-end instrumentation application including environmental sensitivity, usage restrictions, and the generation of extraneous responses. Second, physical laws limit the extent to which a fiber's acceptance characteristics can be extended. Third, a fiber's delivery pattern/field-of-view can only be broadened or narrowed but not steered off axis or directed to view in a specific region. Fourth, a wide acceptance angle on the input end of the fiber translates to a wide divergence on the output end. While a high numerical aperture fiber increases light gathering on the collection end, it delivers its light to a detector system in a widely diverging angle. In many cases, the delivery of widely diverging light to the detector system is detrimental to achieving acceptable performance.

Another approach employs expanded-beam external elements, such as lenses and mirrors, to manipulate the illumination and receptivity characteristics. These elements are bulky, expensive, sometimes fragile, often lossy, difficult to align, and susceptible to environmental influences. Additionally, it is difficult to engineer a highly robust package. For example, larger, more robust components, have higher mass and increase system susceptibility to mechanical shock.

If an individual lens is dedicated to each collection and illumination fiber, then the ensuing device becomes large and bulky. Furthermore, the larger the assembly, the further apart and less efficient the collection and illumination devices. If, on the other hand, illumination and collection paths traverse the same optical element, a significant portion of the source energy is inadvertently reflected into the collection fiber without interacting with the sample. This stray light contaminates the measurement and is extremely detrimental. Additionally, the introduction of expanded-beam optical elements complicates the assembly, causes manufacturing difficulties, yields additional variability, and produces other undesirable results.

A special class of devices, termed confocal, involves the utilization of multiple optical elements in conjunction with optical fibers. In these devices, focusing optics create a converging illumination beam which is projected into the operating medium under investigation. The focal point, or point of ray convergence, of the illumination beam lies within the sample. The collection zone is also created with focusing optics and is likewise formed, to the extent possible, concurrent with the illumination zone.

The objective is to create matching focal points of illumination and receptivity projected into the sample medium. The underlying theory is that stimulated light originating at the focal point within the sample is collected from a large solid angle defined by the angle of beam convergence. The intent is to optically re-image the source fiber end face within the sample thereby creating a virtual fiber end face. In theory and assuming 100 percent optical efficiency and no optical distortion, re-imaging the end face as described re-creates the illumination intensity of the actual fiber end face. Although achieving the theory is physically impossible, in a perfectly transparent medium under laboratory conditions, acceptable results is a reasonable goal.

Unfortunately, in the majority of applications in which fiber optic's remote capabilities are highly sought, the materials under investigation are complex, dark, and scattering. The situation is similar to that of the flat face, parallel fiber probe previously analyzed; the converging illumination beam is drastically attenuated and distorted before it effectively reaches the optimum point of receptivity. And for similar reasons, feeble stimulated emissions from this point cannot return to the collector optics.

As a separate disadvantage to this technique, response is collected from a potentially undesirably large sample area since measurement contributions are accumulated, to a certain degree, as the beam converges to its focal point. These devices suffer additional drawbacks including complexity, environmental sensitivity, large size, high expense, and failure in hostile environments. For example, unlike even the flat face, parallel fiber probe previously analyzed, this type of device cannot be inserted into a biomedical catheter.

As a separate consideration, suppose the focal point projecting apparatus is utilized to investigate an undulating mass, such as a heart muscle. As the muscle beats, the tissue moves in relation to the analytical zone. Thus, the measurement is difficult or unsuccessful.

In another approach, a fiber can be bent at its tip in order to point in a direction of interest. For example, one or more flat-faced optical fibers may be directed to view a common or overlapping zone of receptivity. A second group of one or more flat-faced optical fibers may be directed to illuminate the zone. By this method, receptivity and illumination overlap is achieved. Unfortunately, this method suffers from several serious drawbacks. The assembly is expensive and difficult to construct. The ensuing device also lacks repeatability due to manufacturing constraints. If the fibers are gradually bent from their converging orientations to parallel, then the assembly is very large. Even if the fibers are rapidly bent near the assembly's distal end, the assembly is bulky and relatively large in diameter. Such an assembly is much too large to be utilized in an application such as in vivo medical. As the fibers are bent, they become inefficient and lossy at the sharp bend resulting in light escaping from the fiber at this point. In addition, bending the fibers to create a probe results in exceeding the minimum bend limitations for most optical fibers. The fiber is subsequently prone to failure and suffers increased sensitivity to environmental influences.

In another approach, the illumination and collection zones may be manipulated by shaping the fibers' end faces to create a refractive surface. For example, a center fiber may be encircled by a ring of fibers with tapered end faces. This tapering creates a refractive surface on the ring fibers to manipulate their field-of-view inward and toward the center fiber's axis. A key aspect of this refractive-end-face approach is that light manipulation occurs at the fiber end face boundary, and rays are bent as they enter or exit the fiber and cross the boundary of the fiber core end face. Several problems are associated with this approach and limit its effectiveness.

In manipulation of accepted and/or emitted light by the method of forming shaped end faces into optical fibers, the refraction is due to the refractive index differential between the fiber core and the medium surrounding the fiber end face. The extent of refraction is a function of the difference between the two refractive indices and the angular orientation of the light relative to the surface of the interface. Optical fiber cores are typically glass or similar materials with relatively high refractive indices. In order to achieve significant refraction at the fiber end face, it is usually desired to have a gaseous medium, such as air surrounding the fiber end face. This type of medium has a low refractive index thereby facilitating sufficient ray refraction. Most fluids have relatively high refractive indices with values approaching those of common optical fiber core materials. Therefore, media such as fluids, fluid-filled matrix, biological tissue, and melts typically provide insufficient characteristics to achieve the requisite refractive index differential. In addition, shaped end faces typically protrude beyond the protective housing in which the fiber is mounted. This delicate protrusion is susceptible to physical or mechanical damage.

In order to address the dependence on refractive index, the fiber end face must be surrounded by a medium with a known refractive index. The medium is preferably air or a similar gaseous material. This may be accomplished by situating the probe tip behind a window in a sealed chamber. However, use of a window causes numerous problems.

The assembly encompassing fiber, fiber mount, window, window housing, and sealing mechanism is expensive and difficult to construct. The necessity of the sealed chamber also forces substantial increases in the size of the assembly. Thermal expansion and sealing problems also plague the windowed mechanism. The window's optical material possesses low thermal expansion characteristics while the housing to which the window is bound is typically of metal or other high thermal expansion material. Bonding and sealing the window to the metal housing presents numerous difficult engineering challenges.

As light enters or exits the sealed chamber it traverses the window. In many instances, the window material has undesirable spectral characteristics. For example, diamond windows produce strong spectral peaks of Raman scattered light as laser light is transmitted. As a second example, sapphire windows often contain impurities that fluoresce.

The window forces the fiber end face to be removed from the application environment by at least the thickness of the window. Although the window may be only a few millimeters thick, it remains large relative to the size of the fibers. On the optical fiber scale, positioning the fiber tip even this distance from the physical target often correlates to excessive light intensity losses.

For the proper optical performance, the fiber end face should be positioned as close as possible to, and preferably touching, the window. Accomplishing this feat requires a complex means to adjust the distance and lock the assembly in place. As previously described, the shaped end face is mechanically feeble and prone to physical damage. Thus, the assembly is prone to damage not only during positioning but also as a result of thermal expansion, vibration, and general operations.

As the light is incident upon the inner and outer boundaries of the window, it is refracted and reflected. The refracted aspect is either a boon or a hindrance depending on application specifics. The reflection aspects are often highly disadvantageous. For source fibers, window reflections not only weaken the emitted light but also are directed back within the sealed chamber. Depending on configuration and application specifics, these reflections are captured by the source fiber and thereby redirected towards the source. For many applications, this back propagated light is significantly detrimental. The window reflections also tend to interfere with elements adjacent to the optical fiber. For example, a detector fiber positioned in proximity to the source fiber captures a portion of the source light that is back reflected by the window. Light captured in this manner potentially mixes with and contaminates the desirable light. Similar circumstances surround applications in which the shaped end face fiber's principal role is to capture source light generated outside the confines of the fiber. The housing to which the window is fixed, together with the window, forms a sealed chamber. Undesirable light tends to bounce around in this chamber amplifying and exasperating the described stray light problem.

A standard optical fiber, properly mounted in a typical fiber optic connector, withstands tremendous hydrostatic pressure prior to failure. The fiber's small surface area translates even high pressures into very small forces. Thus, extreme pressures are required to generate sufficient force to cause the fiber to piston back into its connector and fail. Conversely, a window is typically much larger in diameter than the fiber positioned behind it. Hence, for a given environmental pressure, the window is subjected to much higher forces than would be an exposed fiber. Additionally, the window is thin and only supported around its outer rim. Therefore, it is susceptible to breakage. Strong, thin windows can be produced from materials such as diamond, sapphire, and similar materials. Unfortunately, these materials not only suffer from the pre-described drawbacks but also have high refractive indices. A high-refractive-index window intensifies the pre-described reflection/refraction problem.

Another drawback to relying on refractive end faces results from the nature of the refractive effect, which limits the extent to which light can be manipulated. This is readily investigated and studied by applying Snell's Law through ray tracing. Due to the nature of refraction, light cannot be aggressively steered off axis to achieve optimal response.

Based on the foregoing discussion, it is highly desirable to redirect light by means other than refraction at the fiber's end face. Specifically, it is desirable to manipulate light within the confines of the fiber assembly's light path. Light manipulation can be accomplished by creating light-shaping structures within the confines of the optical fiber assembly. Thus, light that enters the fiber and would normally be rejected can be redirected for propagation via total internal reflection. Similarly, light propagating via total internal reflection can be directed to otherwise unfeasible paths. By creating the light-shaping artifices within the confines of the fiber assembly's internal structure, effects similar to those found in fibers with shaped end faces are produced without the disadvantages or constraints associated with shaped end faces.

One method of achieving light bending within the confines of the optical fiber is to include a light-manipulating surface between two adjoining waveguide sections. This can be accomplished by inserting a light-altering component between two sections of fiber. A highly advantageous method is to construct the light-shaping artifice into or onto the fiber end face that adjoins another fiber segment or section. For example, light-shaping contours are readily constructed into a fiber end face that is butted to a second fiber. The second, adjoining fiber end face can be flat faced or also encompass light-altering surfaces or characteristics. As an alternative to light-shaping by refraction, the light shaping can occur via diffraction, reflection, scattering, interference, or other methodology. If light-shaping refractive surfaces are employed which are not symmetrical about the fiber's central axis, the light tends to be steered or bent off-axis. Thereby, illumination and/or collection zones are directed off-axis.

A second method of achieving light manipulation and bending within the confines of the optical fiber is based upon reflection. In this method, the fiber core's exterior surface is modified to create a reflective surface other than the standard core-cladding interface. For example, an optical fiber whose end face is formed into a sharply inclined planar surface will exhibit these characteristics. Suppose the angular inclination of the end face is sufficiently inclined to generate a totally internally reflective internal surface. As light propagates within the fiber core towards this distal tip, it encounters the special surface. The propagating light is re-directed by total internal reflection to exit the fiber through its side or outer cylindrical surface. Variations on this theme include creation of surface contours which do not typically yield total internal reflection but to which internally reflective coatings are applied. Additionally, various complex contours can be generated which mix various optical effects.

Another method for fiber optic light manipulation entails forming a group of flat-faced optictal fibers consisting of illuminating source and collection fibers. A typical orientation is a single source fiber surrounded by a ring of collection fibers. This grouping of fibers is butted up to a single, large-core optical fiber. The single fiber's large core has a diameter equal to or greater than the collective grouping of smaller fibers. The large-core fiber is utilized in a bi-directional capacity. Its distal end both delivers illuminating energy and captures target light. This method suffers from several drawbacks. A certain degree of source light is reflected from the fiber's end face before the light exits the fiber. This light is prone to back propagation within the large core fiber and returns to the collection fibers as stray light. Secondly, as the source light traverses the large-core fiber segment, detrimental signals are often generated. For example, Raman-scattered light is produced and radiates in all directions. Unfortunately, the large-core fiber accumulates the Raman-scattered light and efficiently waveguides it to the collection fibers where it is mixed with the desired target light. Fluorescence generated within the large-core fiber is likewise delivered to the collection fibers and corrupts the measurement process.

Therefore, there is a need in the art for an improved fiber optic probe assembly that allows effective and efficient manipulation of the light delivery and reception regions. The light manipulation should take place within the fiber assembly's light path and should allow significant off-axis steering of the fibers' viewing areas. The probe assembly should be compact and easy to manufacture, and should not rely on expanded optics and other complicated features found in the prior art.

SUMMARY OF THE INVENTION

The present invention satisfies the above-described need by providing an improved method and apparatus for fiber optic light management. The invention provides a number of novel fiber optic light manipulation and management techniques, which are individually important for diverse fiber optic applications. For example, the present invention provides an improved fiber optic probe assembly for low-light spectrographic analysis. The invention improves response to subtle light-matter interactions of high analytical importance and reduces sensitivity to otherwise dominant effects, thereby overcoming the technical difficulties associated with light-based characterization in complex media. This is accomplished by adjusting the illumination and collection fields of view in order to optimize the probe's sensitivity. Light manipulation is applied internal to the fiber so that the probe's delivery pattern and field of view do not require external manipulation and are not adversely affected by investigated media. This allows the light delivery pattern or field of view or both to be aggressively and reliably steered off-axis to achieve significant increased performance levels. Aggressive beam steering is accomplished by employing internally reflective surfaces in the fiber. A reflective metal coating or a low refractive index coating or encapsulant can be used to ensure total internal reflection. The fibers also incorporate filters, cross-talk inhibitors and other features that provide a high performance probe in a robust package. Design variations provide side viewing, viewing through a common aperture, viewing along a common axis, and other features.

Generally described, the present invention provides a probe having selective sensitivity to specific photon-matter interactions. This selective sensitivity is achieved by delivering light at one angle and collecting light at the appropriate angle to maximize the response. The delivery and collection paths are re-directed off-axis to intersect with one another at specific angles while the delivery and collection fibers remain in close proximity to one another.

In another aspect, the present invention provides a means for segregating inelastic and elastic photon-matter responses of a material by angularly manipulating the delivery and collection patterns in relation to one another. The elastic response is directionally biased such that its collection, in relation to the inelastic response, is minimized.

In another aspect, the present invention provides a fiber with a tip having a portion that is internally reflective and a portion that is internally non-reflective. The reflective portion of the tip delivers light at angular orientations beyond the fiber's normal propagation limits. Incoming light, incident on the reflective surface, is angularly steered, so that light is received at angular orientations beyond the fiber's normal propagation limits.

More particularly described, the internally reflective portion may be the result of an internally reflective coating, or may be essentially total internal reflection. Total internal reflection may be induced by placing a low refractive index material into contact with the fiber. The low refractive index material may include a low index coat or encapsulant, or the ambient medium. The internally reflective surface may include a variety of shapes, which can be used to control the field of view with great precision.

In another aspect, the present invention provides a probe that incorporates a reflective surface for steering the light path. The probe includes at least one delivery fiber and at least one collection fiber. The delivery fiber or collection fiber include an internally reflective surface for causing the light delivery path and light collection path to converge.

In another aspect, the present invention provides a probe assembly that includes filters applied directly to the interior end faces of distal fiber segments.

In another aspect, the present invention provides a method for mass producing fibers with high performance filters.

In another aspect, the present invention provides a fiber optic probe that collects light directly in front of, or at, the delivery aperture. The viewing angle is directed in response to the extent of the elastic response, the strength of the inelastic response, the desired depth of investigation, and the absorption of the medium.

In another aspect, the present invention provides a probe comprising a plurality of fibers essentially parallel to each other and in close proximity to one another. The coupling efficiency between the probe and the investigative medium is enhanced by fusing the bundle of collection and delivery fibers together. The fusing process entails heating the fibers and compressing the fibers so that no gap exists.

In another aspect, the present invention provides a means of optically isolating two or more fibers that are in close proximity to each other, such that the signals from each fiber do not mix. A light impenetrable barrier is stationed between the fibers in the area prone to cross talk.

In another aspect, the present invention provides an optical fiber enhanced at its tip to collect or deliver light beyond the fiber's normal limits of propagation. The fiber adjoins another short fiber segment. The short fiber shuttles light between the beam-steered fiber end face and the distal end face of the assembly. The short fiber segment has the ability to carry angularly oriented light beyond that of the unmodified, primary fiber.

In another aspect, the present invention provides a fiber optic probe assembly that includes a central fiber and a plurality of fibers surrounding the central fiber. The central fiber has a flat end face at its distal end. The plurality of fibers surrounding the central fiber and have shaped end faces at their distal ends. The plurality of fibers are parallel to the central fiber at their distal ends. The shaped end faces provide an internally reflective surface for steering the fields of view associated with the plurality of fibers toward the central fiber.

The present invention also provides a fiber optic probe assembly that includes a first fiber and a second fiber. The first fiber includes an end face having a first shape. The second fiber includes an end face having a second shape. The first and second fibers are parallel to each other at their end faces. The second shape provides an internally reflective surface for directing the field of view associated with the second fiber toward the first fiber.

In another aspect, the present invention provides a fiber optic assembly having a common axis for delivering and collecting light. The assembly includes a light delivering fiber and a light collecting fiber. The light delivering fiber has a filter at its end face. The light collecting fiber has a reflector at its end face and is mounted parallel to the light delivery fiber. The first filter is operative to reflect delivered light through its side wall and to allow collected light to pass through to the light collecting fiber. The collecting fiber reflector directs light along the axis of the light collecting filter.

Alternatively, the present invention provides a fiber optic assembly having a common axis for delivering and collecting light. The assembly includes a light delivery fiber and a light collecting fiber. The light delivering fiber has a filter at its end face. The light collecting fiber has a reflector at its end face and is mounted parallel to the light delivery fiber. The filter is operative to pass delivered light and to reflect collected light to the reflector on the collection fiber. The reflector directs collected light along the axis of the light collecting filter.

In another aspect, the present invention provides a fiber optic probe assembly using a common aperture for delivering and collecting light. This is achieved by transmitting desirable light through a fiber's sidewalls. The assembly includes a central fiber having a flat end face at its distal end and a plurality of fibers surrounding the central fiber. The plurality of fibers have a shaped end face at their distal ends.

The plurality of fibers are parallel to the central fiber at their distal ends. The shaped end faces provide an internally reflective surface for steering the fields of view associated with the plurality of fibers through the side wall of the plurality of fibers and through the end face of the central fiber.

In another aspect, the present invention provides a fiber optic probe assembly for side delivery and collection of light. The assembly includes a first fiber and a second fiber. The first fiber has a shaped first end face. The second fiber has a shaped second end face and is parallel to the first fiber. The shaped first end face and the shaped second end face direct light toward a common region.

In yet another aspect, the present invention provides a method for fabricating a fiber optic probe assembly. The method includes forming a bundle of fibers including a center fiber surrounded by a ring of fibers. The bundle of fibers is bound together. A cross-talk inhibitor mechanism is incorporated into the probe. The bundle of fibers is shaped to form a pencil tip or cone. The cone is then flattened so that the center fiber has a flat end face.

In another aspect, the present invention provides a fiber optic probe that incorporates an integral reference material. The probe includes fibers for delivering light to an investigative site and fibers for collecting light from an investigative site. In addition to exciting a response from the medium under investigation, the delivered light excites a response from the reference material. The light from the reference material maybe collected and used to calibrate the system, compensate for drift, establish accuracy, and verify functionality.

In another aspect, the present invention provides a means for manufacturing low cost, high performance probes for inclusion in a comprehensive analytical system. The probes are disposable following their utilization.

The various aspects of the present invention may be more clearly understood and appreciated from a review of the following detailed description of the disclosed embodiments and by reference to the appended drawings and claims.

BRIEF DESCRIPTION OF THE DRAWINGS

FIG. 1 is an isometric view of a flat face optical fiber.

FIG. 2 is an isometric view of a fiber having a planar, angled end face.

FIG. 3, consisting of FIGS. 3a and 3b, illustrates a fiber having a cone-shaped end face, with the axis of the cone displaced from the fiber's center and the cone point outside the fiber.

FIG. 4 is an isometric view of a fiber having a cone-shaped end face, with the axis of the cone displaced from the fiber's center and the cone point within the fiber.

FIG. 5 is a cross sectional view of a fiber having a partial bevel applied to its flat end face.

FIG. 6 is a isometric view of the partially beveled flat face fiber of FIG. 5.

FIG. 7, consisting of FIGS. 7a–c, illustrates a fiber having a complex sectional contour.

FIG. 8 is an isometric view of a fiber having a complex sectional contour.

FIG. 9 is a cross-sectional view illustrating the illumination zone of a fiber having a partially beveled flat end face.

FIG. 10 is a cross-sectional view illustrating the illumination zone of a fiber having a partially contoured flat end face.

FIG. 11 is a cross-sectional view of a fiber configured to direct light through the fiber's side.

FIG. 12 is a cross-sectional view of a fiber configured to refract some light at the end face and direct other light through the fiber's side .

FIG. 13 is a cross-sectional view of a fiber with a curved end face.

FIG. 14 is a cross-sectional view of a fiber assembly including two fiber segments with adjoining end faces.

FIG. 15 is a cross-sectional view of a fiber assembly including two fiber segments with shaped adjoining end faces.

FIG. 16 is a cross-sectional view of a fiber assembly in which an optical element is inserted between two fiber segments.

FIG. 17 is a cross-sectional view of a fiber assembly in which a large diameter segment is coupled to a small-diameter fiber segment.

FIG. 18 is a cross-sectional view of a fiber assembly in which a large diameter segment is coupled to a small-diameter fiber segment.

FIG. 19 illustrates light manipulation via traditional mirrors.

FIG. 20 illustrates light manipulation through a short segment of a large-core fiber.

FIG. 21 illustrates light manipulation through an unconventional fiber.

FIG. 22 illustrates light manipulation through a hollow fiber.

FIG. 23 is a cross-sectional view of a fiber assembly that employs a small-core primary delivery fiber and a large-core distal segment.

FIG. 24 illustrates an index optical fiber positioned behind a short segment of a gradient index fiber.

FIG. 25 illustrates the fabrication of a non-axially symmetric, gradient index fiber segment by means of core drilling a common gradient index lens.

FIG. 26 illustrates a off-axis beam steering gradient index fiber segment joined to a primary optical fiber.

FIG. 27, consisting of FIGS. 27a–c, illustrates a light-scattering probe constructed in accordance with the present invention.

FIG. 28 is a graph illustrating the spectra acquired by three probes in a blood sample containing a fluorescent aspect.

FIG. 29 is an enlarged portion of the graph of FIG. 28.

FIG. 30 is a graph illustrating the results of probe tests conducted on an aqueous-based, red solution with minimum particulate scattering characteristics.

FIG. 31 is a graph of the spectra collected in a red light scattering medium.

FIG. 32 is a graph of the spectra collected in a red light scattering medium with trace yellow-green fluorescent additive.

FIG. 33 is a top view of a probe assembly that employs a tightly packed, fused bundle of fibers.

FIG. 34 illustrates bundle being fed into a single, large-core fiber.

FIG. 35 depicts a probe assembly that is adapted for filter application.

FIG. 36 illustrates a fiber assembly in which the center fiber extends further into the test medium.

FIG. 37, consisting of FIGS. 37a and 37b, illustrates a probe assembly in which the collection fiber is larger then the delivery fiber.

FIG. 38, consisting of FIGS. 38a–h, illustrate various arrangements for projecting light in front of and parallel to collection fibers.

FIG. 39, consisting of FIGS. 39a and 39b, illustrates attachments that may be attached to the end of a fiber bundle.

FIG. 40, consisting of FIGS. 40a and 40b, illustrates a fiber assembly in which the ring fibers are diametrically separated from the center fiber.

FIG. 41 illustrates a fiber assembly in which the ring fibers are shaped to be fully internally reflective.

FIG. 42 is an isometric view of the fiber assembly of FIG. 41.

FIG. 43 illustrates a fiber assembly where the ring fibers have a longer bevel.

FIG. 44 depicts a fiber configuration in which thick-wall capillary tubing is utilized.

FIG. 45 depicts a configuration in which the center fiber is formed to create an internally reflective surface.

FIG. 46 depicts a configuration that is adapted for high sensitivity directly at the probe tip.

FIG. 47 depicts a convex element adjoining delivery and collection fibers in which reflections from the outer surface of the element are directed back into the source fiber.

FIG. 48 illustrates the light interaction associated with a scattering powder.

FIG. 49, consisting of FIGS. 49a–d, depicts two configurations in which a source fiber's illumination is directed over a single collection fiber.

FIG. 50, consisting of FIGS. 50a–d, depicts various cut-away and perspective views of an assembly which includes an optical end piece producing the requisite internal reflection.

FIG. 51, consisting of FIGS. 51a and 51b, depicts a configuration in which source light is projected through a gap between adjacent fibers.

FIG. 52, consisting of FIGS. 52a and 52b, depicts a fiber optic probe utilizing gradient index optics to bend illumination from source fibers to coincide with the field of receptivity of collection fibers.

FIG. 53, consisting of FIGS. 53a and 53b, depicts elements in which a hole is drilled and the center fiber is inserted.

FIG. 54 depicts a cross section of a probe with a center fiber surrounded by a ring of fibers.

FIG. 55, consisting of FIGS. 55a–f, depicts various aspects of probes employing light-manipulating artifices between adjoining fiber segments.

FIG. 56, consisting of FIGS. 56a and 56b, illustrates cross sectional and perspective views of a similar assembly which utilizes an end piece to create similar performance results.

FIG. 58 depicts a method of enhancing overlap between the source fiber's delivery beam and the collection fiber's zone of receptivity.

FIG. 59 illustrates a single fiber with improved performance characteristics.

FIG. 60 provides a perspective view of a complete termination assembly.

FIG. 61 illustrates an exemplary probe for delivering and collecting light along a common axis.

FIG. 62 illustrates a probe in which light enters and leaves the probe along a common axis and essentially parallel with the fibers' axes.

FIG. 63 is a cross-sectional view of a probe assembly having a common delivery and collection aperture.

FIG. 64 illustrates a two-fiber configuration in which the delivery fiber has a curved internally reflective surface.

FIG. 65 details a distal tip incorporating a large number of optical fibers and in which the collection fibers are responsive to light at diverse angular orientations.

FIG. 66 presents an embodiment in which the outer end faces are contoured to form refractive end faces and light purposely travels through the fiber sidewalls.

FIG. 67 depicts an alternate embodiment whose fibers have individually concurrent optical and mechanical axes these axes collectively intersecting one another and light purposely travels through the fiber sidewalls.

FIG. 68 depicts an embodiment which incorporates an internally reflective optical element in conjunction with the fiber bundle resulting in a common delivery and collection aperture.

FIG. 69 depicts an embodiment which utilizes gradient index optics for beam steering and light purposely travels through the fiber sidewalls.

FIG. 70 depicts an embodiment in which the center fiber end face is shaped for light manipulation and light purposely travels through the fiber sidewalls.

FIG. 71, consisting of FIGS. 71a and 71b, depicts a side delivery/viewing two-fiber probe that utilizes an off-axis, parabolic surface contour for internal reflection.

FIG. 72, consisting of FIGS. 72a and 72b, depicts a side delivery/viewing probe that projects the collection pattern through the delivery fiber.

FIG. 73 depicts a side delivery/viewing probe that utilizes a bundle of fused fibers for collection and a single, small fiber for light delivery.

FIG. 74 provides an expanded view of the internally reflective shaped surface and light pattern as it relates to fabrication tooling and parameters.

FIG. 75 illustrates a probe manufacturing fixture in which fibers are fixed to a mandrel.

FIG. 76 illustrates the relationship between tooling fabrication geometry and resulting optical parameters.

FIG. 77 depicts a side delivery/viewing embodiment that utilizes gradient index optics for beam steering.

FIG. 78 depicts a side delivery/viewing embodiment that utilizes an internally reflective end piece.

FIG. 79 illustrates a tooling apparatus suitable for applying filters to fiber end faces.

FIG. 80 illustrates filters applied to fibers having cone-shaped end faces.

FIG. 81 illustrates a fiber device that separates light according to wavelength.

FIG. 82 depicts a filtered probe with fibers whose mechanical and optical axes intersect at a distance beyond the distal tip of the probe.

FIG. 83 depicts a filtered probe with fibers whose mechanical and optical axes intersect at a distance beyond the distal tip of the probe.

FIG. 84 illustrates a waveguided cell for analysis of a fluid.

FIG. 85 illustrates a cell for analysis that does not rely on optical fibers.

FIG. 86 illustrates a non-fiber-coupled waveguided cell for analysis of inelastic light-matter interactions.

FIG. 87 illustrates a waveguided cell for low-concentration analysis of chemicals.

FIG. 88 depicts a probe in which only the inelastic light resonates within a cavity.

DETAILED DESCRIPTION

Figure 57A:
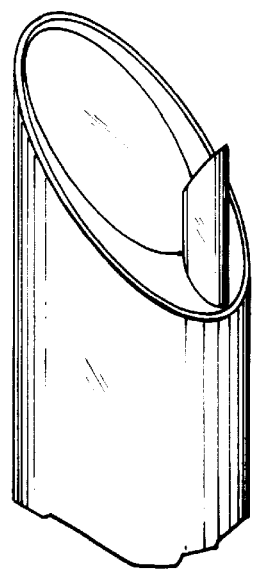
FIG. 57, consisting of FIGS. 57a–f, depicts a probe'configuration that employs a variety of light manipulation techniques.

The present invention is directed to an improved fiber optic probe assembly with manipulated delivery and reception sensitivities. In an exemplary embodiment, the invention is incorporated into fiber optic probes that employ the "GASER" light management system. This system incorporates a number of novel fiber optic light manipulation and management methods which are described herein. Each of these methods is individually important for diverse fiber optic applications spanning from telecommunications to high power laser delivery. Nevertheless, they are described in terms from this perspective, the selection and utility of each method for this application is taught. And, the strategies of combining methods for an integrated solution is developed. Such probes are manufactured and sold by Visionex, Inc., of Warner Robins, Ga. Briefly described, a fiber-optic probe in accordance with the present invention provides selective sensitivity for capturing disproportionate responses associated with specific light-matter interactions. Light manipulation techniques are applied internal to the fiber in order to allow the illumination and collection zones to be altered for specific light-matter interactions. Probe performance is enhanced by applying filters to fiber segments, isolating the fibers that form the probe tip, and fusing the fibers together to make them as close as possible.

Referring now to the drawings, in which like numerals represent like elements throughout the several figures, aspects of the present invention will be described. The relative sizes of some components, such as filters, cladding, coatings, and the like, are exaggerated for illustrative purposes.

OPTICAL FIBERS IN GENERAL

The term "optical fiber" is used herein to refer generally to any optical waveguide or structure having the ability to transmit the flow of radiant energy along a path parallel to its axis and to contain the energy within or adjacent to its surface. "Step index," "gradient index," and "single mode" fibers are subcategories within the optical fiber designation. The term "multimode" optical fiber refers to an optical waveguide that will allow more than one bound mode to propagate.

Step index fibers include a transparent cylindrical core of relatively high refractive index light-conducting material. Typical core materials include silica, plastic, and glass. The core is cylindrically surrounded by a medium having a lower refractive index. Typically, this medium is a relatively thin cladding, which is an intimately bound layer surrounding the core. The cladding may be a different material than the core, or it may be a similar material that has been doped in order to reduce its refractive index. The core may also be unclad whereby the ambient medium, often air, is of lower refractive index and acts in the capacity of the cladding. The cladding is usually surrounded by one or more coatings, buffers, and/or jackets that primarily serve protective roles.

An arbitrarily oriented ray within the core of a step index fiber travels until it intersects the core boundary at the cladding and interacts in accordance with its angle of incidence. Generally, rays angularly oriented close to parallel with the fibers axis are efficiently reflected at the core boundary. Within certain angular limitations, the ray is oriented to undergo total internal reflection at the core interface. These angular limitations are a function of the refractive indices of the core and the cladding. The limits determine the angular bounds within which the fiber can propagate light. Thus, sustained propagation occurs via repeated total internal reflection within the fiber core. If the arbitrary ray is oriented beyond the fiber's limits for total internal reflection, then only a fraction of its intensity is internally reflected. The reduced intensity ray is further attenuated as it undergoes subsequent core-boundary interactions. The ratio of light energy that is internally reflected to the energy that escapes varies according to the angle. If the ray is oriented normal to the core boundary, then all of its intensity is lost. As the angle of an improperly oriented ray approaches the acceptance limits for total internal reflection, the relative intensity of the reflected ray increases. Thus, for rays with angle orientation close to, but outside of, the limits for total internal reflection, multiple reflections can occur prior to significant power loss.

If the arbitrarily oriented ray within the fiber core has sufficient power and orientation, then it sustains power and eventually reaches the fiber end face. It interacts with the end face boundary in accordance with the laws of reflection and refraction. As the ray crosses the end face boundary between the fiber's core and the surrounding medium, it is refracted. The refractive effect is a function of the refractive index of the core, the refractive index of the surrounding medium, and the orientation of the ray relative to the fiber end face surface. The factor of ray orientation is based upon its angle relative to a surface normal taken at the point where the ray intersects with the end face surface boundary. Angular orientation of rays outside the fiber end face and propagating rays within the fiber core are distinctly correlated. Thereby, a correlation exists between individual and collective external and internal rays.

The previous discussion centered on rays internally propagating and exiting the fiber. An analogous situation exists for rays outside the optical fiber entering into the fiber core. The correlating development is readily drawn by those skilled in the art. For a fiber utilized for single-direction flow of light, light is typically injected into the fiber at one end and exits the fiber at the opposite end. However, fibers can also be utilized in a bi-directional configuration. In this configuration, light purposely enters and exits from a single end of the fiber.

As light propagates within the fiber core, it tends to become mixed or randomly oriented over distance. Even highly directional sources, such as lasers, become mixed or scrambled over distance following input into a long optical fiber. In this mixing process, the fiber's modes are filled and all source characteristics, or so-called launch conditions, are lost. The mixing process can be accomplished in shorter fibers by tightly coiling the fiber, inducing micro-bends, or otherwise stressing the fiber. Similarly, for very short fiber lengths, launch characteristics are retained. Also, for very short lengths of fiber, light can be transmitted beyond the normal limits for propagation dictated by the angular limits for total internal reflection. This property is due to the reduced number of reflections, which accumulate minimal attenuation. A fiber's ability to sustain transmission beyond the normal limits for total internal reflection can be enhanced by the application of internally reflective coatings applied to the fiber's outer cylindrical surface. This coating can be applied to either the fiber's core or the cladding. It should be noted that for long fibers, propagation cannot be totally reliant on reflective coatings. In contrast to total internal reflection, even the best reflective coatings offer less than 100 percent reflectivity. Losses associated with repeated reflections at less than 100 percent efficiency quickly accumulate resulting in severe attenuation. Vast numbers of reflections occur during propagation in even moderate fiber lengths.

AN IMPROVED PROBE ASSEMBLY

A probe constructed in accordance with the present invention allows light emergence and collection patterns to be manipulated and controlled in highly advantageous manners. The light manipulation occurs internal to the assembly and within the normal path of light propagation in the assembly. Thus, illumination and collection zones are manipulated and directed without utilizing refractive influences at the point of light entering or exiting the assembly as the primary control mechanism. However, refractive influences typically remain as light enters or exits the assembly and may be used as a supplemental means of light manipulation. Incoming light undergoes the desirable manipulation following entering the fiber assembly and passing the point of fiber boundary refraction. Likewise, light leaving the fiber assembly is manipulated prior to passing the confines of the assembly and the final fiber interface, where it is potentially refracted.

METHODS OF MANIPULATING LIGHT WITHIN A FIBER

FIG. 1 provides a view of a general, flat faced optical fiber 100. The end face 105, core 110, cladding 115, and coating 120 are shown. FIGS. 2, 3, and 4 depict optical fibers with various contoured end faces. The fiber 200 of FIG. 2 has a planar, angled end face 205. The fiber 300 of FIGS. 3a and 3b has an end face 305 that is shaped like a cone with the axis displaced from the center of the fiber and with an imaginary cone point outside the fiber. The fiber 400 of FIG. 4 has an end face 405 shaped like a cone with the axis displaced from the fiber's center, but with the cone point within the fiber cross section. More complex end faces, such as aspheric shapes, are also possible. Examples of end face contours include, but are not limited to, convex radiused, concave radiused, parabolic, hyperbolic, tapered, and cylindrical.

It is also possible to create fibers with end face forms that cannot be readily characterized as a single shape. For example, a partial bevel may be applied to a flat faced fiber. Thus, a fiber may be created whose face is flat on one side and planar angled on the other. FIGS. 5 and 6 are cross sectional and isometric views of such a fiber.

Generally speaking, a fiber end face can be created in which a section of the end face is characterized as one geometric form and another section of the end face is characterized as a second geometric form. The piece-wise contours may be employed to approximate a more complex contour. For example, multiple angled sections are formed to approximate a radiused, or spherical, shape. As a second, more important utilization, each surface area may perform distinct optical functions. In this manner, advantageous optical characteristics are created.

FIGS. 7 and 8 depict fibers with sectional contours whose shapes are more complex than planar. The end face geometry is created by first creating a complex end face contour and then flattening the tip through grinding and polishing operations. In the depicted shapes, the non-flat section has convex characteristics. In FIG. 8, the non-flat region is geometrically a section of a cone side. In FIG. 7, the non-flat region is geometrically a section of a paraboloid of revolution.

FIG. 9 depicts a representative illumination pattern from a fiber 905 with an internally reflective simple bevel, such as the fiber of FIG. 6. Two distinct illumination zones are created. A first illumination zone 910 is typical of optical fibers. A second illumination zone 915 is created by internal reflection from the angled surface 920. In the second illumination zone 915, a prismatic surface is created at the fiber core's outer boundary.

FIG. 10 depicts a representative illumination pattern from a fiber 1005 having an internally reflective complex contour 1010 in addition to the flat portion 1015. The properly created contour delivers light at precisely controlled angles. The contour 1010 is created such that light rays striking its internal surface are directed to exit the fiber at desirable angles per application requirements. Thus, precision controlled illumination patterns are created. Additionally, the light need not exit through a planar area of the fiber's end face; it can exit through the fiber's side at a desirable angle. FIG. 11 depicts a configuration that accomplishes this goal.

As previously described, standard optical fibers' flat end faces induce refraction as light rays cross the boundary between the fiber core and surrounding medium. The refractive effect bends the light rays. Contoured end faces produce a refractive effect on light rays passing through the end face. It is this refractive effect on which the contoured end face typically operates and upon which its design is based. However, an optical fiber end face also produces a reflective effect as a result of the refractive index boundary. As an arbitrary ray intersects the contoured fiber's end face boundary, a reflected ray is typically generated. The angle of ray reflection equals the angle of ray incidence upon the fiber end face. For minor angles of incidence, the reflected ray is weak relative to the strength of the incident ray. Depending on the geometry, the reflected rays are back propagated by the fiber.

A fiber end face may be formed to create a surface for total internal reflection. For example, light propagating within the fiber and towards the fiber end face, is directed out the fiber's side by an appropriately angled, planar end face. FIG. 11 presents a cross sectional view of such a fiber 1100. The extent and characteristics of total internal reflection are functions of light ray angle relative to the surface encountered. Optical fibers typically propagate light of various angular orientations; therefore, a contour may transmit and refract certain angularly oriented propagating rays while producing total internal reflection for others. For example, it is possible to angle a planar end face such that a portion of the propagating rays are refracted while others are reflected. FIG. 12 presents a cross sectional view of such an optical fiber.

In addition to the factor of ray orientation, certain fiber face contours create refraction and reflection according to ray placement on the fiber end face. For example, a hyperbolic end face might be totally internally reflective around the outer radial portion of the core and refractive near the fiber center. FIG. 13, although not hyperbolic, depicts such a fiber end face. A similar situation exists for fibers whose end faces are sectionally contoured. The previously referenced example of a fiber whose end face is partially beveled and partially flat exhibits these characteristics if the bevel is sufficiently angled. FIGS. 5 and 6 depict this type of fiber and the related light rays. Referring to FIGS. 7 and 8, the convex aspects of the reflective section adds a focusing effect to the projected light receptivity/delivery zone.

As stated earlier, total internal reflection is a function of the ray's angle of incidence upon the surface boundary. A second condition requires the external medium to have a sufficiently lower refractive index than the inner medium. Thus, if a properly beveled fiber end face is positioned in air, or similar media, total internal reflection is produced as depicted in FIG. 11. Nevertheless, it is also possible to generate total internal reflection without an air interface. By surrounding the total internally reflective surface with an intimately bound medium such as low-index fluoropolymer, appropriate optical conditions are generated. This technique produces mechanically robust components capable of bearing physical abuse. With the described intimately bound material, the total internal reflection occurs independent of the refractive index of the application medium. Thus, the assembly may be utilized in high-index liquids and other high-index media. The ensuing assembly technique has the additional benefit of allowing for secondary grinding and polishing operations to create additional optical surfaces.

Even without coatings and barriers, sufficient refractive index differences are achievable between fiber and many liquid media. For example, with the proper angle, total internal reflection is readily achieved for silica fibers in aqueous media. Fibers constructed of higher index materials, such as sapphire, achieve total internal reflection with less restrictive angle and in even higher index media.

In certain materials, the refractive index is affected by transmitted optical energy. Optical elements constructed of these materials are sometimes referred to as nonlinear optics. By utilizing these materials as the medium contacting the fiber's special internally reflective surface, an optical switch or beam steering mechanism is created. The medium's refractive index should be close to the threshold for total internal reflection. By subjecting the medium to controlled dosages of optical energy, total internal reflection is manipulated as the medium's refractive index changes.

For internal reflection at angles beyond the total internal reflection limits, reflective coatings can be applied to the fiber end faces. As with the previously described example involving application of bonded low-index materials, secondary grinding and polishing operations prove useful. These operations provide an entry/exit sector for light and facilitate the creation of various secondary contours. Additionally, in many instances, the reflective coating reduces wavelength sensitivity since for most materials refractive index is a function of wavelength.

Following formation of the fiber's principal end face, the fiber is coated with internally reflective material such as aluminum or silver. For applications in chemically aggressive or high-temperature environments, platinum, rhodium, and gold coatings are less sensitive to degradation. The fiber end face is then encapsulated in material, such as epoxy, providing strength and mechanical integrity. Next, the assembly is ground and polished to expose the fiber and create a flat section at the fiber center. Thus, light of specific angular orientations enter and leave the fiber through this exposed section. The fiber can be utilized directly in liquids and other high-index media. Light manipulation occurs independently of any refraction occurring as light crosses the boundary between the fiber and the surrounding medium. Depending on the refractive index of the ambient medium, refraction at the final exit port may be inconsequential. It is readily seen that the aforementioned techniques are easily utilized to create many desirous effects. For example, contours are created in which light is readily directed off the fiber's axis.

To generate a surface contour to accomplish a specific light manipulation goal, ray tracing mathematical procedures are undertaken. Although many variations on this theme are possible, the following example illustrates a procedure for a simple first order approximation. This type of procedure is often referred to as a finite element analysis and is readily undertaken via computer programming. The fiber is first sectioned, end-on, into analytical regions. A desirable illumination pattern specifying angle of illumination and point of illumination escape is established as a goal. Each analytical region is separately analyzed to establish acceptable contour boundaries. Next, additional constraints are added, which may include manufacturability, continuity between neighboring regions, and other factors. The final illumination is the summation of the contribution from each analytical region. Since a typical net illumination goal may encompass various angles of illumination at various strengths, additional manipulation of regional contours may be required to achieve the overall goal.

FIG. 14 represents a fiber assembly 1400 comprising two fiber segments 1405, 1410 with adjoining end faces. One of the adjoining fiber end faces is shaped into a cone. This allows the shaped end face's light manipulating properties to be transferred to the flat distal end face. Filters and/or filter coatings are readily applied. Although the depicted embodiments utilize step index fiber segments, either or both of the segments may be constructed of gradient index fibers. An in-depth discussion of this technology and art is presented in U.S. Pat. No. 5,764,840, entitled "Optical Fiber with Enhanced Light Collection and Illumination and Having Highly Controlled Emission and Acceptance Patterns," filed, which is assigned to the assignee of the present invention, and which is incorporated by reference.

FIG. 15 represents a similar fiber assembly 1500 comprising two fiber segments 1505, 1510 with adjoining end faces. In this assembly, contoured end faces are formed into both adjoining end faces. Light manipulation is accomplished gradually as light is refracted across both fiber end faces. Additionally, the end face surfaces are not symmetric about the fiber's central axis. The axial bias of the contours directs the light rays off the fiber's axis. As with the previous example, the light manipulation is transferred down the short fiber to the distal tip. The alternate distal end face, depicted in dashed lines, is created to enhance the optical characteristics. This end face is depicted as angled planar and produces several desirable properties. Since the effective aperture for light acceptance/admittance is increased, placement sensitivity of final fiber sidewall reflection is reduced so that the length tolerance of the distal fiber segment is maximized. Since light rays pass through the final fiber end face closer to perpendicular than for a standard fiber end face, the refractive influences of the distal fiber interface is minimized. The importance of this factor is dependent upon the refractive index of the application medium and the desirable effects. And, the end face protrudes further into the application medium than would a normal, flat end face. The fiber protrusion extends farther into the application environment and thus presents the opportunity for precision manipulation, delivery, and acceptance in a scattering or absorbing medium. Although the protrusion of the fiber end face might appear small and insignificant, closer analysis reveals that on the optical fiber scale, this distance is significant in many circumstances.

FIG. 16 depicts a fiber assembly 1600 in which an optical element 1605 is inserted between two fiber segments 1610, 1615 producing the desirable light manipulation. The optical element 1605 may be refractive, reflective, diffractive, interference-based, or even based on holography, light-scattering agents, or other optical mechanisms. As in the previous example, filter elements are readily applied to the appropriate surfaces or added as distinct elements. The light controlling element can also be molded into the fiber such that it is an integral component of the optical fiber.

FIGS. 17 and 18 depict two assemblies 1700, 1800 in which large-diameter fiber segments 1705, 1805 are coupled to small-diameter fiber segments 1710, 1810. In the described manner, desirable effects are readily created. For example, it is possible to transfer light from the larger fiber into the smaller fiber. Thus, light intensity is increased. The previous statements related to the delivery and transmission of the manipulated light are relevant in this scenario.

FIG. 19 depicts the transfer of light manipulation via traditional mirrors. Although not shown, prisms are readily utilized in a similar fashion. In either case, the flat reflective surfaces maintain delivery/receptivity pattern integrity as the light manipulation is transferred. FIG. 20 depicts the transfer of light manipulation through a very short segment of large-core fiber. FIG. 21 depicts similar transfer of light manipulation through a non-conventional fiber. In this case, the fiber is an unclad waveguide. As the reflective surfaces of the waveguide approach flat planar geometries, convolution of the manipulated light is reduced within the transfer path. Although depicted straight, the waveguide may be permanently bent. FIG. 22 depicts transfer of light manipulation through the application of a hollow optical fiber.

FIG. 23 depicts an assembly 2300 configured with a number of advantageous attributes. The primary delivery fiber 2305 is a small-core, low numerical aperture fiber. This fiber is butted to a distal segment of large-core, step index fiber 2310. The distal segment 2310 utilizes a high numerical aperture fiber to better contain the light. Additionally, to enhance light containment, the fiber's exterior may be coated with internally reflective material such as vapor-deposited aluminum. The distal segment 2310 has a light-shaping contour 2315 formed into its end face adjoining the primary delivery fiber. The light-shaping contour 2315 is formed to steer the light off-axis. The non-active, protruding portion of the contour is removed to minimize the distance between end faces of the two fiber segments.

Although this embodiment features a light-shaping contour in only one of the adjoining end faces, both end faces can be so formed. In doing so, the light manipulation is distributed over two surfaces thereby creating the opportunity for additional manipulation and higher transfer efficiency.

The primary delivery fiber's diameter is increased at the fiber junction by fixing a short sleeve over the fiber. Properly sized capillary tubing is acceptable as are various fiber optic industry components. This sleeve increases the fiber's effective physical diameter to approximately coincide with the large-core distal tip. Since a precision alignment is not required, adequate tolerance is acceptable.

A second sleeve holds and aligns both fibers. The distal segment 2310 is fully encased in the sleeve while only a short section of the primary delivery fiber is bound. The two fibers are epoxied into the assembly.

As depicted by the dashed line, the distal end face 2320 can be cut at an angle so that a larger exit port is created for the escaping rays. This modification also minimizes refraction as the rays leave the fiber.

Application of a band pass filter coating to either the primary delivery fiber or the distal segment is effective in cleaning up laser light traveling to the distal end face. Fluorescence, silica Raman light, and other laser contamination which often accumulates as laser light transmits over optical fiber is rejected prior to final delivery. As an alternative to a coating, the band pass filter coating can be applied to a wafer which is inserted between the fiber segments.

The primary delivery fiber's small core and low numerical aperture creates several advantages. The low numerical aperture minimizes the accumulation and waveguiding of laser contamination during conduit of laser light to the distal end. Both factors minimize beam spread and spatial convolution as the beam traverses and expands in the final fiber segment.

FIG. 24 depicts an optical fiber 2405 positioned behind a short segment of large core gradient index fiber 2410. The primary fiber's delivery/receptivity pattern is directed and guided off axis by the gradient index segment 2410. As light propagates within the gradient index segment, light control is gently applied over a relatively long path length of manipulation. Although the index of refraction varies with axial symmetry, the variation steers the beam off-axis. As is evident in the diagram, only a sector of the gradient index segment interacts with relevant light rays. Thus, desirable characteristics are readily achieved by only utilizing the relevant portion of the gradient index fiber segment. By removing the non-relevant portion of the gradient index fiber segment, a small diameter specialized segment of gradient index fiber without axial symmetry is generated. FIG. 25 depicts a fabrication method by which the appropriate segment 2510 is removed from the larger gradient index cylinder 2410 by means such as core drilling the fiber segment or off-center cylindrically grinding. FIG. 26 depicts the resulting fiber segment 2510 adjoined to the primary optical fiber 2405. By this method, an optical fiber segment is created having a refractive index gradient that is not axially symmetric and producing off-axis delivery and acceptance characteristics. By utilizing low numerical aperture fiber as the primary fiber, the resulting zone of receptivity or delivery is tight relative to that resulting from higher numerical aperture fibers.

Those skilled in the art realize that various methods are readily employed to create the axially non-symmetrical gradient index fiber. These techniques incorporate methodologies utilized in the mass production df standard gradient index fibers and so called "grin lenses."

For example, a large-core, step index fiber may have a region on one of its sides with an artificially increased refractive index. Thus as light travels toward this region and interacts with it, the light is bent off axis in accordance with the laws of light refraction.

By utilizing materials whose refractive indices are a function of transmitted optical energy, the light's directional aspects may be steered. By introducing a controlling beam of optical energy into the material, its refractive index is intentionally manipulated. Thus, as the primary light interacts with the region whose refractive index is altered, primary light beam is steered. The controlling light should be injected so that it does not become entangled with the controlled light. For example, light introduced perpendicular to the fiber axis is not waveguided.

Additionally, the fiber may have refractive index gradients which are not only axially non-symmetrical but also include axially symmetric aspects. By supplementing the axially non-symmetrical gradient with an axially symmetric gradient aspect, the delivery and receptivity characteristics of the primary fiber are more tightly maintained as light is manipulated and directed off axis.

Gradient index optics are generally less environmentally stable than many other optical components. The index gradient may be permanently changed upon contact with various chemicals. Therefore, their usage must be analyzed for a specific application prior to deployment.

IMPROVED PROBE ASSEMBLY UTILIZING INTERNALLY REFLECTIVE SURFACES

FIGS. 27a–c illustrate an exemplary embodiment of a light-scattering probe 2700 utilizing the principles of light manipulation according to the present invention. A bundle of fibers is formed so that a center fiber 2710 is surrounded by a ring of fibers 2715. FIG. 27 depicts six surrounding fibers. However, in certain instances, seven ring fibers prove to be preferable. Similar configurations with various fiber quantities are preferable for specific usage goals. Depending on the application, the center fiber may be dedicated to light delivery and the surrounding fibers to light collection or vice-versa.

The bundle of fibers is bound together. To protect against cross talk, the center fiber's outer cylindrical surface near the distal end is coated with a metallic, light impenetrable film. Alternatively, a light-blocking additive such as carbon black is loaded in the bonding agent such as epoxy or inorganic cement which holds the fiber bundles together. The bundle may be formed as a free-standing assembly by epoxying the fibers together while the fibers are constrained by heat shrink tubing. Following epoxy cure, the heat shrink tubing is removed. This technique minimizes the diameter of the fiber bundle. If minimum size is not a primary constraint, the fibers should be collectively mounted in a tube or fiber optic connector. The internal dimension of this mounting hardware should closely match the outer diameter of the bundle.

To maximize light collection, the fibers are tightly bound together in order to minimize the space between delivery and receiving fibers. Step index, silica core, silica clad fibers with polyimide coatings are preferred. The polyimide coat should be removed near the distal tip of the fibers. This further minimizes fiber separation. The size of the fibers is dictated by the application requirements and overall system parameters. Fiber with a 400-micron core works well and is large enough to facilitate ease of fabrication. Depending on the application, small fibers are susceptible to detrimental sensitivity to dust, dirt, or other debris. Thin cladding walls are best, because they minimize fiber core separation. Nevertheless, cladding thickness must be sufficient so that the lightwave is fully contained. By heating and compressing the fiber bundle, the fibers can be fused together without the need of epoxy and further eliminating spacing between fibers.

Whether the fiber bundle is mounted in a connector assembly, needle tubing, or is free-standing, the bundle's distal end is shaped following its creation. As described earlier, various fiber shapes yield application-specific advantageous light delivery and acceptance patterns.

A pencil-point tip is readily created with standard fiber processing equipment adapted for the fabrication procedure. The fiber polishing equipment preferably is the variety with rotating abrasive disk platens. A holding mechanism, such as a collet, chuck, or similar device, supports and positions the fiber for polishing. The holding mechanism must maintain the fiber's primary axis at the desired angle of polish relative to the rotating disk. Whereas conventional, flat-faced fiber polishing is accomplished by positioning the fiber's central axis at a 90-degree angle relative to the surface plane of the rotating disk, the pencil-point tip bundle is formed by positioning the fiber at a lesser angle.

The holding mechanism preferably includes a provision to simultaneously rotate the fiber about its major axis and sweep it back and forth across the abrasive disk. It is important for the holding mechanism to possess sufficient precision so the axis of rotation is accurately maintained with respect to the fiber bundle's center longitudinal mechanical and optical axis.

To form the pencil-point tip on the bundle, the bundle is continuously rotated as it is swept back and forth across the polishing disk. Progressively a finer polishing medium is used to create a highly polished surface.

Forming the pencil-point tip with an included angle of approximately 40 degrees results in a probe with excellent performance for Raman spectroscopy, even in highly scattering and absorbing media. By decreasing this angle to 20 degrees, performance is reduced in demanding media but increased in intermediate conditions. At 10 degrees, performance is optimized for less demanding media.

In an exemplary embodiment, the end face is preferably coated with internally reflective metallic film following formation of the primary bundle shape. Various vapor deposition techniques are suitable.

Following formation of the probe tip, it is then flattened by grinding and polishing on the fiber polishing equipment. For the previously described point parameters, the tip should be flattened so that the flat region extends beyond the center fiber and into the ring fibers. The extent to which the ring fibers are flattened is dependent upon the numerical aperture of the fibers and application-specific parameters. If the flat section extends to include approximately 50 percent of the center cross section of the ring fiber, excellent performance is achieved for a point based on a 70-degree polish angle (40 degree included angle). This ensuing tip is well-suited for Raman analysis and performs very well even in dark, scattering media. As mentioned earlier, by reducing the included angle performance is readily tuned to various absorption and particulate scattering conditions.

FIG. 27a depicts a fiber bundle created in accordance with the previous techniques except that the application of internally reflected coatings is omitted.

FIGS. 27b and 27c depict the probe contained within a protective housing. FIG. 27b is a cross sectional view. FIG. 27c is an isometric view. FIG. 27b illustrates the presence of an internally reflective coating 2720. Prior to the formation of the flat surface 2725 on the bundle, the bundle is inserted and fixed into a hollow tube. As per application requirements, various mounting connectors are also adequate. FIG. 27b depicts a thin metal tubing 2730, which is often referred to in the industry as needle tubing. Initially, the tube should extend slightly past the tip of the bundle point so that the bundle is slightly recessed. The tube is next filled with epoxy or a similar material encapsulating the tip within the tube. Following this process, the assembly is flattened as previously described.

In many applications, protection against environmental abuse is desired. By applying a high-quality surface such as that achieved with 0.3-micron polishing film, environmental abuse due to chemical attack is minimized. Chemical attack in optical fibers is most severe at and may be initiated by surface imperfections. Nevertheless, in many cases, additional environmental isolation is required.

The application of the probe behind a window should be avoided due to the previously described negative aspects that windows impart. Environmental isolation is achieved by the application of various protective coatings. Examples of these coatings include diamond-like coatings or amorphous diamond coating, sapphire coatings, and various oxide coatings. The application of these coatings is facilitated by fusing the bundle into a solid mass as previously described. A thin, free-standing wafer can also be bonded to the end tip. Certain windows and coatings such as those in the diamond family exhibit strong Raman signatures. These signatures can be utilized to significant analytical advantage in certain application environments. As the source transmits through this medium, a Raman band is generated. When utilized in certain applications, such as those containing back-reflecting, Rayleigh characteristics, a portion of this Raman light returns from the primary measurand via the collection fiber(s). This signal can be utilized as a reference to establish both wavelength and intensity.

As previously stated, the dedication of light delivery and collection fibers is dependent upon application and system requirements. For Raman spectroscopy, the outer fibers are usually assigned to collection. Conversely, for applications such as diffuse reflectance measurement utilizing white illumination light, the ring fibers are usually best utilized for delivering source light.

In isolated media applications, the measurand may be susceptible to source energy. In these media, it may be advantageous to distribute the source energy among the outside ring fibers. In doing so, the surface area under illumination increases and, in turn, the power density to which the measurand is subjected decreases.

OPERATION OF AN EXEMPLARY PROBE ASSEMBLY

In addition to the earlier operational description of various components and optical surfaces, a general operational overview of an exemplary probe is insightful. Suppose the probe is configured for Raman spectroscopy with the center fiber utilized for laser delivery. This fiber delivers the laser light into the medium of interest. The medium Raman scatters the light thus producing Raman bands. Typical media of interest presents Rayleigh scattering, absorbing, and other characteristics that induce the often undesirable effects previously described in the Background section.

As depicted in FIG. 9, each ring fiber 2715 (FIG. 27) has two distinct zones of receptivity. The first zone 915 is controlled so as to intersect the illumination beam directly in front of the fiber end face. The internally reflective surfaces of the ring fibers direct these fibers to be receptive to Raman-scattered light very close to the probe tip. This first zone of receptivity extends between approximately 44 degrees and 32 degrees (where zero degrees is taken as coincidental with the fiber axis). Thus, the precious light is collected and the detrimental scattering and absorbing characteristics of the medium are circumvented. Tremendous performance increases are generated compared with those achieved utilizing alternative mechanisms. The second zone 910 of receptivity is responsive to light at a greater distance from the source fiber end face. With this configuration, the probe is responsive in highly diverse media.

The probe exhibits selective sensitivity to specific photonic mechanisms. The physics of this performance is based upon complex light-matter interactions as follows. The Rayleigh and Mie-scattered light is angularly biased and is frequently a multiple-event phenomenon. The multiple event aspects produce complex paths of light travel. Both the primary laser light and the silica Raman light emitted from the fiber are susceptible to Rayleigh scattering by the media. As such, their scatter is angularly biased. Fluorescence and Raman-scattered light are more directionally random or less angularly biased. Therefore, statistical bias exists between the directional aspects of scattered photons according to the scattering phenomena. Thus by angular manipulation of illumination and detection receptivity, the ratio of light collected from each photonic mechanism is advantageously set. Thus, a new, previously undescribed filtering mechanism is set forth for fiber optic measurement light-scattering phenomena.

The physics is believed to be somewhat akin to that of automobile headlights in certain driving conditions, such as fog, snow and rain. In a snow- or fog-ridden night, the driver sees better with headlights on "low beam" than on "high beam." The key difference between the low and high beam settings is the angle of illumination. Certainly, more light reaches the driver's retina driving on high beam, but it is the wrong light—virtually all scattered by the fog.

Because the angular orientation of scattered light is complex and dependent upon many factors, the probe is optimized by experimentation for specific application constraints. Empirical data indicates that orienting the collection zone approximately as specified above maximizes Raman probe performance in heavy particulate scattering media. In this configuration, the ratio of Rayleigh to Raman light produces maximum performance.

In a similar fashion, the probe achieves advantageous performance in analysis based on particulate scattering. It collects Rayleigh-scattered photons which have undergone a minimum number of scattering events. Thus, the acquired data is not convoluted by multiple scattering events.

PERFORMANCE OF AN EXEMPLARY PROBE ASSEMBLY

FIGS. 28, 29, and 30 depict performance levels achieved with a probe fabricated in accordance with the previous discussions. This probe was utilized in the configuration depicted in FIG. 27. Internally reflective coatings were not required as the test medium provided a sufficient refractive index differential to generate the required total internal reflection.

Results from the analysis of three probes follow. The first probe is a "Flat Faced/Parallel-Fiber" (FF/PF) Probe of the type described earlier. For the tests, it was deployed without a window in order to maximize its performance. The FF/PF Probe is heavily reported in literature and is particularly noted in medical literature. The second probe, denoted as the "Refractive End Face Probe", was manufactured in accordance with U.S. Pat. No. 5,402,508 to O'Rourke et al. under license from the patent owner. The Refractive End Face Probe's configuration was optimized by utilizing a flat-center source fiber surrounded by a ring of collection fibers angled at 20 degrees. The Refractive End Face Probe is positioned behind a 0.020-inch thick sapphire window, which is required for proper operation. In order to make even-playing field comparisons with the FF/PF Probe, only two of the Refractive End Face Probe's fibers were utilized. The third probe is Visionex's "Advanced Probe," which is fabricated in accordance with an exemplary embodiment of this present invention. As with the Refractive End Face Probe, only two of the Advanced Probe's fibers were utilized for the test.

For the test, all of the probe fibers were the same size and numerical aperture, and all equipment and test conditions were as close to identical as possible. For these tests, a broad-band, visible source was utilized with minimal ultraviolet energy. Performance from fluorescence and particulate scattering were the light-scattering mechanisms under investigation.

FIG. 28 is the spectra acquired by the three probes in a blood sample containing a fluorescent aspect. As would be expected, all three probes collected red light from the blood. In the red spectral region, the Refractive End Face Probe (line 2810) and the FF/PF Probe (line 2805) produce comparable results. The Refractive End Face Probe's performance is slightly superior. However, the Advanced Probe (line 2815) collects the red, elastic-scattered light much more efficiently. Nevertheless, the Advanced Probe was not optimized for this response. In a shorter wavelength region (slightly above 475 nm), further disparity is apparent. A fluorescent agent present in the blood sample generates a separate peak. The Advanced Probe picks up spectra from this agent whereas collection is not evident from the other probes.

FIG. 29 is an enlarged view of the relevant spectral region. The FF/PF Probe (line 2905) has no apparent detectable collection of light from the fluorescent agent. The Refractive End Face Probe (line 2910) produces a spectrum with a nebulous structure in the region; however, it is not clear what portion of this peak is a result of back reflection from the window and what is attributed to the trace agent. The Advanced Probe (line 2915), with its selective sensitivity to specific photonic mechanisms, efficiently gathers the required light and produces a clean spectrum. The ratios of elastic-scattered light to fluorescence light from the various probes clearly demonstrate this performance.

Perhaps more clearly, FIGS. 31 and 32 illustrate the selective sensitivity characteristics and the achievable results. FIG. 31 is a graph of the spectra collected in a red particulate scattering medium. FIG. 32 is a graph of the spectra collected in the same sample but with trace yellow-green fluorescent additive. Note the dramatic increase in ratio of collection of fluorescence light relative to inelastic light collection from the Advanced Probe.

FIG. 30 illustrates the results of probe tests conducted on an aqueous-based, red solution with minimum Rayleigh scattering characteristics. The test solution appears to be a clear, vivid red to the human eye. It is sufficiently red to quickly attenuate non-red light. The solution contains a violet fluorescence additive, which is not apparent to the human eye. In addition to the violet response, the additive also induces a yellow fluorescence response from the solution.

The FF/PF Probe (line 3005) generates the spectrum of lowest intensity and fails to detect both the yellow (500 nm–600 nm) and the violet (450 nm) fluorescent aspects. Whereas the blood inherently exhibits particulate-scattering characteristics, this test solution does not. In the blood, the illumination light returns to the collection fiber via multiple bounces and interactions with the medium during which the light becomes biased to the red. In the non-particulate-scattering test solution, minimum impurities are present to generate the pre-described effect. The FF/PF Probe's spectrum also exhibits a structure above 600 nm which results from reflections returning from the bottom of the sample beaker. (The solution is relatively transparent to these red and near infrared wavelengths.) The probe collects no appreciable violet or yellow light. As light from the source fiber excites the fluorescent agents, the fluorescent light is quickly absorbed by the red solution. And, the red solution quickly absorbed the fluorescent-inducing light. In fact, virtually all the excitation light is absorbed before it can reach a region to which the collection fiber is receptive. And, any photons which are generated in the region of receptivity are immediately reabsorbed before completing the return trip to the collection fiber.

The Refractive End Face Probe (line 3010) suffers essentially the same fate as the FF/PF Probe. Although the Refractive End Face Probe is able to generate a certain degree of light bending and light manipulation, it is insufficient to overcome the solution's attenuation. Additionally, the Refractive End Face Probe suffers another drawback. Reflection from the window is inadvertently captured by the collection fibers. The spectral structure captured by this probe is consistent with window reflection tests (not shown). Under careful scrutiny, feeble peak structure can be "imagined" in the appropriate spectral regions; although, they are certainly not definitive.

The Advanced Probe (line 3015) excited and captures violet and yellow light within the solution. Both peaks are captured clearly.

Under a battery of tests in various media, the Advanced Probe delivers similarly impressive results. Demanding conditions are present for a vast majority of applications where fiber optic instruments are considered beneficial and their usage is highly sought. These applications span from in vivo biomedical to environmental to industrial. Often, a species is believed to be a weak producer of the desired photonic effect when in fact the photonic mechanism is strong but the available instrumentation is insufficient to adequately acquire the generated light energy.

COMPLEX SURFACES

As previously indicated, additional light manipulation with advantageous results is attained by forming alternate surfaces into an internally reflective portion of the fiber's face. These surfaces are more complex than those described immediately above, yet they deliver superior performance for many applications.

By creating these surface contours in accordance with the previously described design techniques, light entering or exiting the ring fibers is further manipulated. The ray angles are directed as required for the specific application. Also, the flat portion of the fiber, through which light travels, is made smaller and still transmits all available light.

Whereas the kick-over zone is relatively thin in the pencil-point tip probe version, the zone can be readily expanded. FIGS. 7 and 10 illustrate representative performance improvements achieved by the application of more complex surfaces. However, these improvements complicate probe fabrication. The FIG. 7 embodiment is particularly useful in its ability to maximize response from a specific "focal point" region within the light delivery zone.

A fluorescence-spiked solution provides an excellent test bed for evaluating various probe shapes and architecture. The distal end of an assembly is immersed into the solution. Emitted light patterns are readily observed as the illumination pattern glows. Illumination and collection patterns and their overlap are also readily observed. To accomplish this, the test bath should contain a particulate scattering agent in addition to the fluorescence additive. Titanium dioxide is ideal. By injecting red laser light into the proximal end of the collection fiber, its receptivity is observed. The red light does not induce intense fluorescence but scatters visibly from the suspended particles. This general technique is useful as a design aid in configuring a fiber optic interface for specific applications.

Complex fiber contours may be generated in several manners. Computer controlled laser ablation is feasible but requires expensive equipment. The shapes are formed in a piece-wise linear fashion in accordance with the previously described techniques for creation of the preferred probe embodiment. The preferred method to create the complex shapes is through a polishing process similar to that described above. The machinery requires the additional capability of lifting and tilting, in unison, the probe during the grinding and polishing process.

ADDITIONAL ASPECTS OF THE PROBE ASSEMBLY: FILTERING MECHANISMS

As previously stated, source light, particularly narrow-band light, such as laser light, often becomes corrupt with extraneous signals as it travels within optical fibers. This effect is particularly troublesome for Raman spectroscopy. Thus, it is often advantageous to eliminate this light by applying a band pass filter in the vicinity of the probe, to the laser light conduit. Additionally, it is often advantageous to similarly apply a band stop filter to the signal collection fiber conduits.

Filtering may be accomplished in several manners. Interference filter coatings are applied directly to the fiber end face bundle. This technique requires difficult manufacturing procedures. It also suffers because the filters do not function well when light is incident at diverse angles; and, the probe's ring fibers are specifically designed for wide acceptance angles of light.

The center, laser fiber can be filtered by applying a filter coating to the bare fiber. The probe is then constructed with a lumen in its center. A cavity is created by constructing the probe with a capillary tube in place of the center fiber. After the probe is constructed in accordance with the aforementioned procedures, the center fiber is inserted into the lumen cavity and affixed into place.

Another useful and preferred technique is for each individual fiber to be separately filtered in a connector junction at an appropriate distance from the probe tip. Filter coating may be directly applied to the fibers or to filter wafers that are inserted between fiber end faces. This technique may cause the assembly to increase in size beyond acceptable limits if industry standard connectors are utilized. Thus, the preferred approach is to apply the filter coating directly to the short fiber segment end faces approximately one inch in length. The filtered end face is butted to the primary fiber length. This junction is made in a needle tubing with precision bore. Ideally, the tubing wall is 0.001–0.003" thick.

Another filtering technique is potentially useful. In this technique, unwanted wavelengths are angularly displaced. In doing so, light of undesirable wavelengths can be directed outside the fiber's internal reflection limits.

By surrounding the center fiber with seven smaller fibers instead of six of the same size, an advantageous geometry is created. The seven fibers are bundled separately into a tight geometric pack. The so-called packing factor can be further enhanced by heating the bundle until soft and squeezing it to remove all voids. FIG. 33 depicts a bundle, so created. Regardless, this configuration produces an advantageous packing factor and the bundle exhibits excellent circular geometry. It is possible to feed the bundle into a single, large-core fiber as depicted in FIG. 34. Various filtering mechanisms can be utilized in the junction between the bundle and large-core fiber. Using a large-core fiber that is slightly larger than the bundle overcomes the effect of divergence if the light spreads during transmission through the filtering mechanism. Although light density decreases as a result of the change from multiple fibers to a single fiber, total light energy is not significantly decreased. The effects of the slight decrease in intensity are system-dependent but are typically inconsequential.

The aforementioned configuration of connecting seven ring fibers to a single, large-core extension fiber offers other advantageous considerations. For example, the ring fibers are often utilized in the illumination capacity to deliver broad band light from a source lamp. In this instance, the source lamp's spot size is typically larger than the fibers. Therefore, no net light loss is realized as a result of the single-fiber-to-bundle junction (as long as the single fiber is larger than the bundle and the single fiber is smaller than the lamp's spot size). Additionally, any inconsistencies in the lamp's illumination pattern are mixed during transport to the junction so that illumination energy is equally distributed between each ring fiber.

As an alternative to the large-core fiber for transport, the entire bundle can be filtered. To accomplish this task, the individual fibers within the bundle are aligned with one another. The size of the fibers also influences the effectiveness of the technique. Larger fibers are obviously easier to align and typically exhibit less loss during filtering. An appropriate bundle alignment technique is described in U.S. Pat. No. 5,764,840, entitled "Optical Fiber with Enhanced Light Collection and Illumination and Having Highly Controlled Emission and Acceptance Patterns". Additional information is also described below.

The total length of the assembly is first established and a bundle of fibers is created whose continuous length is the desired length of the overall assembly. The bundle is tightly constrained and epoxied/bonded in the region in which the connection is to be formed. Tubing is a suitable component to achieve this goal. Heat shrink tubing is desired because of its ability to tightly constrain the fiber while allowing removal following epoxy cure and assembly. Rigid tubing such as metal, glass, or ceramic may also be used. Industry-standard connectors are also suitable. The fact that this type of tubing is permanent may be a benefit or hindrance depending on the desired characteristics of the assembly and overall space constraints. If the connection location is far removed from the end, cafe must be taken to prevent damage to the fibers while they are inserted into the tubing.

After the region is constrained and epoxied/bonded into a rigid section, a mechanical key or other identifying mark is placed along the section parallel to the axis of the fiber. The section is then cut perpendicular to the fiber axis. The cut is best achieved with a thin precision saw such as a fine-grain, diamond-impregnated wheel. After processing and polishing each side of the cut thereby forming the appropriate surfaces, the individual fibers are realigned by mating the two bundles together. This mating connection is accomplished by any of the methods typically utilized in the industry for mating single fibers. Rotational alignment is achieved by visually matching the previously described identifying marks or with mechanical keys.

This junction can be produced directly into the rigid section of the probe's distal tip. In doing so, care must be taken to isolate the delivery light from that received. Although a blocking mechanism can be introduced, it is best that the center fiber's junction be removed from the junction of the ring fibers. In accordance with the stated methodology, the junction for mating the ring fibers may feature a lumen in which the center fiber passes uninterrupted. The center fiber may be then broken for filtering, or have filter coating applied directly at its distal end face.

FIG. 35 depicts a probe assembly 3500, similar to that depicted in FIG. 27, that is adapted for filter application. The embodiment of FIG. 35 employs the lumen concept. It also utilizes the probe's outer metal tubing 3505 for a dual usage of bundle alignment and physical protection. The filters 3510 are applied directly to the short fiber segment end faces such that the filter is between fiber segments.

ADDITIONAL ASPECTS OF THE PROBE ASSEMBLY: INSTRUMENT INTERFACE

For the configuration in which the ring fibers are employed to collect light, the light from these fibers is transported to another instrument subsystem where the light is analyzed. Various instrumentation systems require specific fiber input configurations. Non-dispersive instruments typically accept the input in a circular geometry. Therefore, these instruments directly accept a fiber bundle or large-core fiber.

Another class of instruments is often referred to as dispersive. These instruments typically perform best when the input is arranged in a narrow rectangle. This configuration is often referred to as a slit; circular inputs are typically converted into this geometry by positioning the input directly in front of a physical slit.

For optimum performance, it is often advantageous to configure the fiber into a linear slit. This may be accomplished in several ways. For the bundle, the individual fibers are typically positioned into a linear array in a connector designed for this purpose. For the large-core fiber, the fiber is broken out into smaller fibers. In effect, the connection described above and represented in FIG. 34 is reversed. Since the desired slit width may be narrower than that presented by six fibers, a bundle with more numerous fibers can be utilized. As with the previous discussions, the bundle can be heated and compressed to minimize the non-active region of the bundle. Likewise, the linear array of fibers is readily compressed to further enhance performance. Fused bundles of fibers are often referred to as fused tapers and are often used for imaging applications. By creating a similar structure, an instrument adapter is formed to efficiently transfer the circular input into a linear, slit-style format.

As a variation on this theme, the large-core fiber, or a similarly constructed adapter is heated and compressed. In this compression, the total surface area should remain constant. To accomplish this goal, a die is fabricated from material that will withstand temperatures at which the fiber softens. The die should have an inner rectangular cavity of the desired dimensions. Typically it needs a thin rectangular cross section. It has a top and a bottom half which mate together. The die and fiber are heated in unison, and the die is compressed to closure. As it is compressed, the fiber takes on the shape of the desired rectangular cross section. Ideally, the transition from circular cross section to rectangular is accomplished gradually along the fiber's longitudinal axis.

ALTERNATIVE EMBODIMENTS FIBER GEOMETRY

Various geometrical configurations increase the ring fiber's size relative to the center fiber. For example, a five-fiber ring placed around a smaller center fiber provides potential results for increasing the extent of the intersection between the collection and reception zones and providing increased receptivity.

Two fibers in a side-by-side configuration with both end surfaces partially flat (providing entry/exit locations) for light reflecting from the internally reflective contour is another alternate configuration. It is well suited to instrumentation systems accepting only one source and one detector fiber. Of course, cost and simplicity advantages are also potentially realized. This set-up also delivers illumination light into the collection fiber's field of receptivity very close to the fiber end face. This fact is evident by noting that both source and detector fibers have components that are manipulated into intersection.

The center fiber is shaped into various contours such as a cone. In creating these contours, the center fiber protrudes farther in to the medium of interest. This protrusion positions the center fiber's end face into closer proximity to the ring fiber's zone of receptivity or illumination. Assuming the center fiber delivers energy, the closer proximity minimizes the distance through which the center fiber's light must travel in the medium until the light reaches an area of ring fiber receptivity. This technique is particularly effective in difficult to measure media; the refractive effects of the center fiber's contours are minimized for media with refractive indices close to that of the fiber. FIG. 36 is illustrative of the described effect of increased proximity for a multi-fiber probe. FIG. 37a illustrates the potential benefits for a probe with the collection fiber larger than the delivery fiber. Referring again to FIG. 37a, the sharp point also facilitates inserting the probe into materials such as biological tissue. In the FIG. 37a embodiment, the optical components are depicted encased in needle tubing. Furthermore, response is highly spatially specific within an investigative medium.

If the angular orientation of the delivery and collection fibers are aggressively shaped, the delivery light is forced to impinge on the collection fiber's end face. In doing so, indicator-type surface treatments can be applied to the fiber to produce desirous measurements. Similarly, surface treatments can be applied to the delivery fiber, with the collection fiber directed to view this region. If the coating scatters the delivery light appropriately, the scattered light is gathered by the collection fiber. This technique is particularly valuable for the branch of Raman spectroscopy often referred to as surface enhanced Raman spectroscopy. FIG. 37b provides an illustrative representation.

As stated, FIG. 37 depicts a single source fiber directing light in front of, and somewhat parallel to, a collection fiber's end face. In the figure, the collection fiber is shown to be larger than the delivery fiber. Depending on the medium and application, this may or may not provide enhanced performance. It is evident that the outer side portions of the collection fiber are somewhat removed from the source beam, which skims over the fiber's center. Therefore, it may be surmised that an oval fiber would be preferred. Slightly mashing the collection fiber results in an oval cross section, and the overlap between the delivery and receptivity zones increases. Similarly, an oblong, rectangular, or linear array of collection fibers can be utilized. This array provides additional useful light scattering information from the sample medium. By analyzing the light received from the individual fibers in relation to one another, valuable information can be obtained related to the medium's properties. FIGS. 38a–h are relevant, general illustrations.

SEPARATE ELEMENTS

In addition to utilizing the fiber's outer surfaces for internal reflection to achieve light manipulation, control is achieved with intimately attached elements. For example, an internally reflective fustrum of a cone may be attached to the end of the fiber bundle as in FIG. 39a. As previous discussed, the internal reflection is a result of total internal reflection or reflection from internally reflective coatings. The internally reflective end piece functions in accordance with the previous discussions. Preferably, the center of the end piece is drilled to facilitate insertion of the center fiber through the hole. This adaptation is important to prevent source energy from prematurely entering into the collection conduits. The end piece is fabricated from a materials in accordance with application requirements. By utilizing high-refractive index materials, total internal reflection can be realized for even liquids of relatively high refractive index. And if the high-refractive index material is a material such as sapphire, increased environmental isolation from chemicals and physical abuse is also realized.

FIG. 39b depicts another end piece embodiment. In this case the end piece sides are created with convex sides thereby generating effects previously discussed. In this embodiment, the contour is a frustum of a paraboloid of revolution with the geometric focus of the parabola positioned in front of the center fiber in the relative position of desired maximum response.

FIGS. 40a and 40b depict a probe in which the ring fibers are diametrically separated from the center fiber. The end piece, although in many ways similar to that shown in FIGS. 39a and 39b, exhibits an additional property. The end piece's side walls create internally reflective surfaces for internal reflection thereby generating a waveguiding effect. In this manner, light is not only angularly oriented but is also directed into spatial proximity with the center fiber.

RELATED EMBODIMENT ALSO UTILIZING INTERNALLY REFLECTIVE SURFACES

The previous embodiments utilized internally reflective surfaces in conjunction with an adjoining section formed to create an inlet/outlet for light. However, internally reflective surfaces are also utilized to advantage without forming a special inlet/outlet contour. FIG. 41 depicts a probe constructed in accordance with this principle. In this probe, the ring fiber's end faces are fully internally reflective. FIG. 42 provides an isometric perspective view of the fiber assembly of FIG. 41. The fiber's coatings are removed so that light readily passes through the side walls. Additionally, the center fiber is recessed into a clear capillary tubing. Thus, light passes uninterrupted between the area in front of the center fiber and the internally reflective surfaces of the ring fibers. The agent holding the assembly together, typically epoxy, is optically transparent, and its refractive index is carefully chosen in accordance with desirable operational effects. For this assembly, it is particularly important that the center fiber is metalized or similarly blocked from inadvertent cross talk with the ring fibers.

Among other things, this probe embodiment allows extremely minute samples to be analyzed by inserting the sample into the recessed cavity. For applications in which it is desired for the sample to inherently migrate into and out of the sample cavity, a portion of the raised side can be removed. By this action, fluid readily flows within the probe's sensing zone.

As with the previous probe embodiments, the internally reflective surfaces can be formed with complex contours so that additional light manipulation is realized. For example, a hyperbolic cross sectional shape is very efficient in light collection for energy emanating near its focus.

Creating a sharper bevel and subsequent longer taper on the ring fibers generates additional effects, as depicted in FIG. 43. A deeper sample cavity is produced.

Additionally, the fiber's zones of collection/receptivity is projected outside of the confines of the recess.

FIG. 44 depicts a similar configuration in which thick-wall capillary tubing is utilized so that the principal light transmission occurs through the capillary tubing's end face. Similarly, light can transmit through the center fiber's cladding or buffer if it is sufficiently thick, transparent, and constructed of a material with a suitable index of refraction.

FIG. 45 depicts a configuration in which the center fiber is formed to create an internally reflective surface. Assuming the center fiber is utilized for illumination, light interaction with this surface results in illumination exiting the fiber's flat section at diverse angles. The void created by tapering the center fiber is filled with clear material such as optically transparent epoxy. Detector light readily passes through this transparent material.

FIG. 46 depicts a configuration that is adapted for high sensitivity directly at the probe tip. This embodiment collects surface light without requiring passage of light through the medium under investigation. Thus, surface measurements are readily taken on various materials. The zones of illumination and receptivity are in coincidence as they intersect the probe's boundary and project outward.

Assume the center fiber is utilized for light delivery. The center fiber's light transmits through a section of transparent material such as clear epoxy, glass, sapphire, etc. Since many epoxies are prone to interfering, fluorescence, the material selection for the application parameter is important. The outer surface of this section is formed into a convex shape such that specular reflection from the outer optical surface is directed back into the center fiber. However, randomly scattered light, such as Raman, is collected by the outer ring fibers. This embodiment provides the added advantage of facilitating collection of a reference spectral signal from the clear encapsulant "window." If used to this end, the window material's natural signal can be augmented by the addition of a dopant that produces the desired response. Ideally, the reference spectral peak should be sufficiently removed from the analytical wavelength to minimize interference. But, it should be close enough to yield similar response to extraneous influences. Various other techniques can be employed to preclude the surface reflection from entering the collection fibers.

This control of a second-surface window, or transparent encapsulant, reflections is unique and novel. In general, suppose the radius of curvature of the "second" outer surface is such that the source fiber is positioned as the geometric center of curvature. In this configuration, second-surface reflections arising from light emitted by the source fiber are directed back into the fiber. In practice, significant deviation of the radius of curvature from the stated criterion is acceptable. This fact is based on directing the reflected light to areas such as source fiber cladding. This general tactic is designed to preclude reflection energy from entering the detector fiber. To be tactically effective, the reflected light can be directed to a location other than back into the source fiber. For example, it can merely be directed away from the collection fibers. However, directing the reflections back into the source fiber's core and cladding is preferable since it provides the ideal "light trap."

Superior performance is achieved in many media types by configuring a probe in a manner that provides illumination and reception zones which are coincident (overlapping) on the second (distal) surface of a transparent enclosure (window/encapsulant) which interfaces the media. As a crucial condition to achieve the superior performance, second-surface reflections (and first-surface) must be controlled so they do not inadvertently project into the collection fiber and undergo waveguiding. If they enter the collection fiber, they should be angularly oriented outside the limits for waveguiding.

FIG. 47 provides an illustrative representation accomplishing the stated goals. This embodiment is clearly distinct from that of FIG. 46, yet is operationally similar. The delivery fiber 4710 projects light through the outer convex optical element 4715 and onto its outer surface. Reflections from this surface are principally directed back into the fiber. The collection fiber 4720 has a manipulated field of view such that it is receptive to interactions at and beyond the optical element's outer surface.

Unlike the probes illustrated in FIGS. 41 and 43–45, the embodiment of FIG. 46 effectively captures signal from the point of first light contact with the sample, and beyond. It is not only effective for dark solids such as rubber, but also for fine crystalline powders. The probe is effective on crystalline powders, because the crystal's planar surfaces tend to orient themselves along the surface. Thus, specular reflection from the crystalline powder's surfaces is directed into the center fiber's core and back from where it originated. FIG. 48 provides a general understanding of how this crystalline powder phenomenon behaves.

FIG. 49 depicts two configurations in which a source fiber's illumination is directed over a single collection fiber. In one case the collection fiber's face is flat. In the other case, the collection fiber is angled to produce a closer proximity of the illumination beam to the collection fiber's face.

FIG. 50 depicts various cut-away and perspective views of an assembly which includes an optical end piece producing internal reflection. This end piece performs similarly to the end pieces previously described.

FIG. 51 depicts another variation in which source light is projected into a path oriented for direct for collection fiber receipt. In this configuration, various coatings, such as those used for surfaced enhanced Raman spectroscopy, are readily applied to the optical surfaces through which the light passes or appropriate materials are introduced into the gap between the fibers. Although depicted as bare fibers, each fiber can be encased or encapsulated in appropriate structures. For example, the structure may provide environmental isolation, additional light manipulation elements, or materials which provide enhanced photonic response to specific sensing conditions.

GRADIENT REFRACTIVE INDEX EMBODIMENT

FIGS. 52a and 52b depict a fiber optic probe utilizing gradient index optics to bend illumination from source fibers to coincide with the field of receptivity of collection fibers. In keeping with previously described principles, the center of the gradient index waveguide is drilled to allow for passage of the center fiber. If an alternate configuration is chosen in which the center fiber does not pass through a cavity in the gradient index segment, increased stray light is collected. Optical matching materials applied to the interface surfaces minimize this effect. Additionally, the distal end face of the gradient index segment should be formed into a shape such that outgoing surface reflections are directed for exclusion by the collection fibers.

In keeping with the principles previously developed in this document, individual gradient index segments can be dedicated to and applied on to individual fibers. And, as previously described, introducing a high-index region directly into the fiber core directs the region of receptivity or illumination as required for a specific application. The distal and faces of the adjoining fibers may be directly filtered.

REFRACTIVE END PIECES APPLIED TO THE PROBE TIP

FIGS. 53 and 54 depict the optical components of probes in which light is manipulated by refraction that occurs from light interaction with refractive elements. FIGS. 53a and 53b depict elements in which a hole is drilled and the center fiber is inserted.

FIG. 54 depicts a cross section of a probe with a center fiber surrounded by a ring of fibers. An element is fixed to the probe tip; in this case, it is a semi-sphere whose radius equals half the bundle diameter. In addition to refractive effects at the distal side of the element, this configuration yields another advantageous effect. With the source fiber positioned in the center, unwanted, internally reflected light from the radiused surface of the semi-sphere is directed back into the center fiber. Likewise, if an outer, ring fiber is utilized in a source capacity, internally reflected light from the outer surface of the element is directed away from the center fiber and towards the diametrical opposing fiber. In a similar sense, the zones of receptivity are also advantageously manipulated. For this probe to achieve refractive, beam-steering effects, the refractive index of the semi-sphere must be sufficiently differentiated from the application medium. Similarly, if the refractive indices are sufficiently removed from one another, total internal reflection occurs at the outer, side portions of the spherical element.

PROBES EMPLOYING LIGHT MANIPULATION BETWEEN ADJOINING FIBER SEGMENTS

FIGS. 55a–f depict various aspects of probes employing light-manipulating artifices between adjoining fiber segments. The depicted probes are configured with a ring of fibers surrounding a center fiber. The elements between the fiber segments modify the light entry/acceptance characteristics to create application-specific performance advantages.

An in-depth discussion of the operation and theory is presented within this document. Additional descriptions and specifications are presented in U.S. Pat. No. 5,764,840, entitled "Optical Fiber with Enhanced Light Collection and Illumination and Having Highly Controlled Emission and Acceptance Patterns". In light of this background, the operation and construction of these probes is clear.

By utilizing the principles and methodology presented, embodiments are readily optimized for specific applications and desirable effects.

FIG. 56 illustrates cross sectional and perspective views of a similar assembly which utilizes an end piece to create similar performance results.

Figure 57B:
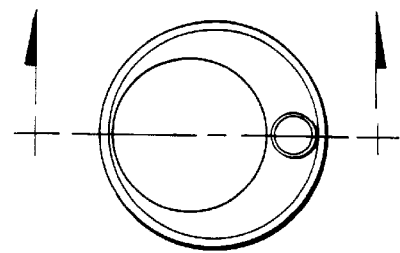
Figure 57C:
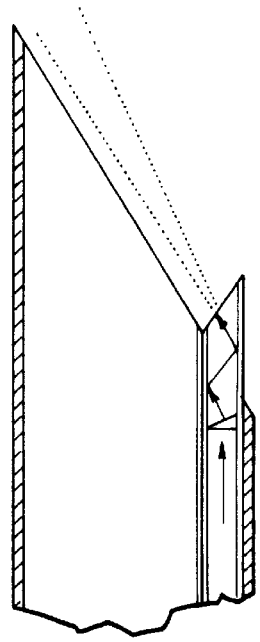
Figure 57D:
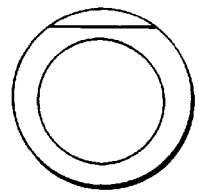
Figure 57E:
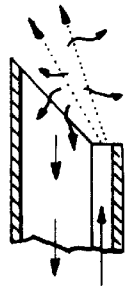
Figure 57F:
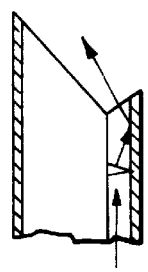

FIG. 57 depicts a probe configuration which is in keeping with principles developed within this document and utilizes the light-manipulation methodology developed within this section. This type of configuration is particularly effective for probe deployment in applications such as biological tissue and other complex matrices.

SEPARATE METHODOLOGY

FIG. 58 depicts a method of enhancing overlap between the source fiber's delivery beam and the collection fiber's zone of receptivity. In this depiction, a channel is formed into the collection fiber. The source fiber is bent and placed into the channel. Thus, the source fiber's energy is not only directed into a zone of receptivity, but also the fiber is almost fully encased by this zone. By utilizing small delivery fibers, light loss at the fiber bend is minimized. Variations on this theme include a hollow collection fiber with the source fiber formed into the center cavity. This configuration offers the disadvantage of manufacturing difficulty and susceptibility of damage to the fibers.

A SINGLE FIBER EMBODIMENT

FIG. 59 illustrates a single fiber adapted according to the presented methodology and achieving previously unattainable performance characteristics. In this embodiment, the fiber's illumination/collection characteristics are manipulated while maintaining symmetry about the fiber's longitudinal axis. A fiber with a numerical aperture of 0.22 is adapted to achieve an effective numerical aperture of 0.63.

Silica core/silica clad optical fiber typically has a numerical aperture (NA) of 0.22. This is a common fiber type employed in diverse applications and is the variety depicted in the illustration. NA=0.22 corresponds to illumination/receptivity field diverging in air with an included angle of 25 degrees. In a medium whose refractive index matches that of the fiber's silica core (approximately 1.46), the divergence angle is 17 degrees. Equivalently, the light is oriented within a range of +/−8.5 degrees from the fiber's longitudinal axis. And, this is the orientation of the light propagating within the fiber under fully filled conditions. The patterns and angles are depicted in the illustration.

FIG. 59 also illustrates the patterns created as a result of the adaptation. The resulting illumination/collection patterns corresponding to the new numerical aperture (NA=0.63) are also shown. The included angle is 78 degrees in air and 51 degrees in medium with refractive index matching that of the fiber core.

To achieve the desired result, a cone is shaped into the fiber tip. The included angle of the cone is 17 degrees. This angle purposely matches the propagation limits for light within the fiber. In this case, those limits are +/−8.5 degrees. By this geometry, light striking the sidewall of the cone is reflected to headings between 8.5 and 25.5 degrees and directed inward towards the fiber's center axis. The internally reflected light combined with the light that has not interacted with the cone sidewalls creates a diverse angular population of light rays spanning +/−25.5 degrees (51 total degrees).

The light enters/exits through the flat, planar portion of the fiber end face that is typically created by grinding and polishing the cone tip flat. In the illustration, the tip is flattened only to the extent that the rays reflected from the fiber sidewalls fully fill the inlet/outlet flat section. Simple ray tracing or algebraic equations are employed to fulfill this geometric condition. By tracing the rays contacting the cone section at the point of transition from cylinder to cone, the condition is easily met.

In simple procedural terms, the fiber is first drawn to scale. Next, the cone is drawn as specified. Three rays are drawn impacting the cone at the point of the fiber's transition from cylinder to cone. These three rays represent the fiber's normal angular limits for propagation and the average (+8.5, 0, and −8.5 degrees in the example). Next, the corresponding reflected rays are drawn. The cone is graphically flattened until the desired effect is achieved. In this case, the reflected rays fully fill the entrance/exit aperture.

Since actual performance deviates from the theory due to influences including the fiber's fill factor, experimental tests must be conducted to finalize the design specifications for a specific application.

If the fiber tip is created with a smaller inlet/outlet section (equivalently a longer cone section) the "sidewall" light strikes the opposing wall before exiting. In this manner, the illumination/collection pattern open wider. Similarly, if the flat section is larger, the percentage of illumination diverging at wide angles decreases.

As described in previous text, the angle of the conical portion of the fiber may be manipulated to create various effects. By increasing its included angle, a halo pattern is created by the "sidewall" light and two distinct illumination patterns are created. Similarly, by creating compound tapers (segmented cone angles) the NA can be further increased. And, this principle is taken another step by creating a complex contoured surface such as a paraboloid of revolution for the internal reflection.

The fiber tip is packaged and encapsulated in accordance with previously described methodology and/or application specific dictates. FIG. 60 provides a perspective view of a complete termination assembly.

In keeping with the multifiber probe embodiments, several adaptations are readily incorporated. The light-manipulating surfaces are readily formed into an element which adjoins a standard, flat-faced fiber. This adaptation offers fabrication advantages, in terms of facilitating mass quantity manufacturing of reproducible components.

The element is formed as a flat-ended cone (a frustum of a cone). This element is fixed to the end of a flat-faced fiber. By recessing the flat-faced fiber into a fiber optic connector, or similar tube, the element is readily attached and aligned.

Similarly, the special end face is formed into a short segment of fiber (typically a few millimeters). One end of the fiber segment is flat faced; the other end is shaped into the modified cone. This segment is adjoined to a standard, flat-faced fiber. The best method of attachment is to place the fiber into a needle, or capillary, tubing with the flat portion of the fiber's special end face parallel with the end of the needle tubing. If desired, the fiber can be inserted and fixed into the tubing while it is in the full cone condition. Then, the tubing and fiber are ground and polished to create the planar section. The flat end of the fiber must be free from contamination and recessed into the tubing so that an internal cavity is created. The male fiber is then inserted into the female end cap. It is attached with epoxy or similar bonding agent. With an optically clear bonding agent, migration of the agent between the fiber end faces does not result in an inefficient junction. In fact, the properly chosen agent minimizes transmission losses by acting as an optical "matching" material. Thermal melting adhesives are particularly useful if chosen to withstand the application's environment conditions. For this, fluoropolymers are well suited.

DELIVERING AND COLLECTING LIGHT ALONG A COMMON AXIS

The techniques described above may be used to construct a probe assembly suitable for delivering monochromatic light and collecting wavelength-shifted light along a common axis. A probe of this type is advantageous because it provides approximate concurrence between the optical axis of the delivery light pattern and the optical axis of the collection field-of-view. The probe minimizes the number and size of the elements (optical and mechanical) required for the assembly and eliminates the need for expanded beam optical elements in the primary light-delivery scheme. The probe also minimizes the extent of refractive index interfaces within the optical system, which can cause reflection within the assembly. Another advantage of the probe is that it can be used to deliver light to and collect light from an investigative medium without need of focusing elements and, when advantageous, can be directly inserted into the investigative medium. The need for these attributes is strong in applications such as biomedical, process control, down hole oil wells, composite curing, polymerization reactions, scientific research, and many similar applications. A device meeting the defined objectives is particularly needed to enable photonic applications in biomedical usages. This probe configuration offers the advantages of the prior art confocal devices without the inherent drawbacks.

FIG. 61 illustrates an exemplary probe 6100 for delivering and collecting light along a common axis. The wavelength intensities represented in the figure are merely illustrative of the general functionality; the actual intensities, relative to the laser (or other monochromatic source) wavelength are typically extremely weak.

In operation, highly monochromatic laser light is launched into the proximal end of the delivery fiber 6103. As the light 6101 is guided toward the apparatus tip, its wavelength purity degrades due to light-matter interactions with the fiber's materials which produce wavelength-shifted light 6102. This "silica-Raman" interference light is due to Raman scattering and fiber fluorescence; it is not specific to silica materials. The waveguiding nature of the fiber accumulates this extraneous light, which can interfere with material analysis techniques such as fiber-optic-based laser-Raman spectroscopy. Interfering light can also arise from other sources, such as laser instability (mode hopping) and ambient light sources entering the pathway. The laser light, centered at wavelength $\lambda_o$ and the wavelength-shifted interference light 6102 is transmitted to the delivery fiber filter 6105. The band-pass filter 6105 passes the laser light 6115 with only minimal transmission of the interference light 6116. The off-wavelength, interference light 6110 is reflected back off the filters 6105.

Instead of orienting the filters 6105, 6180 perpendicular to the fibers' 6103, 6108 axes, orienting the filter 6105,6180 at an angle offers advantages for certain applications. Referring to the delivery fiber filter 6105 for simplicity of explanation, it can be angularly oriented greater than the fiber's angular propagation limits (approximately 8.5° for silica core/silica clad fiber with 0.22 numerical aperture). As a result, the back reflected light cannot be back propagated towards the source. This is useful for several reasons. First, on very long fiber runs, a single, distal filter may not be sufficient. In this case, it can be advantageous to provide filters at interval distances along the fiber run so that a fiber segment within the run has filters on both the distal and proximal ends of the fiber segment. If the rejected interference light at the distal end of a fiber interval is allowed to back propagate within the fiber, then it will encounter another filter at the proximal end of the fiber interval and be reflected back again. Thus, the interference light can be trapped between filters. The filtering scheme loses its effectiveness as the trapped light passes through the filters; nonlinear effects also contribute to problems and corrupt the system performance. By angling the filters, the back reflected light is rejected outside of the fiber's angular propagation limitations. Second, back-reflected laser light, due to normal filter inefficiencies, increases the laser power intensity within the fiber. The additional laser intensity generates additional fiber interference without benefit of increased laser power delivered to the sample. Although this reflected laser is traveling away from the sample, it generates multidirectional interference light within the fiber core, which, in part, travels towards the sample. Therefore, the back reflected laser light should not be allowed to propagate. Third, lower-efficiency, less expensive filters, which inadvertently back reflect a larger percentage of desired light can be used. Fourth, back reflected light can interfere with the laser's stability if it is back propagated into the laser. However, for short fibers and stabilized, isolated lasers, this angled-filtering technique is typically not required, especially if high-efficiency filters are utilized.

As the light 6120 travels down the distal fiber segment 6162, a small, but increasing, amount of interference 6121 is present. The light 6120 is incident on the angled filter 6125. This filter is a notch (band stop) filter that reflects the laser light 6130 outward along with a small portion of unwanted interference light 6131.

The majority of the interference light that is incident on this filter 6125 passes through the filter 6125 along with a small portion of laser light 6135, 6136. This unwanted light 6135 must be eliminated from the signal path. Several methods are useful depending on the application environment. This light can be allowed to simply exit the assembly if the surrounding materials do not tend to re-introduce it into the return light path. The preferred method is to fill in the cavity surrounding the filter 6125 with optically transparent material, such as a silica plug or clear epoxy 6140. A light-absorbing section 6145 (for example, lamp-black-loaded epoxy) on the distal side of the transparent section 6140 traps and attenuates the unwanted light 6135. Preferably, the absorbing section 6145 has similar refractive index to that of the transparent section 6140 so that surface reflection is minimized. Other light-trapping configurations can be utilized. By shaping the final surface at an angle, or pointing it like a cone, interference from surface reflections is minimized and the assembly's insertion ability through biological materials is also improved.

The filter 6125 directs the pure laser light 6130 through the fiber sidewall and into the investigative medium. The laser interacts with the medium through elastic and inelastic processes 6150. Thus, light 6155, whose spectral composition 6156 includes the laser wavelength 6110 and shifted wavelengths radiates back through the fiber sidewall and is incident on the filter 6125. The filter 6125 reflects the unwanted light 6160 spectrally comprised 6161 of laser light and a small portion of the desired, wavelength-shifted light. The filter 6125 passes the desired light 6165 which is incident on reflective surface 6175 and is directed for propagation 6170 to the detector. The light 6170 is filtered again with a notch (band-stop) 6180 to eliminate residual, unwanted light 6163 at the laser wavelength 6110. The residual light may be due to such factors as cross talk 6190 and imperfect filtering. In keeping with the described reasoning, tilting the filter 6180 can improve performance. The residual laser light 6163,6164 is filtered out here to prevent it from generating interference light in the main run 6108 of the collection fiber and to minimize filtering requirements at the detector. Pure, wavelength-shifted 6172 light 6171 is guided to the detector over the main delivery fiber 6108.

For systems analyzing the investigative medium by Stokes-shift light processors, a low-pass filter can be utilized in place of the band-pass filter 6105 of the delivery fiber. Likewise, a high-pass filter can be used on the collection fiber in place of the notch filter 6180. And, a high-pass filter can be used as the tip filter 6125.

The filter fiber segments 6162,6173 are best attached to the main fiber segment 6103,6108 with a hollow sleeve (not depicted in drawing). For maximum performance, the sleeve must be sized for precise alignment. This may be achieved by lapping the undersized needle tubing to the precise bore. Or, the tubing can be fabricated by electroforming metal over a properly sized fiber then removing the fiber. A split sleeve, slightly undersized and spring tempered so that it firmly holds the fibers and achieves extreme alignment between fiber segments, is an alternative. The junction can be bound together with optically transparent epoxy which provides mechanical integrity and aids coupling efficiency. Care must be taken to ensure that the epoxy does not fluoresce. For certain wavelengths, the fluorescence is unavoidable. In this case, matching gel may be used to ensure the efficiency of the junction. In most instances, the index matching compound is not required.

The area of the assembly through which light is delivered to and collected from the investigative medium can have a reference material applied to it.

The cross talk 6190 can be minimized by metalizing the fiber's outer sidewalls in areas not requiring through-the-wall light transmission. Similarly, an opaque foil can be utilized to block cross talk.

A low numerical aperture fiber, such as single mode, can be utilized for the primary delivery fiber 6103 run so that the percentage of the generated silica-Raman/fiber fluorescence light which is accumulated and waveguided is minimized. This also allows for a sharper filter performance since it delivers light to the filter with reduced angular deviation.

The area of the assembly through which light enters and exits the investigative medium can be treated with an anti-reflective film, such as magnesium fluoride, so that reflection is minimized.

The collection fiber 6108,6173 can be larger than the delivery fiber 6103,6162 or comprised of a fused or unfused bundle of fibers so that collection efficiency is bolstered.

The main delivery fiber 6162 can have a smaller core than the delivery fiber tip segment 6162 such that mechanical alignment sensitivity is improved and the light transmits through the center of the filter 6105 so that filter performance is maximized. The main delivery fiber 6162 can also have lower numerical aperture so that filter performance is increased and less interference light is generated within and waveguided by the fiber 6162.

The reflective surface 6175 of the collection fiber 6173 may be internally reflective by a metallic coating or dielectric (stack) reflector or even be a filter itself.

The length of the distal fiber segments can be very short so that they do not provide significant waveguiding performance. In this manner, their interference contribution is minimized.

Fiber materials are preferably silica core/silica clad with a coat such as polyimide, which strips cladding modes.

As an alternative to directly applying the filters to the fiber end faces, they may be applied to a thin wafer which is placed up to the fibers' end faces or permanently attached.

The main delivery fiber 100 can be filtered with a Brag filter, which is preferably applied to a single mode fiber.

One or both of the filters 6105, 6180 on the delivery and collection fibers can be eliminated if reduced performance is acceptable.

Projection optics or light pipes can be utilized to project the investigative site further—for example, through a window.

The cylindrical surface through which light enters and exits the investigative medium can be reshaped to minimize distortion by flattening with heat softening, grinding flat, or building up the surface with optically transparent material.

The assembly can be utilized to monitor parameters within the human body.

One, or both of the end fiber segments 6162, 6173 can be formed of high purity sapphire or similar material such that hardening against physical and chemical hostilities is bolstered. They may also be hollow, waveguides such as tubes internally coated with reflective metallic coating.

The optics can be housed in various bodies to accommodate application parameters.

The assembly can be utilized for instrumentation analyzing inelastic light-matter interactions such as Raman and fluorescence.

FIG. 62 illustrates a fiber assembly 6200 in which light enters and leaves the assembly essentially parallel with the optical fibers' axes.

The depicted assembly operates similar to the assembly in FIG. 61 (as indicated by common element numbers) with several important differences. The source light 6220 in the delivery fiber tip segment 6211, which is incident on the distal filter 6225, functions differently. The distal filter 6225 is a band pass (or low pass for Stokes-shift analysis only). This filter 6225 allows the laser line light 6230 to pass through, unimpeded, into the investigative medium. The interference light 6235 is rejected by the filter 6225 and directed outward through the fiber sidewall. (By treating this area with absorbing material, the interference light can be trapped). The laser light 6230 that is transmitted through the filter 6225 passes through the transparent region 6240.

This region 6240 may be comprised of transparent conformal material such as epoxy, loaded with a reference standard, filled with investigative media, or plugged with a solid glass, sapphire, or similar piece. This area may even be joined with a short waveguided segment, although interference accumulates rapidly in even a short segment of optical fiber (more than a few inches).

Regardless of the material, if the outer surface of the region 6240 is properly shaped (beveled, coned, or similar), back reflected light from the outer surface will be less prone to inadvertent propagation to the detector. Regardless of the outer surface shape, the surface should be finely polished and is preferably treated with an antireflective coating. Ideally, the refractive index is matched to that of the investigative medium.

After passing through this region 6240, the laser light 6230 interacts with the investigative medium. Elastic and inelastic light 6255 returns from the investigative medium and is incident on the filter 6225. The majority of the elastic (no wavelength shift) light 6260 passes back through the filter 6225. The desired wavelenghth-shifted light is reflected by the filter 6225 and is reflected again by the internally reflective surface 6275 for propagation to the detector.

This configuration is well suited to operation in conjunction with projection optics which facilitate capturing information at a stand off or through a window. However, superior light-coupling performance is achieved by direct insertion of the device into or onto the investigative medium. Similarly, the delivery/collection field can be directed to the side with a mirror, prism, or similar optical component which may be directly attached to the distal end.

The assembly can be adapted for and the methodology is applicable to producing a similar image-acquiring device.

As with the side-viewing embodiment, this assembly can be produced with micro-scale optical elements attached to fiber end faces. A defining aspect is that the delivery and collection pathways are not significantly interrupted to allow for expanded beam optical elements.

The filters may be formed directly on the fiber end faces or first applied to a wafer intimately associated with the fiber. Direct application is preferred. For maximum performance, the filters should be high quality. However, depending on the application, lower performance filters are possible since one objective of this assembly is to minimize the need for elaborate filters. Nevertheless, better filters correlate to deployment of light-based characterization in previously unattainable applications. The highest performance filters are produced by processes which create high-density thin films. These processes include ion beam sputtering (single and dual beam), ion plating, magnetron sputtering and to a lesser degree ion-assisted deposition. Not only is high efficiency achieved, but also environmental stability is bolstered. Since filtering losses equate, in part, to increases in back reflected light, and the detriments of back reflected light have been explored, efficiency is an important factor.

By butting a capillary tube containing the investigative medium up to the optical inlet/outlet, signal strength can be enhanced. The capillary tube should have a lower refractive index than that of the liquid sample. (Or be internally reflective). Biological fluids such as blood plasma, urine, amniotic fluids, and cerebrospinal fluids are well suited to this method. Dupont's Teflon FEP fluoropolymer is a suitable material for some fluids due to its relatively low refractive index. Many of the common fluoropolymers have low refractive indices. However, the commonly known ones are higher than water and many aqueous solution. Water's refractive index is approximately 1.33. Hence, for aqueous solutions, a novel methodology is preferred. The capillary can be formed of Dupont's Teflon AF amorphous fluoropolymer. This material is also the preferred overcoat film or encapsulant to induce total internal reflection a the surface of the optical fiber contours which are described throughout this document.

This fluoropolymer may also be coated on the inside of a glass (silica) capillary tubing with internally diameter approximately equal to that of the delivery fiber end segment. The internally coated glass is preferred due to its advantages for reduced fluoropolymer cost and increased rigidity. This amorphous fluoropolymer is best applied to the capillary tubing in the solvent-dissolved state which is available from the manufacturer. The polymer-laden solvent can be swapped repeatedly through the capillary until a uniform film is built up. The film should be at least five microns thick for operation below 1000 nanometers and ten micron for near infrared usage (a thickness of approximately five percent of the tubing's internal diameter is best). The preferred method of polymer application is to add the mixture to the end of the capillary tubing while spinning the capillary lengthwise so that the mixture is forced down the capillary and a consistent coat is achieved. The solvent is driven off in accordance with the suppliers standard usage guidelines while directing air flow through the inside of the tubing. For volume manufacturing application and long capillary lengths, the polymer is applied as an internal film during the glass capillary manufacturing process. Added performance will be achieved with increased length of the capillary up to the distance through which light is attenuated. The maximum beneficial length is dependent upon the absorption of the investigative medium at the analytical wavelengths.

DELIVERING AND COLLECTING LIGHT THROUGH A COMMON APERTURE

The techniques described above may also be used to construct a probe assembly suitable for delivering monochromatic light and collecting wavelength-shifted light through a common aperture. The utility and adaptations for broadband usage applications, as opposed to monochromatic, are readily seen and are based on the teaching presented herein. A probe of this type is advantageous because it is capable of inducing and capturing light-matter response interactions at the surface interface (contact plane) between assembly and investigative medium. This is particularly useful in media that exhibit optical propagation difficulties, such as absorption. By varying parameters within the described configurations, the investigative depth beyond this contact interface is readily selected in accordance with application requirements.

This characteristic is in contrast to devices that are only responsive to light-matter interactions occurring at a depth within the investigative medium. As a result of this characteristic, the exemplary probes are capable of generating and capturing light-matter interactions in fully opaque materials. Similarly, information from thin layers and films can be acquired. For example, a film on, or layer of, any material (opaque or transparent) can be monitored with direct contact or minimal standoff. Furthermore, an indicator layer can be applied to the assembly surface through which light is transmitted to the subject and responses in this layer can be captured. As another special case, an imaging fiber optic probe assembly can acquire imaging information from a surface while in direct contact with the surface; this characteristic is particularly valuable for medical endoscopes.

This arrangement is also advantageous in the sense that specular reflections, which arise as delivered light passes the refractive index interface of the boundary between the fiber optic assembly and the investigative medium, are controlled to advantage. In applications in which specular reflection would interfere with the collection of desired light-matter response, its collection is minimized. Specular reflections are directed outside of the collection fiber's angular receptivity limits, waveguided for back propagation within the source fiber, and/or projected away from the collection fiber. As a special case, the micro-surfaces of crystal powders align themselves with the surface such that unwanted collection of specular light from these surfaces is minimized. In applications in which the specular interactions are of interest, the assembly's configuration is readily tuned to optimize specular collection and subsequent analysis.

In addition to the foregoing advantages, the number and size of the optical elements are minimized, and the optical elements within the delivery and collection paths are configured to minimize and control surface reflections from these elements. As a result, optical efficiency is maximized, and contamination of collection light with stray light interference from delivery light is minimized. Reliance on image trains of expanded beam optical elements is also eliminated.

As in the devices discussed above, by selecting the delivery and collection angles of light, the devices are readily configured to exhibit selective sensitivity to specific photonic mechanisms that are angularly biased. For example, the percentage of captured inelastic light-matter interactions, such as Raman and fluorescence scattering, can be increased relative to that from elastic processes such as Rayleigh and Mie-scattering and specular reflection.

FIG. 63 is a cross-sectional view of a probe in which a center fiber 6375 is surrounded by a ring of fibers 6380. The center fiber 6375 is utilized to deliver light and the ring fibers 6380 are utilized to collect light. This is the optimum configuration for laser-based analysis since the quantity of laser light injected into the delivery fiber 6375 at its proximal end (not shown) is not typically limited by fiber size. Other light sources, such as broadband lamps, are less effectively coupled into single fibers and are often better coupled into fiber bundles. Therefore, in many non-laser applications, the ring fibers 6380 are utilized to deliver light. This configuration offers the additional characteristic of angularly rich (diffuse) illumination of the investigative medium 6320.

In operation, light 6301 travels from the source down the optical fiber towards the distal end face of the center fiber 6375. In the illustration, the assembly is configured for laser-Raman spectroscopy. As such, the source light is highly monochromatic laser light. Through interactions with the fiber core 6310, the chromatic purity of the light 6301 is degraded. The band pass (or optionally high pass filter) 6355 rejects the unwanted, off-wavelength light so that highly monochromatic light 6301 is introduced to the measurand 6320. Specular reflections, arising as light rays 6301 cross the refractive index interface between the center fiber 6375 and the media 6320, are angularly oriented within the fiber's limits for angular acceptance. Likewise, in the depicted Raman configuration, Mie-scattering is predominantly directed backwards within the center fiber's waveguiding capabilities. Raman-scattering events are induced at the surface of the investigative medium 6320 and beyond (depending on the opacity of the medium). These events produce light rays that enter the center fiber 6375 end face, travel through center fiber core 6310, pass through 6340 center fiber cladding 6330 and travel into the collection fiber 6380 and intersect with internally reflective surface 6345 and are re-oriented for propagation within the collection fiber 6380 for transmission to the detection system. The collection fiber filter 6360 rejects the laser light via band stop (notch) or, alternatively, high pass.

The ring fibers 6380 are polished at an angle ø to create an internally reflective surface 6345. The ring fibers 6380 may be individually faceted such that the internally reflective surface 6345 is planar (flat) or preferably, and as illustrated, they are contoured so that they collectively form a frustum of a cone. The fibers are stripped of their protective coatings/buffers 6335 near the distal tip such that transmission of appropriately angled, desired light 6340 between the fibers 6375, 6380 is not encumbered. The bundle is held together by optically transparent bonding agent or are fused together. When bonding agent, such as epoxy, or inorganic cement (binder) is used, its refractive index should be close to that of the fiber cladding 6325, 6330. By approximately matching the refractive indices, the influence of refraction on desirable rays 6340 passing between delivery 6375 and collection 6380 fibers is minimized.

In some applications involving transparent liquids, the fiber bundle can be bound with only a thin heat shrink (preferably Teflon). The fluid medium can creep into the voids between the fibers and serves to transmit light rays 6340. Regardless, a certain degree of refractive index deviation is acceptable as the negative influences of the distortion is minimal. Although the refractive effects can be modeled and the configuration optimized to compensate, a trial-and-error approach is sufficient for a given set of materials (fibers and epoxy). The contour angle ø is readily changed until desired results are achieved. A visual method is valuable in optimizing the configuration. By sending light down the ring fibers 6380 towards the distal tip, it is bent at the internally reflective surface 6345 and redirected towards the center fiber 6375 end face. By placing the assembly into a bath, the emerging light can be viewed under magnification. For white light, the bath can be composed of water with a trace of fluorescence indicator. Alternatively, the batch can be composed of water with a small quantity of scattering agent, such as titanium dioxide. The water's low refractive index (approximately 1.33) yields total internal reflection at the internally reflective surface 6345, and thus, the need for coating 6365 is eliminated for visual testing. The light patterns are readily inspected by conducting these tests in a clear container with flat sides. A common aquarium is suitable; a cell culture flask (available from most laboratory supply houses) is ideal. This method is adequate as long as the angle ø is within the limits for total internal reflection given the other optical parameters.

Internal reflection at surface 6345 may be generated by several means. Total internal reflection will result if the medium contacting this surface 6345 has sufficiently low refractive index for the other relevant parameters (angle ø, refractive index of fiber core 6315, and angular propagation limits for waveguided light 6305). Typically, angle ø will be between 45° and 90°. In certain applications, such as monitoring of solid surfaces, the surface 6345 need only be exposed to air to create the conditions for total internal reflection. However, this open-air approach is less robust than is often required as the tip is mechanically delicate and losses can be created by contamination of the optical surface 6345. Still, the open-air approach is acceptable, and even preferred, when the device is utilized in pristine environments such as clean rooms—especially when precision-automated equipment is used to delicately position the device against the measurand.

Similarly, if the angle ø is high (typically 75°–85° for all silica fibers) then total internal reflection is induced in an aqueous medium when the surface 6345 is bare. If this approach is taken, the aqueous media should not contain absorbers, which can "frustrate" the internal reflection.

The surface 6345 can also be coated with a low-refractive index film 6370. Although magnesium fluoride can be applied through various thin film deposition techniques, it is difficult to provide a sufficiently thick coat to ensure the field of the collected light rays 6305 do not extend beyond the coat 6370 and become frustrated by adjoining materials. Several fluoropolymers are capable of forming this film. These include those known by the trade names FEP Teflon, PFA Teflon, TFE Teflon, Teflon AF and Tefzel—all manufactured by Dupont. Some of these polymers are available from other manufacturers under various trade names. Of these polymers, Teflon AF Amorphous Fluoropolymer is superior and FEP Teflon is next best. Teflon AF, sometimes referred to as amorphous Teflon, has the lowest refractive index, adheres well to the surface 6345, and is optically transparent for most wavelengths of interest. It has proved to provide excellent results on angles ø as small as 70°. Furthermore, it exhibits excellent properties for chemical inertness. The procedure for applying the Teflon AF follows.

Although the Teflon AF can be used as a melt extruded solid to encapsulate the assembly, applying the polymer in a dissolved solution is more economical and is better for short fabrication quantities. The assembly tip is dipped in a solution of Teflon AF (6% perfluorinated solvent (C5–18) 4,5-difluoro-2,2-bis(trifluoromethyl)-1,3-diolole (PDD), polymer with tetrafluoroethylene) designated by Dupont as Teflon AF 1600. Dupont's Teflon AF 2400 is also acceptable. Other percentage solutions are also acceptable. The assembly is allowed to air dry and then dipped again to build up a coat. The assembly is then allowed to air dry thoroughly (about 10 minutes). Next, the residual solvent is driven off by baking the assembly at approximately 112° C. for 5–10 minutes. The temperature is raised to 165° C. for five minutes. The temperature is raised to 265° to 270° C. for 15 minutes. At approximately 240°, the Teflon melts, uniformly coats, and adheres to the fiber surface 6345. The tip is inspected under magnification for anomalies; if present, the procedure is repeated until an acceptable coat is established.

Following the application of the polymer, the delivery fiber 6375 end face should be re-polished to remove the polymer from this surface. To increase the hardness of the assembly, prior to this step, the bundle may be inserted into a tube filled with epoxy so that the entire assembly is encapsulated. The end of the assembly is then polished to expose the bare fiber core 6310 of the center fiber 6375.

As another alternative, a thin, internally reflective film of metalization can also be utilized. It has the advantage over the Teflon AF coat in that it is not limited by the angle ø. And, all metallic reflectors are less efficient than total internal reflection. Therefore, the metals should be reserved for conditions (such as small angle ø) in which the Teflon AF approach will not produce adequate performance. For reflection in the near infrared, gold is an excellent reflector, and it also resists chemical attack. Since gold films do not adhere well to silica, a thin, essentially transparent layer of another metal must be applied as an undercoat. Chromium is suitable for this purpose it adheres to the silica, and the gold adheres to it. Although chromium has reduced reflectivity in the near infrared, this intermediate layer is very thin and does not significantly degrade reflection efficiency. For ultraviolet-visible light, aluminum works well. Silver is also suitable for visible and near infrared. However, neither silver nor aluminum exhibit good resistance to chemical attack and should be avoided in harsh environments. For harsh environments, rhodium or platinum is preferred in areas of the spectrum where their reflective properties are acceptable.

As yet another alternative, a dielectric mirror, created by the application of multiple thin film layers can also be utilized. By carefully designing the dielectric mirror, it can also pass selective, unwanted wavelengths of light (such as laser) so they are precluded from propagating within the collection fiber 6380.

If the distal segment of fiber is made of high index material, such as sapphire, the conditions for total internal reflection are more easily maintained. Therefore, this approach is an excellent alternative when the application requirements dictate the premium cost of the sapphire fiber.

Referring again to FIG. 63, when configured for laser-Raman spectroscopy, a filtering scheme can be utilized to enhance performance. As the delivery light 6301 travels towards the exit aperture, it is filtered by an interference filter 6355 such that only the laser light passes and the extraneous wavelengths are rejected. As depicted, the filter 6355 is applied to the distal fiber segment so that filtering is very close to the exit aperture. The filtered segment is joined with the main fiber segment in a small capillary (needle) tubing 6350. For medical applications, minimizing the diameter of the bundle is important, and the capillary 6350 can formed of very thin wall platinum-alloy. As a result of the alloy's strength, the wall thickness can be minimized while maintaining structural integrity. The precision of the internal diameter of this tubing 6350, compared to the fiber's outer diameter governs coupling efficiency and the effectiveness of the filter's blocking. A split sleeve may be utilized in place of the tubing 6350. The split sleeve's internal diameter should be slightly less than the outside diameter of the fiber. Since the sleeve can be expanded slightly, it accommodates the insertion of both fiber segments and maintains extremely accurate alignment. (During final assembly, the unit of filtered fiber segments is fixed into permanent position with epoxy or similar binding agent.)

For Stokes-shift Raman analysis, the delivery fiber should be filtered with a low pass or band pass filter. The filters should be of extremely high quality and should be sharp cut on/cut off. The purpose of the filter on the delivery fiber is to block light contaminated with interference, such as silica-Raman and fiber fluorescence. Thus, light delivered to the medium is clean in the wavelength regions of analytical interest. The collection fibers 6380 should also be filtered; although, this is often not a requirement. The purpose of the filters 6360 on the collection fiber is to block returning laser light and to permit Stokes-shift Raman light to pass. (Laser entry would generate silica-Raman interference on the return.) Therefore, these filters 6360 should be band stop (notch) or high pass and should likewise be of high quality. Index matching gel can be added to the mating surfaces so that coupling efficiency is maximized. By angling the mating surfaces of the adjoining fibers, another property is created. This technique prevents back propagation of reflected light within the fiber if the angle is properly chosen. The filter angle should be greater than the limits for light propagation within the fiber (8.5° for silica core/silica clad fiber with numerical aperture equal 0.22). This prevents light from bouncing back and forth in a fiber segment multiple times in a fashion similar to a resonant cavity.

As previously described, collection light 6340 enters and delivered light 6301 exits the assembly through the same aperture (the distal end face of the delivery fiber 6375) but at different angles. This property presents the opportunity to create advantage by applying a coating 6365 to the delivery fiber 6375 end face. By utilizing an anti-reflective coating (quarter-wave magnesium fluoride or similar) optical efficiency is enhanced and stray light performance is improved. By applying a coating which produces a known signal, a wavelength and relative intensity reference can be established for analytical comparison. For example, if the film has a Raman signature, the peaks of this film can be utilized by the system to verify proper operation, calibrate wavelength, and check relative intensity. Diamond coatings exhibit excellent Raman signatures. An indicator can also be applied which is responsive to specific measurand 6320 analytes. For example, fluorescent indicators which respond to specific biological chemicals can be attached to the end face. Various indicators and techniques for their attachment to matrices are available in the art. Similarly, films which undergo color change in response to specific physical and chemical conditions can be applied. In this instance, the film should have a scattering agent, such as titanium dioxide, to direct a portion of the light between the delivery and collection optical paths. Coatings which enhance a material's native response, such as those utilized for surface enhanced Raman spectroscopy can also be applied.

This approach of applying coatings (and even filters) to a fiber end face also lends itself to mass production. The preferred method is to apply the coating to the short fiber segment (approximately one-inch long). The end segment is then joined to the main fiber in a fashion similar to that described for the filter. However, another very valuable option is available when the junction does not contain filters or similar artifices. The segments can be fusion spliced together by any of the means commonly available. To improve stray light performance, all the optical end faces should be polished to a high finish (0.3 micron or better).

The illustrated configuration also lends itself to another referencing scheme. By injecting reference light into one of the ring fibers 6380 and choosing the appropriate angle ø, a portion of injected light can be captured by a collection fiber on the opposite side of the center fiber (following reflective bounce off of the center fiber 6375 end face). The internal reflection will only be significant when the end face of the center fiber 6375 is not in contact with the measurand 20 (prior to taking a measurement).

The application of the described device to a multitude of photonic applications should be obvious to those skilled in the art. Nevertheless, several specific application parameters are particularly noteworthy.

If the center fiber 6375 is chosen to be an imaging fiber or bundle, the assembly will capture spatial image data directly from a surface. Thus, a standoff between end face and imaged surface is not required for the introduction of light. This characteristic is particularly valuable in medical imaging of the human body.

Often, it is desirable to collect information from a layer slightly within a medium and minimize the influence of the initial boundary. For example, it may be desirable to investigate tissue layers below the skin's outer surface or under a finger nail. This capability can be enhanced by applying a matching gel or cream to the center fiber 6375 contact point. In biomedial spectroscopy, this method is valuable in numerous skin-to-window applications.

The ring fibers 6380 can be recessed below the assembly surface; angle ø need only be set appropriately. Similarly, these fibers may be moved outwardly and downward from the center fiber such that a separation is maintained between center fiber 6375 and ring fibers 6380.

The region adjoining the internally reflective surface 6345 can be encapsulated in a solid mass. The entire assembly can be potted into a rigid body.

By incorporating a lens assembly in front of the assembly tip, a projection system can be created to extend the measurement point to a short standoff location.

FIG. 64 illustrates an alternative, two-fiber embodiment. The delivery fiber 6475 has a curved internally reflective surface 6445. As a result, the delivered light is more angularly rich than would be the case if the surface were as described in FIG. 63. This assembly can be formed by the rotational polishing procedure described earlier. Note that the form of internally reflective surface 6445 is rotationally symmetric about the mechanical axis of collection fiber 6380. This is accomplished by forming the optical surfaces with dummy fibers positioned opposite the collection fiber (to maintain symmetry during fabrication). The surface form 6445 is readily designed utilizing ray tracing (manual or computer aided) to meet application dictates. The contour is then generated into the surface by controlling the tip interaction with the polishing platen. Either computer control or cam-based raising and tilting the assembly while it is rotating is acceptable. By forming the surface as a paraboloid of revolution with the geometric foci approximately at collection fiber 6480 end face, light delivery to this area is maximized. The illustration also depicts a flat area on the delivery fiber end face through which a portion of the delivered light 6401 passes uninterrupted. This feature enhances measurement in clear media since it extends the measurement range significantly beyond the distal end face. By this method, the light delivery pattern fully engulfs the collection field-of-view. The correlating advantage is produced when the delivery and collection roles of the fibers are reversed. This particular configuration is well suited to biomedical applications in which the fiber assembly is mounted in a needle or is used in a similarly small configuration.

As a derivative, the collection fiber 6480 can have a shaped end face, such as planar angled. This configuration is especially useful to prevent back propagation of outgoing light when the fiber 6480 is utilized in a light delivery capacity.

FIG. 65 illustrates an embodiment 6500 in which the assembly incorporates a quantity of fibers. Each of the collection fibers 6580 is responsive to light at specific angular orientations. The drawing depicts internally reflective surface 6545 profiled as a compound (two) angle. The number and angular orientation of linear segments is readily increased to any desired quantity to meet application requirements and is readily determined through ray tracing. Likewise, the contour may be smooth, such as a paraboloid. The drawing also accentuates the path of the surface reflection 6590 and the manner by which this reflection is contained by the center fiber 6575.

For best performance, the assembly end segment is fused together. The individual fibers can then be coupled to a large, single-core fiber. Preferably, this junction is accomplished by fusing the individual fibers together so that the junction has maximum efficiency (there are no gaps between fibers). And, the appropriate filters can be directly applied to this fused end face. At the spectrograph, for detectors in which a linear (slit) input is desirable, the large, single-core fiber can be readily broken out into the appropriate configuration. For this, a fused bundle of fibers is best. The bundle should be fused into a circle on one end and a rectangle on the other. The fiber can be loose in between the two ends or continuously fused. Care must be taken to maintain the same approximate surface area on each end so that the numerical aperture of the "fused, round-to-slit adapter" is not altered inadvertently. Or likewise, a desired magnification can be created.

As described earlier, the center fiber 6575 can be metalized on its outer surface so that cross talk between delivery and collection fibers is minimized. This metalization technique is very effective in fused bundles which are particularly prone to cross-talk. When an assembly is utilized for Raman spectroscopy, the cross-talk problem can be especially troublesome. The problem is troublesome, because the interaction of the laser light 6501 with the delivery fiber core 6510 produces unwanted fiber fluorescence and silica-Raman light. This light radiates in all directions and is prone to inadvertent collection and propagation by the collection fibers. The delivery fiber 6575 may be thought of as "glowing" with unwanted, potentially interfering light. Highly efficient collection mechanisms, as those described in this document, can inadvertently acquire this detrimental light. However, the metalization technique can be readily used to advantage.

Since the nature of the assemblies (fused and unfused) described in this document employ light transmission through fiber side walls to advantage, the metalization technique must be carefully applied. For best results, the center fiber 6575 is the only one metalized. The metalization 6596 should not extend fully to the distal end face; a section of the fiber end should be left uncoated. This bare segment facilitates the transmission 6540 of light rays between fibers only where this property is desired. The length to leave bare is obvious through simple ray tracing and is readily accomplished by masking during the metalization process. Alternatively, the metal is applied fully and then removed chemically in the desired area.

FIG. 66 illustrates an alternative embodiment 6600 in which refraction, created by contouring the outer fiber end faces 6635 into a refractive surface, is employed to manipulate the fiber's delivery/collection pattern 6660. The refractive effect as the light traverses 6640 the fiber sidewall is ignored for illustrative purposes. However, this additional effect increases the coincidence of the pattern 6660 with the center fiber 6675 end face.

FIG. 67 illustrates an alternative embodiment 6700 that is particularly useful for monitoring surfaces in open air. It offers the advantage of facilitating the direct application of filters 6760 on the ring fiber 6780 end face. Ring fiber 6780 end face can be shaped such that the collection of light emanating from the center fiber 6775 distal end face is enhanced. For example, by forming the ring fiber's end face into a cone the fiber 6780 better collects this light.

FIG. 68 illustrates an embodiment 6800 that utilizes a solid, internally reflective end piece 6850. This configuration offers several advantages, particularly for harsh environments. The end piece 6850 can be formed of sapphire, which has a high refractive index (1.77) and therefore is conducive to total internal reflection. The filters 6860 can be applied directly to this end piece. It can be manufactured in mass quantity through techniques common to the jewel bearing industry and its internally reflective surface 6855 can be shaped into complex contour. As an alternative to butting the main segment of the center fiber 6875 to a short segment of identical construction, the main segment can be adjoined to a short segment of sapphire rod. Filter 6855 can be applied directly to the sapphire rod. (The mechanical alignment component is not depicted in the illustration so that the function of optical elements can be best communicated.) By coating the rod with low-refractive-index polymer, preferably fluoropolymers such as Teflon FEP or Teflon AF, a short waveguide is formed. And unlike sapphire optical fibers, this segment does not need to be flexible. By encapsulating the entire tip in low-refractive-index fluoropolymer such that no voids exist between end piece 6850 and center fiber 6875 end segment, light rays 6801 transmit through the end piece sidewalls 6840 and are redirected for propagation. Other techniques include the addition of optical matching gel, clear epoxy, or other methods common to the optics industry. Since the wetted surfaces of the tip can be formed of sapphire and Teflon, this assembly is particularly well suited to harsh environment applications.

FIG. 69 illustrates an alternative embodiment 6900 that utilizes gradient index optics 6955 to steer the light 6901 so that it can pass 6940 through the center fiber 6975 side walls. As an enhancement for certain applications, the outer surface 6985 of the gradient index element 6955 can be coated with an opaque substance, such as metal, so that response to light emanating from locations other than the distal end face of the center fiber 6975 is minimized. Also, the distal surface of the gradient index element 6955 can be contoured to create an additional refractive or internally reflective effect.

FIG. 70 illustrates an embodiment 7000 in which the center fiber 7075 end face is shaped for light manipulation. In the illustration, the end face is formed into an internally reflective, frustum of a cone. As a result of this adaptation, the sensitivity to a small area at the distal tip of the center fiber 7075 is enhanced. This technique is particularly useful in instances in which a large-diameter fiber improves source-to-fiber light coupling. For example, when a lamp is utilized for source light as opposed to a laser.

FIBER OPTIC LIGHT MANIPULATION APPARATUS YIELDING SIDE VIEWING AND SIDE DELIVERY

The techniques described above may also be used to construct a probe assembly suitable for extracting information to the side. Such probes are particularly useful for biomedical applications in which light is utilized to characterize biological tissues and processes. Examples of the usage includes monitoring vessels and artery sidewalls, probing various body canals and channels, and insertion into small needles. Based on the intended use, the probe assembly needs to be configured to view various off-axis angles ranging from 90°-off-axis, to forward-looking-off-axis, to back-directed-off-axis. While the foregoing sections provide great detail to off-axis light delivery and collection field-of-view, this section teaches more detail in these regards. Specifically, the methodology through which the relevant variables are manipulated to optimality are described herein.

The optics described herein deliver light to and collect light from the side of a probe assembly. In this manner, information regarding the chemical and physical parameters of a material or process is acquired utilizing optical fibers. Internal reflection is utilized to steer the light to the desired location. The contour of the internally reflective surface is shaped to produce various results. These results include the position and size of the inspected region within the investigative medium. It also includes the angular orientation of the collection field-of-view optical axis relative to that of the light delivery pattern.

Separate fibers are utilized to deliver and collect light. The light may be monochromatic (like a laser) or broadband (white). The collected light may be shifted in wavelength relative to the delivered light or it may not.

As an alternative to internal reflection, gradient index optics are utilized for steering light.

FIG. 71 illustrates a probe 7100 that includes one delivery fiber 7175 to project a light delivery pattern 7101 into the investigative region. A second, collection fiber 7180 has a field-of-view 7102 that is likewise directed into the investigative region. The optical axis 7190 of the collection fiber 7180 intersects with the optical axis 7195 of the delivery fiber 7175 at a point 7185 to the side of the fiber pair.

In the illustration, to promote conceptual clarity, the diverging aspects of the light patterns 7101, 7102 are not represented. Where the drawing assumes parallel rays within the fiber cores 7110, 7115, the rays are actually randomized within angular limitations of the fibers' propagation capabilities (+/−8.5° for silica core/silica clad fiber with numerical aperture 0.22). This produces light patterns 7101, 7102 that are less sharply focused than those depicted. For the same reasons, the refractive influences of light crossing the fiber boundaries are not illustrated.

The internally reflective surface 7145 of the fibers are contoured into the form of a paraboloid of revolution 7175. The axis of revolution intersects with the geometric focus 7185 of the parabolic form. By choosing the appropriate parabolic form, the peak response region can be selected in an outward position—a desired distance from the fiber pair. Similarly, the region can be forward of the distal end such that the angle β between the optical axes 7190, 7195 and an axis parallel 7170 to the fibers and displaced through the intersection of these axes 7190, 7195 is greater than 90°. Similarly, the response region can be backward from the distal end such that the described angle β is less than 90°. In short, the probe is readily configured, by selecting the appropriate parabolic form, to generate peak response at various distances and angular dispositions relative to the probe distal end face.

Clearly, the apparatus can be configured such that the intersection point 7185 of the optical axes 7190, 7195 is a large distance from the distal end. However, at a larger distance, the region of maximum sensitivity may not surround this intersection; it will be closer to the apparatus tip. The larger the distance between intersection point 7185 and apparatus end, the greater the influence by medium transmission effects (such as absorption), multiple scattering events, and light divergence. These factors produce disproportionate response close to the end face for larger axes 7190, 7195 intersection 7185 distances d.

For configurations in which the angle between the optical axes 7190, 7195 and the fibers' 7175, 7180 longitudinal axis is approximately 90°, light will transmit between fibers' core 7110, 7115, fibers' cladding 7130, 7135, and the external medium with least interference from the refractive index differentials at the material boundaries. However, this configuration requires a large refractive index differential between fiber core 7110, 7115 and contacting material at the internally reflective shaped surface 7145. Therefore, this configuration favors metallic coating applied over the contoured surface 7145 to generate internal reflection. Nevertheless, total internal reflection is achievable with very low-refractive-index material, such as a gas, contacting internally reflective surface 7145 and/or high refractive index material, such as sapphire, used as fiber core material 7105, 7110.

Less aggressive light bending is required of the internally reflective shaped surface 7145 when the intersection of optical axes 7190, 7195 of delivery 7101 and collection 7102 patterns is more forward. In this case, the elsewhere-described fluoropolymer overcoat, generating total internal reflection, is the preferred method.

As light transitions the side boundaries of the fiber, the cylindrical contour distorts the light. The influence of this effect are lessened for liquid investigative media with refractive indices approximately matching that of the fiber materials. The cylindrical surface may also be re-contoured by such methods as filling-in with optically clear material such as epoxy (or full tip encapsulation with the described fluoropolymers). This material can also provide a measurement reference. A similar result can be created by polishing or heat softening and compression. The fibers may also be fused together.

The fibers' coating/buffer should be removed in the area through which light passes. This also enhances performance by promoting closeness of the fibers. The metalization techniques may be employed to minimize cross talk between delivery 7175 and collection 7180 fibers. The preferred method utilizes a thin foil fixed between the fibers during the fabrication process. The assembly also incorporates the ability to provide selective sensitivity to specific photonic mechanisms via angular bias of light-scattering processes.

As an adaptation, a portion of the end face can be polished flat (such as perpendicular with the fibers' longitudinal axis). By properly choosing the shape of the internally reflective contour 7145, the light patterns 7101, 7102 are directed forward and to the side through the flat section.

The internally reflective contour 7145 is not limited to the shape of a revolved parabola 7175. It may also be the form of a right triangle revolved about the axis, flat (each fiber faceted), elliptical, or any derived form, preferably revolved about an axis.

As a general rule, media is which light propagation in encumbered (such as absorbers) favor a configuration in which the optical axes 7190, 7195 of the delivery and collection patterns 7101, 7102 intersect close to the apparatus tip. This minimizes the distance within the medium through which light must propagate. This configuration can also be utilized to create an angular orientation between delivery and collection optical axes 7190, 7195 in which sensitivity to specific photonic mechanisms is enhanced.

As another important variation on the theme, the two fibers 7175, 7180 depicted in the illustration can both be utilized as light collectors. A smaller delivery fiber can be positioned directly adjacent to and between the two fibers (in the location designated 7160 in the illustration). By creating a similar, internally reflective contour on this fiber, the optical axis of its delivery pattern can be manipulated to intersect the other fibers' 7175, 7180 optical axes 7190, 7195 intersection 7170. The optical axis of the delivery fiber is not necessarily in the same plane defined by the collection fibers' optical axes 7190, 7195 (it can merely intersect this plane). Thus, light collection is maximized. By forming the delivery fiber end face into a planar surface, a filter coating can be applied to the surface.

FIG. 72 illustrates an embodiment 7200 that projects the collection pattern 7202 through the delivery fiber 7280. This configuration is readily adapted to meet various application requirements. For example, the collection pattern 7202 can be set so that the field-of-view encompasses the region of the source fiber 7280 through which the source light passes and emerges into the investigative medium. In other words, the light delivery and light collecting aperture can overlap on the assembly's outer surface. The individual shapes of the internally reflective contoured surfaces 7245 of the source fiber 7280 and the collection fiber 7275 are readily designed with ray tracing and/or geometric equations to generate this effect. Similar advantages to those offered by the previously described through-fiber-sidewall, straight-viewing assemblies, are available in this configuration. These advantages include the ability to conduct light-based characterizations in extremely opaque media. Configuration variations include fusing the fibers, utilizing multiple fibers, sizing either the source or delivery fiber(s) small in relation to one another, and forcing the delivery and collection optical axes essentially concurrent with one another.

FIG. 73 illustrates an embodiment that utilizes a large bundle (preferably fused) of collection fibers 7380 and a single delivery fiber 7375. The optical axes of the delivery pattern and the collection pattern are depicted as essentially concurrent.

By creating an angled, flat planar surface on the end face of the delivery fiber, a filter can be applied to this surface. If the filter is a notch (band stop) filter and the source light is highly monochromatic, the filter will reflect only the desired, monochromatic light into the investigative medium. The undesirable light (off-wavelength) will pass through the filter. Thus, by coating the filter with a transparent material, such as the previously described fluoropolymers, and over coating this with a stronger absorber (such as lamp black), then the undesirable light is trapped and excluded from corrupting the measurement.

Another important aspect of this, and similar configurations, is that each of the collection fibers 7380 are responsive to light traveling at various angular orientations and spatial originations. Thus, light in each collection fiber 7380 has undergone a form of spatial/angular filtering. And, by comparing the relative strengths of the light from each collection fiber 7380, additional information can be gleaned from the investigative medium.

FIG. 74 is an expanded view of the internally reflective shaped surface 7445 and light pattern 7450 (with the simplicity of parallel rays within the fiber) of a fiber assembly 7400. The fiber's internally reflective surface 7445 is contoured into a form defined by a right triangle's hypotenuse's path as the triangle is revolved around its upright leg with the upright leg positioned outside the fiber and the triangle's base perpendicular with the fiber's longitudinal axis. The internally reflective shaped surface is the surface region of a cone intersected by a vertical cylinder whose axis is parallel with that of the cone. In contrast to the parabolic profile detailed earlier, this profile is linear (not planar). In the cross sectional view, light is less focused than in the described non-linear profiles. Viewed from overhead, a strong focusing aspect is observed.

This surface lends itself well to manufacturing operations and is easily generated with high repeatability. Referring to FIG. 75, the set of delivery and collection fibers 7575, 7580 are bound together. The cross-talk-inhibiting mechanism is preferably integral at this stage. The fibers 7575, 7580 are fixed to the side of a mandrel 7585. The mandrel is ground and finely polished into a point by spinning the mandrel about its center axis while contacting a rotating abrasive disk with the mandrel oriented to the plane of the abrasive disk at the desired polish angle. As the fibers 7575, 7580 are polished, their centers sweep out a circular path 7590. From an overhead perspective, the lines defined by each fiber's center and the center of revolution 7510 are approximately the optical axes 7515, 7520 for each fiber. The optical axes 7515, 7520 intersect one another at the center of revolution. The fibers are removed from the mandrel 285 and moved to later stage fabrication processing.

The fabrication assembly may be fixtured as follows. A mold release agent is applied to the mandrel 7585. The mandrel 7585 is encircled with fibers 7575, 7580, which will make a quantity of assemblies. The fibers are held in place on the mandrel with a heat shrink (preferably TFE Teflon) so that the ends are exposed. Each fiber set (two or more fibers per set) 7575, 7580 is isolated from the adjacent fibers with a piece of thin TFE Teflon "plumbers" tape. Each fiber set will comprise a fiber optic apparatus. Metal shims, which prevent cross talk are placed between delivery and collection fibers. Optically transparent epoxy is applied to the fabrication assembly. The epoxy is allowed to harden. The assembly is polished, as described, to form the internally reflective shaped surface. The fabrication assembly is split apart so that each fiber set can be processed into a completed probe and housed accordingly.

A benefit of the described technique, for some applications, is the surface form which is generated by the epoxy's contact with the mandrel 7585. The epoxy fills in the cylindrical surfaces of the fibers. For large mandrel diameters, distortion associated with light entering/exiting the fiber through the fiber's cylindrical sidewalls is controlled.

Variations on this general theme are readily accomplished to generate various desirable results. For example, the mandrel 7585 can be made of wax and then melted away for each fabrication batch. By varying the angle of contact with the abrasive disk and concurrently raising and lowering the assembly (in staged steps, continuously under computer control, or mechanically with a cam assembly) complex internally reflective surface contours are readily created.

FIG. 76 illustrates another variation on this fabrication process, which produces devices with close-in focused optics. In this variation, a fiber bundle is polished without a mandrel. In the illustration, four fibers are bound together with heat shrink. A shim 7610 is used to segment the bundle into probes (in this case, two fiber pairs). After processing, the assembly is split apart. If both fibers 7675, 7680 in the pair are to be utilized as collection fibers, a side-delivery source fiber is readily fixed in the groove between the fibers.

FIG. 77 illustrates an alternative embodiment 7700 that utilizes gradient optics as an alternative to reflective optics. In this embodiment, a gradient optical element 7730 is attached to the delivery and collection fibers 7775, 7780. The element 7730 can be formed by core drilling a grin lens (the core is taken offset from the center axis of the lens). Alternatively, the grin lens is cylindrically ground (and polished) while spinning it about an axis of rotation offset from its normal optical axis. If a non-cylindrical form is desired, the element can be ground as desired utilizing a grin lens as stock. The refractive index gradient of the lens steers both the collection pattern 7702 and the delivery light pattern 7701 off axis. The element is held in place with a sleeve 7725 in conjunction with binding agent. The sleeve may encompass the entire assembly and, if metal, include a cutout for the passage of light 7701, 7702. The end surface 7740 of the element 7730 can be beveled, as shown, to facilitate insertion in biological tissues. Filters 7755, 7760 can be applied to the fibers' 7775, 7780 end faces which adjoin the element.

FIG. 78 illustrates an embodiment 7800 whose mechanical configuration is similar to that described in FIG. 77; however, the light is bent with internal reflection. The preferred method of fabrication includes metalization of fibers 7875, 7880 to inhibit cross talk. The fiber bundle can be fused together to minimize spacing when distal filtering 7855, 7860 is not required. The end piece 7670 is preferably fabricated from high refractive index material such as sapphire with the internally reflective surface 7845 coated with low index fluoropolymer to generate total internal reflection. The area of desired light exit/entrance can be coated with an anti-reflective film, such as magnesium fluoride. The end piece can be formed from a optical fiber whose diameter is the desired size. For highest efficiency, the internally reflective surface 7845 is shaped to facilitate overlap between collection 7802 and delivery 7801 light patterns within the investigative medium. For highly absorbing media, the contour shape 7845 is chosen, as previously described, into a form such as a parabola such that overlap is generated close to, or directly at, the medium/probe boundary. For clearer media, the contour shape 7845 is chosen to project the overlap deeper within the media. This end piece component is also useful for mounting on the end of a single fiber utilized for laser delivery in cutting and treating biological tissue.

Another adaptation is also useful. A clear (silica) capillary tubing is substituted for the sleeve. The tubing extends over the distal end, is sealed, and encloses a first-surface mirror. The mirror, oriented towards the fibers end faces, re-directs the light collection and delivery patterns to the side. The reflector is preferably aspheric concave (such as paraboloid) such that optical axes of delivery and collection light intersect. The reflector can be formed by shaping a fiber's end face. The fiber should have a outer diameter approximately equal to the inner diameter of the capillary tubing. The fiber end face is coated with a reflective film such as metal or dielectric mirror. Alternatively to making the mirror on the end of the fiber, the mirror may be ground and polished directly into a short metallic rod of the proper diameter.

IMPROVED FILTERING TECHNIQUES FOR OPTICAL FIBERS

Many of the phenomena associated with light propagation in optical fibers are dependent on travel distance in the fiber.

The accumulation of wavelength-shifted light with fiber length is an important example. Wavelength-shifted light is generated due to inelastic light-matter interactions between propagation light and fiber materials. These inelastic interactions include fluorescence and the Raman effect. Wavelength-shifted light arising from these interactions radiates in essentially all directions from an arbitrary region in the fiber core. Conceptually, it is useful to visualize an arbitrary region of the fiber glowing. The portion of radiated, inelastic light which is angularly oriented within the fiber's propagation limits is captured by the waveguiding properties of the fiber. The fiber is overfilled with this wavelength-shifted light. This captured light travels both forward and backward with respect to the primary, exciting light in the fiber. The radiated, inelastic light accumulates with fiber length such that it is more intense in longer fibers. This wavelength-shifted light manifests itself as interference in many fiber optic applications. Applications in which the signals of interest are weak—similar in strength to that of the interference—are particularly susceptible to detrimental influence. These applications include low-light spectroscopy such as Raman, some fluorescence analyses, and ilumines-cence.

Filtering techniques can be utilized to address this interference problem. Filtering capabilities are also important and needed for numerous fiber optic applications, such as wavelength division multiplexing in telecommunications. By directly applying a high-quality filter to a fiber end face, the need for expanded-beam filtering techniques can be eliminated.

Previously, thin-film filters have been applied to wafers which were placed between fiber end faces mated in standard fiber optic connectors. This technique suffers from multiple drawbacks. 1) The assembly/fabrication process is difficult and expensive at best. 2) It is not conducive to the fabrication of micro-sized assemblies, such as are needed for biomedical applications as well as many other usages. 3) Light diverges as it passes through the wafer's thickness; this leads to filtering and coupling inefficiencies. 4) The performance demands of low-light applications, such as Raman spectroscopy, necessitates high-performance filtering, which are not compatible with this design architecture.

Filter performance requirements for demanding applications, such as Raman spectroscopy include: a) high through put in transmission wavelength region; b) high-attenuation (dense) blocking in rejection wavelength regions; c) steep transition between wavelength regions of rejection and transmission; d) environmental stability; e) low ripple in passage regions, f) minimal sensitivity to temperature variation; g) no performance fluctuation with ambient humidity or chemicals; h) the ability to withstand high, and rapidly changing, temperatures present in sterilization processes and industrial processes; i) physical toughness; and j) tenacious adhesion between filter and substrate.

These desirable filter performance properties are achieved in thin-film filters having a large number of alternating high/low refractive indices, stacked layers deposited on a substrate. Between 20 and 150 layers are usually required depending on such factors as: 1) the performance required for the end use; 2) the refractive index differential between materials in adjacent filter layers; 3) the consistency and purity of the filter layer; and 4) the sophistication of the filter design process. And, the layers must be free from defects and voids such that the material characteristics of the layer approaches that of a bulk solid and the packing factor of the layer approaches 100%. Achieving high-density packing requires the molecules depositing onto the substrate to be highly energetic. During the layer deposition process, this energy prevents the forming layer from orienting itself into columnar or similar structures which are riddled with voids. While the depositing layers are predisposed to forming the imperfect structures, the high energy forces pack the molecules (or atoms) into any voids or pinholes which may exist. This high energy tends to impart residual mechanical stress to the substrate. These stresses cause curling and other problems in thin substrates. Thus, it is difficult to produce high-quality filters, with the described attributes and without expanded-beam optics, on thin wafers which would be suitable for insertion between fiber end faces.

U.S. Pat. No. 5,037,180 describes the application of a thin-film filter to a fiber mounted in an industry-standard ferrule; the ferrule-fiber unit is processed (polished and the filter applied) as a unit. Stone attributes deviations in filter performance to temperature differences between items in the filter chamber and to refractive index errors in the filter layer materials. The filter deposition processes described typically produce inefficient filters without the attributes described above. Stone describes two techniques which can be utilized to overcome the negative aspects of filter inefficiencies. The first technique is the usage of high refractive index material for the pertinent filter layers. By usage of silicone (refractive index approximately 3.2), filter performance is bolstered compared with such materials as titanium dioxide. Unfortunately, silicone does not transmit well in either the visible region or the near infrared region below 1.2 microns. Therefore, its usage is precluded for many important applications. Similarly, the choices of dielectric materials is also limited by toxicity issues, environmental stability, and other factors. The second described technique is to bevel the filter/fiber end face such that the filter's rejected light is reflected at an angle which cannot be propagated by the fiber. In this manner, the detrimental effects of filter inefficiencies are minimized for many applications.

It will be seen that the techniques described below provide an extremely attractive, novel means of filtering optical fibers. They are well suited to low-cost fabrication and are useful for instrumentation applications, such as Raman, fluorescence, and other spectroscopic analyses. They are also devised for wavelength division multiplexing, telecommunications, general fiber optic sensor usage, photonic computing, photonic amplifiers, pump blocking, fiber-integral active devices such as fiber-coupled (pigtailed) lasers and lasers utilizing the fiber as the lasing cavity.

In accordance with the present invention, a thin-film interference filter is applied to a fiber end face. The filter has a packing density of at least 95%, but preferably greater than 99%.

A fiber with an integral filter is utilized for analytical instrumentation/sensing applications generally and spectroscopy more specifically with significant benefit over the prior art for analysis involving low-light, inelastic light-matter processes, such as the Raman effect.

In an exemplary embodiment, a short fiber segment, preferably less than 24" but optimally 1.5" or less, has an integral filter applied to its end face. The segment can be joined to a longer fiber. With the filter on the distal end, the splice between the two fibers can be formed with a fusion process. With the filter on the proximal end (between the segments) the junction can be made with a sleeve. The sleeve is precision mated with the two fibers. The sleeve is best formed through nonconventional metalworking processes: electroforming or electrolysis plating over a precision mandrel. The mandrel can be a section of the optical fiber. The coupling can also be made with a split sleeve whose relaxed internal diameter is slightly less than the outside diameter of the fiber.

In one embodiment, short fibers are bound together in a bundle and filter coated as a group. Preferably, they are polyimide buffered fibers and are held in a PTFE fluoropolymer (common trade name Teflon), heat shrink tubing. The bundle, so constructed, may be large enough that it is simply held by the filter coating chamber's fixtures. Alternatively, it is held in a plate; the plate is preferably silica so that it can be used as a witness to control the coating process and also used after the batch process to grade the filters. The fibers can be held at an angle in the plate such that an angled fiber end face is flush with the planar surface of the plate; in this manner, an angled filter is applied to the fiber.

The filter can be applied at an angle of approximately 45° such that the reflected and transmitted light can be transmitted to locations in an optical assembly for subsequent processing. The filter can be oriented at an angle greater than the maximum angle of light propagation within the fiber so that reflected light from the filter cannot back propagate during low-light spectroscopy application, such as Raman.

Variability can be introduced into the thin-film application process so that filters of various wavelengths can be produced within a batch. The variability can be provided by masks, off centering, and raising and lowering the substrate. The slightly different filters can be graded and sorted.

Several short, filtered fiber segments can be aligned end-to-end with one another. One end of each fiber segment is angled and has a filter applied to its surface. The opposite, unfiltered ends of the fiber segments may be flat or formed with mating bevels. The filters are slightly offset in wavelength from one another. A clear, capillary tubing, preferably with one side polished flat, can be used to hold and align the segments. The assembly can used to tap off signals according to wavelength, or input wavelength-separated signals.

In one embodiment, a waveguided Raman cell is produced by introducing a fluid sample into a tube. Light is trapped and collected in the tube such that the signal is amplified. The tube's inner surface is preferably formed of the material known to the industry as amorphous Teflon.

THE FILTER APPLICATION PROCESS

As described above, the filter application processes that create filters with desirable performance attributes often produce residual stresses in the substrate. These residual stresses cause difficulties in applying the filter coatings to thin wafers of the types which, in the prior art, has been placed between adjoining fiber end faces in standard fiber optic mating connector junctions. However, by applying a filter coating directly to the fiber end face with a highly energetic filter process, previously unrealized filtering of optical fibers is achieved.

The preferred thin-film deposition processes imparts sufficient energy to the depositing molecules so that the forming structure is essentially fully packed (100% comprised of the desired molecules, essentially nonporous, and free of voids and pinholes). For best performance, the structure should approach or equal 100% (greater than 99%) packing density, but at least 95%. Due to this and other factors, adherence to the fiber substrate is tenacious. The effects of the residual mechanical stresses are negligible since the fiber is very strong in relation to its diameter. Several thin-film processes are particularly well suited to produce this high-density, hard-coated filter. These processes include magnetron sputtering, single- and dual-beam ion sputtering, ion plating, and ion-assisted deposition (typically slightly less performance and lower packing densities). Reactive and nonreactive versions of these processes are available. The reactive processes are typically faster in terms of the time required to produce a thin-film coating. These and similar processes contrast with conventional processes, such as evaporative films, which achieve packing densities of approximately 80%. Ion-assisted deposition produces films with densities typically in the 95% range and for this reason are less preferable. In short, a filter with high packing density—greater than 99%, preferably approaching or equaling 100%, but at least 95%—is applied directly to the fiber end face utilizing highly energetic, non-conventional thin-film deposition processes.

Variability can be introduced into the filter coating process so that fibers with filters of various wavelengths can be produced in a single batch. Several methods are useful in achieving the controlled variation. Selective fibers can be raised and lowered relative to the source which releases the film coating material. Selective fibers can be offset from the coating center. A mask can be applied to select fibers such that the amount of filter material deposited is varied according to position. These techniques are especially valuable in filtering optical fibers since a large quantity of fibers can be coated simultaneously—given the tooling methodologies described herein. Furthermore, fiber optic applications benefit from the availability of filtered fibers with slightly varied wavelengths. These applications include: 1) wavelength division multiplexing (input and output); 2) tapping off spectroscopic wavelengths for detection; and 3) matching filters to lasers with varying but closely grouped wavelengths.

TOOLING

In prior art methods of coating optical fibers, the fibers have been individually mounted in termination connectors. This and similar methods result in numerous problems. First, it does not make efficient utilization of the available coating surface area in the chamber. Relative to the size of the fiber end face surface area, a large space is required for the termination-connector assembly and also for assembly-disassembly working room. Coating chambers which produce the best coating control are small. Each batch run is expensive for a very high-quality filter. Thus, yield is a critical economic factor. Second, the materials in a finished fiber assembly include plastics and epoxy which can out-gas and cause problems with the coating process. Third, the material adjacent to the fiber end face is the termination ferrule. This material difference can lead to inconsistencies in the filter coating, particularly at the boundary region between the two materials. Fourth, the various materials in the chamber have different thermal conductivities. The bulk witness's (test plate's) heat transfer is vastly different than the fiber-termination assembly. Therefore, temperature consistency of the various materials is difficult to maintain. This is a problem since substrate temperature is an important coating variable. Fifth, the filter must be situated on the fiber end face. Here, it is susceptible to physical damage and environmental influence if left unprotected (depending on the coating type). There is no clear means to position the filter slightly behind the fiber end face. Sixth, the long fibers present space problems in the chamber. For these, and other reasons, an improved methodology for applying thin films, in general, and filters specifically, to optical fibers and similar cylindrical components is needed.

In contrast to the prior art, the methodology of the present invention produces high-quality, consistent filters with significantly reduced fabrication expense. The new methodology can be readily adapted in accordance with various needs. Nevertheless, the following description, referring to FIG. 79, is illustrative of the preferred techniques for a given application.

For Raman spectroscopy probes, step-index, silica core/silica clad/polyimide buffer fiber is the preferred fiber for these filtering operations. Gradient-index fibers and single-mode fibers are also compatible with the filtering processes and are preferable for some Raman probe applications. Low OH fiber is preferred unless the wavelengths of interest are outside its transmission capabilities. Fiber diameters of 300- and 400-micron core diameter are preferred for ease of workability (when compatible with application requirements). The fibers are scribed and parted into short segments 7901; one-inch lengths are ideal for ease of handling. The fiber segments are grouped into bundles 7902. For 400-micron fibers, 33 fibers per bundle 7902 are inserted in a PTFE (DuPont trade name Teflon) heat shrink tubing 7905 of size 14 gauge standard wall thickness. The tubing is approximately two inches long. The fibers are aligned in one end of the tubing. A heat gun is used to shrink at least the first one-half inch of the heat shrink/fiber bundle assembly 7912.

During the heat shrink process, the polyimide buffer on the fibers bonds slightly together so that the fibers are temporarily fused together inside the heat shrink tubing 7905. The bundle is ground and polished on the end 7906. Although not required, the polishing process can be aided by pumping, or pulsing, cleansing distilled water through the bundle during the grinding and polishing operation. This can be readily accomplished by coupling the tag end of the bundle's heat shrink tubing to the output tubing of a suitable pump. A pulsating pump is especially effective in maintaining cleanliness during the polishing procedure. The flow minimizes the extent to which debris is trapped in the cavities between the fibers. It also improves the fiber end face surface finish by removing ground particles from the polishing surface. The bundle is polished to a 0.3-micron finish.

After acceptable finish is achieved, the bundle is cleaned in a low-power, ultrasonic cleaner. No traces of debris should be visible under microscope inspection. The bundle is cleansed again with isopropyl alcohol and rinsed with acetone. The heat shrink tubing's loose end is shortened so that about ⅛ inch remains extended pass the fiber bundle.

Fused silica tooling plates 7910 are prepared to hold the fiber bundles. Square plates (1"×1"×¼") are suitable. The size and shapes of the plates are not critical—they are selected for compatibility with the coating chamber's tooling. The thickness of the plate is more important; the plate's stated ¼-inch thickness functions well with the given bundle size. The plates are drilled with four holes 7911 in a cross pattern. If desired, a large number of holes can be drilled to increase filter yield. The internal diameter of the hole 7911 is 0.145"–0.150" which is slightly smaller than the fiber bundle/heat shrink tubing 7912 outer diameter. The fiber bundle assemblies 7912 are inserted into the plate's holes 7911 with a light interference fit. Since there is a certain degree of variability in the outer diameter, the fiber bundle assemblies can be matched to various sized holes and/or trimmed on the outer surface for a good fit. After inserting the fiber bundle assemblies 7912 into the plates 7910, the entire assembly is cleaned and inspected again. First, it is cleaned with standard-grade acetone and finally with high-purity acetone. Ideally, suction is placed on the tubing back side so that any residual contamination is sucked away from the critical end faces. The assembly can be heated at 150°–175° F. for several hours to drive off any moisture from the fibers' polyimide buffer. The fiber bundle assemblies should be stored in a desiccated container until the thin-film coating is applied. These moisture reduction steps are not requirements but are recommended.

The orientation of the bundles 7912 in the plate tooling 7910 provides that two of the bundles will be aligned along the coating chamber's line of maximum consistency. And, the other bundles will be situated on each side of this axis. In this manner, the displaced bundles are slightly shifted in wavelength. The plates are positioned and held in the filter coating chamber's tooling for thin-film deposition according to the preferred processes described herein.

The fused silica tooling plate also provides a means to actively monitor the thin-film deposition process. And, since the material of the tooling plate is the same as that of the fiber, the thermal characteristics are similar. This factor minimizes the deviation between the thin film on the tooling plate and that on the fiber end face. The tooling plate is a witness and record for the filter coating batch. By scanning across the plate with a optical test jig, a contour representation of spatial filter deviation can be rapidly ascertained. In this manner, the optical characteristics of the filters on the fibers can be estimated without individual fiber testing. This proves especially valuable in filtering chambers/processes which exhibit regional variability. It is also useful in grading filters in runs in which variability has been deliberately introduced into the filtering process. The testing jig is composed of a fiber-coupled spectrometer with broad band light source. Collimating optics are attached to the source fiber. The collimated output is passed through the plate; the spectrometer's collection fiber is the receiver on the opposite side of the plate.

To separate the fiber bundle assemblies, the heat shrink tubing is first slit approximately ¹⁄₁₆" on unfiltered end so that a lengthwise halving is started. This is best done with a razor blade, being careful not to scratch the fibers. By simultaneously grabbing and pulling each side of this split with pliers or forceps, the split travels up the tubing and the bundle pops out unscathed and unscratched. It is akin to peeling a banana. The bundle can be readily separated into individual fibers by gently pulling with fingers.

Each fiber may be tested individually if high reliability is required for the final application. To minimize the complexity of this operation, the light can be coupled into the fiber from a diffuse source. Ideally, this source is a large planar surface. This type of source minimizes testing complexity as it minimizes positional sensitivity of the fiber relative to the source plane. For most wavelengths, a suitable source can be readily constructed by positioning a common, household flood light behind a frosted glass plate. For infrared filters, a heat lamp is preferred.

As a variation, the fused silica plate can be made thicker such that increased handling protection is provided to the fibers. Although the fused silica material characteristics provide the described advantages, other materials are acceptable. The alternate materials may be preferred for volume manufacturing operations in which the quantity warrants modeling and stabilizing all the variables associated with the thin-film process. Aluminum and PTFE plates have both been successfully employed in testing. The polymer manufactured by DuPont under the trade name Vespel reportedly has low out-gassing characteristics and is probably suitable or even preferred; however, its usage is cost prohibitive.

The described tooling configuration also supports the application of filters to angular fiber end faces. The fiber bundle, prepared in keeping with the described methodology, is ground and polished at the desired angle. The tooling plate is drilled at an angle relative to its planar surface. The bundle is inserted in the angled hole such that the end faces of the fiber in the bundle are co-planar with the surface of the tooling plate.

For high-yield filtering runs, an adaptation is well suited. In this adaptation, a larger quantity of fibers is bundled. The bundle can be formed and held in a variety of fixtures; however TFE fluoropolymer heat shrink tubing is preferred. This polymer has very low out-gassing characteristics, yet is gentle on the fibers. The outer diameter of the finished fiber bundle assembly is ½" to 1-½".

The bundles of fibers, packaged in heat shrink tubing, are readily produced. Fibers are first cut to a manageable length. This length may be anything from a few inches to many meters depending on the required volume. The desired number of fibers are collectively inserted into the heat shrink tubing. Individual fiber insertion should be avoided since it may result in the fibers scratching one another due to the sharp end faces. Following filling the tubing with fibers, the fiber bundle assembly is heated so that the tubing shrinks. During this operation, the fibers temporarily bind together (if the fibers are of the type coated with polyimide buffer). Next, the fiber bundle assembly is sliced into segments of the desired length. The best method is by using a fine-grit, sintered-diamond, high speed saw. Each fiber bundle assembly is ground and polished to a fine finish, preferably on both ends.

This large bundle is held in tooling within the filtering chamber. If both ends of the fiber bundle assembly are ground and polished prior to the thin-film filter deposition, then the filtered fibers can be graded or verified while the bundle is intact. For the grading, the described test jig's configuration is slightly altered. The finished filtered fiber bundle assembly is passed between the spectrometer's source and collection fibers. No collimated optics are required; the light is fiber-coupled directly into and out of the fibers in the fiber bundle assembly. The fiber bundle assembly is moved with an x-y positioner so that each fiber can be separately inspected. The spectrometer-coupled fibers should be similar, or smaller, in diameter than the bundle fibers so that individual fibers can be readily isolated for testing.

As another tooling option, a thin PTFE plate (approximately ⅛" thick) is drilled with holes slightly smaller than the fibers' outer diameter. The fibers, with at least one end face polished, are individually inserted through these holes so that an interference fit holds them in place. The plate is mounted over a small alurminum box so that the rear, unpolished, protruding ends are protected. The polished fiber end face is mounted such that its surface is flush with the plate's outer filter coating plane. If desired for extra protection, a thin aluminum plate with holes positionally matched to those of the PTFE plate can be fixed over top of the PTFE plate. The alurminum plate's holes are slightly larger than the fiber diameter. The fibers are firmly held by tight holes in the TFE plate and protrude upward through the larger holes in the aluminum plate so that the fiber end faces are flush with the outer surface of the aluminum plate.

The described tooling options also support thin-film coating of complex contoured fiber end faces. Referring to FIG. 80, an important subset of these end faces are fibers 8045 with cone-shaped end faces 8054. For this variation, the fibers are individually ground and polished to create the cone contour 8054. Following this operation, a bundle is formed with the fiber ends aligned with one another along a plane. The filter 8050 is applied over the cone surface 8054. This cone filter method is particularly effective in making filtered fibers 8045 that will not back propagate light reflected 8060, 8062 from the filter (both in the filter's pass and reject spectral regions). This filter configuration offers the advantage over a planar-angled filtered end face in that the fiber's optical axis remains essentially concurrent with the fiber's mechanical axis. In single-mode fibers, the core is typically about four microns. Thus, the change in height of the active core area, across the conical contour, in relation to the coating plane, is small. Hence, the influence on filter spectral characteristics due to the distance deviation between the cone shape substrate and the deposition source is manageable.

To control reflections, the angle β between the cone's base (perpendicular to the fiber's mechanical axis) and cone's outer surface (hypotenuse), is between 0° and 20°. To significantly reduce back-propagated reflection in multi-mode fibers, the angle should be greater than the fiber's angular limits for sustained propagation. By increasing the cone angle beyond this value, propagation is further reduced. The optimal angle depends on several factors including the population angles of propagation (the fiber may be over filled or under filled), propagation modes in the cladding, and the cladding's tendency to propagate back-reflected light. Experimentation based on usage parameters is the preferred method of optimization; nevertheless, 1-½ times the stated value is a good starting point for experimentation. Other factors influencing the design include the desired light pattern on the light-exit side of the filter and the spectral shift associated with angle of light incidence with respect to the filter surface. For single-mode fibers, 4° significantly reduces the back propagation of filter reflections. For 8°, the reduction is greater still.

This filtered, cone-shaped end face 8054 can be positioned against another fiber end face 8064 such that filtered light transmits between the fibers. By filling the void areas between the fiber end faces with index-matching gel or index-controlled material. such as epoxy 8052, the refractive influences of the shaped surface is controlled. In these manners, the back propagation of filter-reflected light is controlled, yet the refractive effects of the cone surface is overcome, or controlled. Similarly, the filtered cone can be encapsulated; the outer surface of the encapsulant is shaped into a flat, beveled, or other surface.

The filtered, cone-shaped end face 8054 controls back propagation of reflected light regardless of the direction of incident light. Back-reflected light 8060 due to light 8070 incident on the inner surface of the filtered cone is directed outside the fiber's angular propagation capabilities. Likewise, back-reflected light 8062 due to light 8072 incident on the outer surface of the filtered cone is directed outside the fiber's angular propagation capabilities.

FILTER DESIGN

The filter's physical implementation (number of film layers, film layer thickness, etc.) is readily generated with thin-film design optimization software. Dependence on the angle of incoming/outgoing light is a well-understood parameter. The primary variable in the design process is the wavelength blocking and transmission characteristics. The filter design process for fiber-optic-based laser-Raman spectroscopy warrants discussion.

For the laser-delivery fiber, the objective of the filter is to deliver light to the investigative medium with minimal extraneous, fiber-generated light in the wavelengths of analytical importance. Wavelength shifts from laser line is typically measured in wavenumbers (cm−1). The wave number shift of analytical importance is application dependent. The Stokes (red) shift is more often utilized due to its strength relative to the anti-Stokes (blue) shift. The fingerprint region (400 cm−1 to 1800 cm−1) is widely important; however, the region below 400 cm−1 is critical for certain applications. The required blocking is dependent on conditions of the investigative medium, the probe configuration, the relative strength of the desired signal (the strength of Raman-scattering of the analyte given its concentration) and the fiber materials of (construction and length. Generally speaking, the higher blocking in near the wavelength of interest, the better. The closer the blocking to the laser line, the better. The higher the transmission of the laser line, the better. For Stoke-shift analysis, a low-pass filter is acceptable. A band-pass filter facilitates Stokes and anti-Stokes analysis. The fiber-generated interference overfills the filter and therefore is incident on the filter at more diverse and less perpendicular angles than the primary laser light. Lower numerical aperture and single-mode fibers waveguide less interference and also deliver the laser light to the filter more perpendicular.

In keeping with these principles, the collecting fibers can be filtered with a notch filter so that the returning laser light is blocked. The higher the blocking, the better the performance. The incidence angle of the laser light returning into the notch filter from the investigative medium, due to elastic scattering processes, is typically less perpendicular than the incidence angle of the outgoing laser light on the band pass filter. This factor leads to incoming laser light passing through the filter if the filter is designed for angular incidences based on the fiber's normal angular propagation limits. However, this off-angle light mostly escapes through the fiber side walls before it can generate a significant level of fiber interference.

FIBER COUPLING

The following novel fiber optic coupling techniques can be used to join a filtered fiber segment to another fiber (or cylinder-shaped optical element) segment. However, these techniques are also applicable to general coupling of optical fibers. The basic problems of joining optical fibers with precision alignment, inexpensive components, and minimal size is addressed.

The fiber segments can be joined by a split sleeve with an internal diameter slightly smaller than the fibers' outer diameters. The fiber segments can be joined by a thin capillary tubing into which the fiber segment ends are inserted and butted against each other. The challenge associated with this approach is economically fabricating the tubing with sufficiently tight tolerance to provide precision fiber alignment. The challenge is increased by adding the additional constraint that the tubing wall thickness should be extremely thin and/or light weight. For numerous applications such as medical, military, and avionics instrumentation, these are critical parameters.

Non-traditional metal working processes can be employed to meet the described constraints. The coupler is produced by depositing metal on a precision mandrel. The mandrel is removed. If required, the coupler is chemically machined to modify dimensions.

A fiber can be utilized as the metal-deposition mandrel. The fiber is coated with silver or similar conductive material. This coating is applied with electrolysis coating.

For the silver application, the following procedure is suitable. Silvering chemicals are available from Lilly Industries, Woodbridge, Conn. Two solutions are required: MS-400 and MA-300. The MS-400 is, according to the manufacturer's literature, a solution of 26.6% silver diammine complex, 13% ammonium hydroxide, and 60.4% water. According to the manufacturer's literature, the MA-300 is a solution of 15% sodium hydroxide, 2%–10% ammonium hydroxide, 75% water, and a trade secret chemical. The MS-400 solution is diluted in a ratio of one part to 30 parts deionized water. The MA-300 solution is likewise diluted. The solutions are mixed together with the fiber in the bath. After the silver film has formed to a desired thickness, the fiber is removed from the bath and rinsed. Similar chemicals are available in the electrolysis plating industries from a number of suppliers. Numerous similar application methods can be utilized. The silver solution and the reducer are combined in a spray over the work piece.

Metal is deposited over the fiber's silver coat through electroplating (electrolysis). Nickel is the preferred deposition metal for this electroforming process. When the nickel reaches suitable thickness (approximately 0.001" wall thickness for the aforementioned 400-micron fibers), the piece is removed from the deposition process. The assembly is heated until the fiber buffer degrades, and the fiber can be removed. Alternatively, it can be removed by chemical attack. The sleeve is cleaned with acid which also removes the silver. By flowing acid through the sleeve after silver removal, its internal diameter dimensionally increases through a chemical machining process. The removal of the silver increases the internal diameter of the sleeve. This factor can be utilized to create sufficient gap to facilitate insertion of fibers into the sleeve during the fiber coupling procedure.

If desired, the sleeve can be produced entirely with an electrolysis plating procedure. If platinum-based metal or other high-strength metals are utilized, extremely thin sleeves can be fabricated. If using platinum then bare, un-buffered fibers can be employed as the mandrel. Since platinum withstands high temperatures, the fiber coated with platinum can be heated to sufficient temperature that the glass melts from the sleeve.

Using optical fiber as the electroforming mandrel offers the advantage of short-run fabrication. To reduce fiber expense, low-grade glass can be substituted in the fiber for high-purity materials. In volume production, a copper or brass wire can be utilized; however, specialized equipment must be set up to precisely control the diameter of the wire. Of course, electroplating can be accomplished directly on the conductive wire. And, the wire is readily eroded with chemicals to which nickel is essentially impervious.

To better facilitate fiber insertion, the ends of the sleeve may be flanged outward so that the ends taper to the correct diameter. This may be accomplished by electroforming over a mandrel having the desired shape. Alternately, a straight sleeve may be swaged outward at each end. Similarly, a sleeve can be chemically machined at each end or opened with electro discharge machining (EDM).

As a general rule, the longer the sleeve, the lower the precision of the fit which is required for low-loss coupling.

In a related procedure, ceramic materials are utilized to form the sleeve. The ceramics are packed around the optical fiber mandrel. After curing the ceramic material, the fiber is removed through heat and/or chemical attack.

When inserting the fiber segments into the coupling sleeve, optical matching gel or optically transparent epoxy/ cement can be used to increase coupling efficiency. For low-light spectroscopic applications, care and testing must be taken with these materials. Some materials fluoresce or have strong Raman signals which can interfere with the desired measurement.

As an alternative to simply bonding the fibers to the sleeve to form the coupling, the sleeve can be swaged around the fibers. This can be utilized in connection with or without the epoxy. With precision swaging, fiber alignment can be increased; thus, the coupling efficiency is bolstered.

As another method of joining the filtered fiber segment to another fiber, the segment can be joined with a fusion splice. This method typically subjects the joining surfaces to extreme temperatures. Therefore, fusion splicing methods can be effective when the filter is utilized on the distal end face of a fiber optic assembly.

For example, the short fiber segment is coated with a high-performance filter. The unfiltered end of the segment is joined to a longer fiber segment. The assembly is utilized for fiber optic sensing in medical applications and is disposed after each medical usage.

SPECIAL CASES

As stated, the described methods of coupling optical fibers are applicable to general optical fibers. Nevertheless, they are particularly useful in solving problems associated with filtering optical fibers. These filtering applications are neither limited to thin-film depositions on the optical fiber end face nor to filtered fibers in Raman spectroscopic applications.

A bundle of fused optical fibers can be directly coated with a filter. This is particularly valuable for imaging applications involving inelastic light processes, such as the Raman effect and fluorescence. The subject is illuminated via optical fiber or other source. The filter rejects the source light from collection by the bundle and passes light at the analytical wavelengths of interest.

A fraction of the filter layers can be applied to each of the mating fiber optic end faces within the coupler. The filtered segment of fiber may be filtered with a Bragg filter.

In contrast to traditional thin-film interference filters, which include alternating layers of high/low refractive index materials, rugate filters may be applied directly to the fiber. Since methods described herein produce a high filter yield per batch, they are particularly useful for rugate filters since the cost of a rugate filter batch run is very high. And, variability is readily introduced such that numerous, closely wavelength-spaced filters can be produced in a single filter run.

Although less preferred than applying the filter directly to the end face, the coupling methods support utilizing filtered wafers. A filter may be applied onto a thin wafer which is situated within the coupling, between the two end faces. The wafer may be attached to one of the fiber end faces prior to the assembly; or, it may be simply inserted as a separate unit.

The end segment of optical fiber can be formed of sapphire so that the assembly is hardened for harsh environments. The sapphire rod is coated with Amorphous Teflon (DuPont trade name Teflon AF) so that the amorphous Teflon creates a cladding for the sapphire. This novel method of fabricating sapphire fibers is particularly well suited to making short sapphire fiber segments. Not only is the fiber suited for extreme environments, but also it has a very high numerical aperture and transmission capabilities at longer wavelengths than silica fibers. And, by minimizing the length of the sapphire segment, the impact of sapphire's negative characteristics (birefringence, high Raman signature, expensive, poor flexibility, and others) is minimized. The negative impact of the fluoropolymer (differing thermal expansions, near infrared attenuation, and Raman signature) is likewise minimized. Amorphous Teflon is available in the refractive index formulations of 1.29 and 1.31. Sapphire has a refractive index of 1.77. This leads to a numerical aperture (calculated as the square root of the difference between the squares of the refractive indices of the core and cladding) greater than one for both formulations. For short lengths, the sapphire rod (unclad sapphire fiber) is dipped in a bath of solvent into which the polymer has been dissolved. Amorphous Teflon is available from the manufacturer in this form. Alternative to dipping, the rod is spun in a circle like the hands of a clock. It is spun at high revolution. The solvent/polymer mixture is applied to the end of the fiber which is at the center of revolution. The revolution forces the fluid down the fiber segment such that a uniform coat is applied. Regardless of the application method, the fiber is dried and the solvent is driven off in accordance with the manufacturer's general processing instructions. For volume applications, the molten polymer may be extruded over the sapphire fiber.

FIG. 81 illustrates a fiber device 8100 that separates signals according to wavelength and which can be readily fabricated utilizing filters fabricated in accordance with the current teaching. This device is equally useful for combining wavelength-separated signals into one fiber. Short, filtered fibers segments 8186 are stacked in a clear, glass capillary tube 8184. The fibers' end faces are angled—45° is preferred. One end face on each short fiber segment 8186 is filtered with a high-pass, low-pass or notch filter 8188. Each filter is separated slightly in wavelength according to the wavelength separation between signals. The wavelength separation can be generated by the methods of introducing variability to a filtering process which are taught herein. As illustrated the fibers are stacked end-to-end with one another such that the end face surfaces mate with one another. A fraction of the filter layers can be applied to each of the mating end face surfaces.

Alternatively to the mating end face having equal mating angles, one end of the fiber segment is angled and the other end does not mate (it may be flat or have a lesser angle). The gap between fiber segments is filled with transparent material such as optically transparent epoxy or index-matching gel.

For added performance, the filtered end face may be shaped (for example into an off-axis paraboloid) so that the reflected light 8192 is focused. The assembly is joined to a primary transmission optical fiber 8180. The fiber can be smaller in diameter than the short fiber segments 8186 and the annular spacing filled with a sleeve. This adaptation, not depicted in the illustration, facilitates better performance when the end faces are shaped for focusing. Light 8190 emitted from the primary optical fiber 8180 core 8192 is incident on the first filter 8188. This filter is a high-pass, low-pass, or band-stop which rejects the desired wavelength light 8192. This light is directed out through the capillary tubing 8184. The remaining light is transmitted through the filter and is incident on the next filter which similarly rejects the next desired wavelength and so on with the remaining filters. The side wall of the capillary tubing 84 can be polished flat or encapsulated in a clear material so that the refractive effects of light transmission through the capillary tubing's cylindrical side walls is minimized. Alternatively, the light can be coupled into a device, or assembly of optics which preferentially accepts light of the pattern shaped by cylindrical optics. The device can readily be constructed as either a combiner of wavelength-separated light or, as in the depicted configuration, as a separator of such light. This device is useful for sensing applications which require the comparison of wavelength-separated signals. It is also useful for wavelength division multiplexing and related data transmission applications.

FIGS. 82 and 83 depict probes whose optical fibers have mechanical and optical axes which intersect at a distance beyond the distal tip of the probe. FIG. 82 is a cross sectional view of a probe 8200 with a center fiber 8205 surrounded by a ring of fibers 8202, 8203. For laser spectroscopy, the center fiber 8205 is best utilized to deliver light since a laser's full energy output is readily coupled into the single fiber. For spectroscopy utilizing a less focused lamp, better overall performance is typically achieved by coupling the ring fibers 102, 103 to the source. Filters have been applied to the distal end faces of the fibers so that interference from fiber-generated light is minimized. For laser spectroscopy, the center fiber filter 8204 blocks interference in, at least, the spectral regions of analytical importance and passes the laser light. The ring fiber filters 8206, 8208 block laser light and pass light in the spectral regions of analytical importance.

FIG. 83 is a cross sectional view of a similar probe 8300 using two fibers 8320, 8322. This figure illustrates important advancements in the art as compared to that taught by McLachlan et al. in U.S. Pat. No. 4,573,761. First, the fibers 8320, 8322 are filtered on their distal end faces as described above. Second, the fiber's end faces have been flattened by removing a portion 8328, 8330 of the fibers 8320, 8322 so that the probe tip is finished in a planar surface. This advancement serves several important functions. In application media with refractive index lower than that of the fiber cores, a beneficial refractive effect is created on the delivery and collection optical axes of the fibers 8320, 8322. Whereas the optical axes 8332, 8334 would otherwise intersect some distance away from the probe, they are bent due to refraction to more converging positions 8336, 8338. Another benefit of this advancement is that the fibers are more robust and less likely to be damaged; thus, the need for a complex window assembly is reduced to only environments requiring additional protection. (As described earlier, fiber end pieces segments can be formed from sapphire fibers which are coupled to the primary fibers so that extreme robustness is achieved.) Another benefit of this advancement is that back reflection of source light which is incident of the fiber's distal end face surface cannot be back propagated. Still another benefit is the angled filtering, prevents back propagation of filter-reflected light.

In FIG. 83, the axis 8325 is perpendicular to the plane defined by the probe's end face. The fibers 8320, 8322 are angularly offset ø1,ø2 from the perpendicular axis 8325. The two angles ø1, ø2 do not necessarily need to be equal to one another. When the prove is utilized to either monitor a flat surface or project through a window, these angles can be manipulated so that specular reflections are precluded. Similarly, the angels ø1, ø2 may be equal, and the entire probe tilted with respect to the analytical surface/window such that the axis 8325 is not perpendicular to this surface.

Although not emphasized in the drawing, the filters can be removed from the end faces of probes configured similar to the illustrations of FIGS. 82 and 83. In keeping with the teaching described herein and in related patent applications, the filters can be moved inside a coupling, near the distal tip.

One class of probes utilizes an optical fiber with a flat end face (without intentionally induced refractive effects) surrounded by a ring of fibers which are essentially parallel to one another and to the center fiber. The end faces of the ring fibers are contoured such that the optical axes of all the fibers converge. A filter may be applied directly to the end face of the center fiber so that optical performance is enhanced.

Two or more fibers may be positioned as a group with filters directly applied to the fiber end faces. One or more of the fibers is utilized to deliver light and is filtered accordingly. One or more of the fibers is utilized to collect light and is filtered accordingly. When high performance is not required, either the delivery or the collection fiber filtering may be eliminated. The fiber bundle is positioned against an optical element which re-directs the optical axes of the delivery and collection fibers so that they overlap more than they would have had the element not been utilized. This element may be any element such as: 1) a gradient index component, 2) a lens, ball lens, a sphere, or other refractive component, 3) a concave mirror, 4) an internally reflective paraboloid, 5) a prism with contour on its internally reflective surface, 6) a diffractive optical element, 7) a waveguide, 8) a light pipe, 9) a partially or fully waveguiding hollow tube into which a sample is placed; the tube is preferably made of low refractive index material such as many fluoropolymers (such as the DuPont's Teflon family with Teflon AF the best); airy solids, so-called frozen smoke, can also be utilized to benefit, 10) a multi-pass cell such as a White cell or a Harriot cell, 11) a complex element which combines the refractive and reflective effects, 12) a holographic beam shaper, 13) an off-axis paraboloid, or 14) a non-imaging optical element. Similarly, the element may simply re-direct the optical axes of the fibers without substantially redirecting them into convergence. Examples of these elements include mirrors, prisms, and certain gradient index optical elements.

IMPROVED COLLECTION AND FILTERING OPTICS FOR CONFOCAL PROBES

For confocal probes, of the type described by Carrabba et al., U.S. Pat. No. 5,112,127, and Owen et al., U.S. Pat. No. 5,377,004, the image of a source fiber is projected onto or into an investigative medium. The light beam exiting this fiber is expanded and then re-focused into the medium. A collection fiber is similarly re-imaged along the same optical axis, so that its field-of-view is re-focused essentially to the same focal point as that of the source fiber. Although the devices in the prior art incorporate imaging-optics, they may utilize non-imaging optics; thus, the terms image, re-image, focus, project and concentrate are used loosely herein.

One shortcoming associated with the general configuration of these and similar devices is the inability to intensify the response arising from the focal point. Although larger fibers and bundles of fibers can be utilized as the collection fibers, this approach is not always effective. The lack of effectiveness is due to the manner in which the focal point of the larger fiber/fiber bundle is re-imaged around the focal point of the source beam. In short, most of the images miss one another at the critical focal plane. Nevertheless, the sensitivity increase which is achieved as a result of increasing the size of the fiber/fiber bundle is related, in part, to the medium's light transmission (characteristics (particulate scattering and other factors).

Increased performance can be achieved by shaping the end face of the (collection fiber/fiber bundle. Preferably, the center portion best remains flat so that the image of this region is projected to concurrent focus with the source beam focus. The surrounding areas of the collection fiber/fiber bundle is best adapted for light manipulation. This manipulation may be produced by either refraction or internal reflection. Internal reflection is readily accomplished with the teaching described herein. Refraction is readily produced by shaping the end faces of the fibers to create refractive surfaces. Based on the specific optical configuration of the probe, the medium (characteristics, and application parameters, the desired effect can be optimized with ray tracing and/or optical design software. For a fiber bundle, consisting of a ring of fibers surrounding a single central fiber, the ring fibers can be beveled at a refractive angle. The refractive angle is typically between 5° and 30° (measured between the base of the bevel angle or cone and the hypotenuse). Likewise, a large single fiber can be formed into a refractive frustum of a cone. Internal reflection can be utilized by applying a frustum of a cone to a large single fiber (the side walls are internally reflective). The flat region of the frustum should be approximately the same diameter as used for the non-enhanced probe. Similarly, the bundle approach can be utilized by forcing the ring fiber to look through the center fiber's sidewall and on through the center fiber's end face.

The choice of methods which are employed are related to the focusing abilities of the probe to which the enhancement is applied. For example, if the enhanced area of the fiber/fiber bundle is too aggressively redirected, its field-of-view can miss the focusing optics, and simply look at the optical housing—this is ineffective.

Another method which is valuable is to utilize a collection bundle in which the fibers are positioned so that their optical and mechanical axes are not co-linear but are converging. This may be accomplished with two or more fibers. In the preferred approach, a central fiber is surrounded by a ring of one, two, or more fibers. The ring fibers are tilted slightly inward so that their (its) mechanical/optical axes converge and intersect with the axis of the center fiber.

IMPROVED FILTERING

Fibers, filtered in accordance with the teaching described herein offer significant performance, miniaturization, cost, and robustness improvement for confocal probes. They can be utilized to filter the delivery fiber and/or the collection fiber. They can also be utilized for the bidirectional, angled filter which combines the optical axes of collection and delivery.

AMPLIFIED RESPONSE

The earlier section regarding delivering and collecting light along a common axis describes a method for fabricating a waveguided cell that substantially increases analytical sensitivity to light-matter interactions. This cell is particularly well suited to fiber optic interfaces which are filtered in accordance with the current teaching. However, its utility is certainly not limited to these interfaces.

FIG. 84 depicts a waveguided cell 8400 configured for transmission (absorption) analysis of a fluid. Preferably, the cell is formed such that the internal surface of the tube 8464 is made of the material which is sold by DuPont under the trade name Teflon AF, or more commonly known as amorphous Teflon. For fluids with sufficiently high refractive index, other materials are acceptable; these include the fluoropolymer sold by DuPont under the trade names Teflon FEP, Teflon PFA, and less preferably Teflon TFE and Tefzel. At one end of the tube 8464 is a source fiber 8450. At the other end of the tube 8464 is a collection fiber 8452. An inlet port 8458, at one end of the tube, delivers fluid 8454 into the tube 8464. Fluid 8456 exits the tube 8464 through an exit port 8460, at the other end of the tube 8464. As light 8462 is waveguided down the tube 8464, it interacts with the fluid in the tube. By spectrally comparing the light received to the light delivered, the transmission characteristics of the fluid are readily ascertained. One method of making this comparison is to fill the cell with a reference material before or after taking the primary measurement. Another method is to divert a fraction of the source light to a detector.

The cell can also be used for analysis based on the Raman effect and other weak inelastic responses. By delivering laser light through the source fiber 8450, inelastic light-matter interactions (such as Raman scattering) are waveguided along with the primary laser light. By applying a filter, in keeping with the teaching described herein, to the end face of the source fiber 8450, purity of laser light is enhanced. Furthermore, inelastic light radiating from the sample, captured by the waveguiding capabilities of the tube 8464, and back propagating towards the source fiber 8450 is reflected by the filter, towards the collection fiber 8452. By applying a filter in keeping with the teaching described herein, to the end face of the collection fiber 8452, the laser light is reflected back and the inelastic light is allowed to pass into the collection fiber 8452 for propagation to the detector.

By choosing the collection fiber's filter's spectral characteristics are chosen so that a small fraction of the inelastic light is transmitted and the remainder is back reflected, then a resonate cavity is created for the inelastic light.

The utilization of a Bragg-filtered, single-mode fiber as the source fiber 8450 can offer increased performance. By using an optical isolator on the delivery optical path, light re-entering the laser can be minimized.

The laser light may also be precluded from multiple transverse reflections end from back propagation into the laser by positioning an angled filter at the collection end of the cell (before or after the primary collection fiber filter). To accomplish this, the angled filter passes inelastic light and reflects laser light at an angle so that the laser light is diverted outside of the cell.

For simple operation in the analysis of weak inelastic light-matter interactions, a bundle of one or more, preferably filtered source fibers and one or more, preferably filtered collection fibers can be butted up to the waveguided tube which is filled with the sample.

An amorphous Teflon tubing is well suited for producing the waveguided cell since it exhibits a favorable refractive index in relation to water-based media. However, another technique is also useful. The liquid is spiked with substance which increases its refractive index. For example, the addition of sodium chloride to an aqueous-based solution raises the refractive index of the solution as the salt dissolves. In essence, the analytical medium is doped with a refractive-index-altering additive—similar to doping the glass which is used in optical fibers. If an additive is chosen which exhibits weak inelastic light-matter interactions, then the additive's response can be used as an analytical reference for comparison with inelastic responses from the analyte.

FIG. 85 illustrates an embodiment that is configured for usage without optical fibers. This configuration offers an advantage, compared to fiber-coupled devices in that there is no interference from signals generated by light interactions with the fiber materials. Since there are no fibers, the filtering requirements are simplified. The waveguiding tube 8574 is plugged with a filtered end piece 8580. The filter 8578 allows transmission of the laser light 8570 so that this light can enter the tube 8574 and interact with the investigative medium 8576. The filter 8578 rejects inelastic light 8572 and directs it for subsequent processing and analysis.

The opposite end of the waveguiding tube 8574 can have a light trap which reflects inelastic light and absorbs laser light. A suitable light trap is created by applying a filter 8584, which passes the laser light and reflects the wavelength shifted light, into a transparent plug 8586. The outer side of the plug 8586 is coated with a light-absorbing material 8582 such as a carbon film. Alternatively, the plug 8586 contains light-absorbing material which is preferably loaded to the outer end (so that the desired reflection is not inadvertently impeded).

The non-fiber coupled configuration is well suited to laboratory analysis in general and analysis of plasma blood chemistries in particular.

Laser beams are readily narrowed to small diameters. This attribute can be exploited for benefit in a non-fiber-coupled configuration of a waveguided cell for analysis of inelastic light-matter interactions. FIG. 86 depicts a cell which utilizes this attribute. The laser beam 8600 enters the expanded-beam, light acceptance/delivery pattern 8612 of the cell 8610. It is reflected by a mirror 8602 into the cell 8610. The light emerging from the cell 8610 (laser line and inelastic) is collimated with expanded beam optics 8606 and filtered. Preferably, the filter 8604 passes a portion of the wavelength-shifted light and reflects the laser light back into the cell 8610. A light trap for the laser line 8614 controls the extent to which the laser light resonates within the cell.

In a similar manner, the cell can be configured such that it has a high numerical aperture. As such, it is capable of accepting light beyond the angular limits of the expanded beam optics. Thus, the laser beam can be introduced into the cell along side of the expanded beam optics and at a slightly larger angle.

FIG. 87 depicts a schematic representation of a probe assembly 8700 that incorporates a waveguided cell for low-concentration analysis of chemicals in remote locations. The probe is particularly well suited to in situ analysis of environmental conditions such as in ground waters. The probe housing 8718 is streamlined to promote deployment in minimal space conditions and is readily hardened for cone penetrometer usage. The source and collection optical fibers 8710 interface 8712 with the waveguided cell 8714. The length of the cell tubing 8714 is chosen to facilitate response from the analytes in the sample. The tubing is coiled around a mandrel within the housing 8718. When positioned to the desired measurement location, the surrounding medium (such as ground water) is drawn through a particulate filter 8716 and into the cell 8714 for analysis.

The waveguided cells described herein, when energized with sufficiently intense laser light, can intensify the Raman response in a nonlinear fashion. This intensification is based on the stimulated Raman effect. As the intensity increases, the ratio of stimulated Raman light to spontaneous Raman light increases.

Related patent applications have described methods which yield side viewing and/or side delivery optical fibers and incorporation of the fibers in probes. The fibers are also well suited to producing probes which amplify the Raman response by surface enhancement ("SERS"). The surface-enhanced coating/treatment may be applied directly to one, or more, of the probe fiber side walls. Thus, the side wall of the probe's delivery fiber and/or the collection fiber is treated directly. In either case, the laser light in incident on this sensitized area and the desired response is collected by the collection fiber. As an alternative to treating fiber side walls, a film, plate, or similar material, is introduced into the probe. By placing the film between the fibers, the light is incident on one side of the film and collected on the other side. The film may also be positioned to the side of the delivery and collection fibers (as opposed to between them) such that the source fiber projects light onto and the collection fiber receives light off of a common region of the film. The configurations described above are suitable for indicators and fluorescence enhancers as well as surface enhanced Raman spectroscopy.

The side delivery/side collection fibers are also suited to creating a resonate cavity/semi-resonate cavity micro-probe. The cavity is created between parallel fibers such that Raman-scattered light and/or laser light bounces back and forth multiple times within the cavity. To form the cavity, the side walls of the fibers are flattened in the area between the fibers. Reflective filters are applied to the flat regions. Laser light may be introduced into the cavity through side delivery from one of the fibers. Inelastic light may be collected from the cavity through side collection by the other fiber. FIG. 88 depicts a probe in which only the inelastic light resonates within a cavity. Laser light 8836 is introduced into the cavity by a filtered fiber 8825, which excites the sample molecules within the cavity. Inelastic light resulting from the excitation bounces back and forth within the cavity between the mirror 8832 on the side wall of the "dead" fiber 8828 and the filter 8830 on the side wall of the collection fiber 8826. A fraction of the inelastic light passes through the filter 8830 and into the collection fiber 8826. The shaped surface 8834 of the collection fiber 8826 redirects the inelastic light for propagation to the detector. The filter 8830 serves the additional role of preventing the introduction of laser light into the collection fiber.

By employing methods described within the microscale filtering and manipulating fiber optic light micro-sized resonate cavities are readily created in numerous configurations in accordance with application requirements.

SUMMARY OF THE DETAILED DESCRIPTION

From the foregoing description, it will be appreciated that the present invention provides a method and apparatus for improved fiber optic light management. By applying various light management and manipulation techniques, one may construct a fiber optic probe assembly that is ideal for low light spectrographic analysis. In an exemplary system, the probe improves response to subtle light-matter interactions of high analytical importance and reduces sensitivity to otherwise dominant effects. This is accomplished by adjusting the illumination and collection fields of view in order to optimize the probe's sensitivity. Light manipulation is applied internal to the fiber so that the probe's delivery pattern and field of view do not require external manipulation and are not adversely affected by the investigated media. This allows the light delivery pattern or field of view or both to be aggressively steered off-axis to achieve significant increased performance levels. Aggressive beam steering is accomplished by employing internally reflective surfaces in the fiber. A reflective metal coating or low refractive index coatings or encapsulants can be used to ensure total internal reflection. The fibers also incorporate filters, cross-talk inhibitors and other features that provide a high performance probe in a robust package. Design variations provide side viewing, viewing through a common aperture, viewing along a common axis, and other features.

Various embodiments have been described herein. However, the illustrations and text are intended to teach various aspects of light manipulation that can be readily applied to various fiber optic applications. Permutations, derivatives, and combinations of these methodologies can be readily formed to solve numerous application-specific problems that have previously plagued both the fiber optic industry in general and photonic instrumentation practitioners. In order to present this teaching as effectively as possible, an exhaustive list of applications and variations is not presented. Additional variations and applications should be within the level of skill of those who are knowledgeable in this general subject area.

The present invention has been described in relation to particular embodiments which are intended in all respects to be illustrative rather than restrictive. Alternative embodiments will become apparent to those skilled in the art to which the present invention pertains without departing from its spirit and scope. Accordingly, the scope of the present invention is defined by the appended claims rather than the foregoing description.

What is claimed is:

1. A method for producing precision sleeves for the coupling of optical fibers, comprising the steps of:
    applying, by an electrolytic process, a first coating of material on a mandrel having a diameter suitable for producing a precision sleeve compatible with the ends of optical fibers to be coupled by the precision sleeve;
    depositing a second coating of material over the first coating of material to produce the precision sleeve;
    removing the mandrel; and
    removing the first coating.

2. The method of claim 1, wherein the mandrel comprises one of a buffered optical fiber, an un-buffered optical fiber, or a metal wire.

3. The method of claim 2, wherein the mandrel comprises the buffered optical fiber, and the step of removing the mandrel comprises heating the optical fiber until a fiber buffer degrades and removing the optical fiber when the fiber buffer degrades.

4. The method of claim 2, wherein the step of removing the mandrel comprises a chemical attack of the optical fiber.

5. The method of claim 1, wherein the first and second materials coated on the mandrel are metallic.

6. The method of claim 5, wherein at least a portion of the second coating of material is applied with electrolysis coating.

7. The method of claim 1, wherein the second material coated onto the mandrel comprises platinum.

8. The method of claim 1, further wherein the step of removing the first coating of material comprises the step of chemically machining the precision sleeve.

9. The method of claim 1, wherein the precision sleeve comprises a cylinder with a wall thickness of less than 0.0015 inches.

10. The method of claim 9, wherein the cylinder of the precision sleeve comprises at least partially a metallic material.

11. A method for producing a precision sleeve for coupling optical fibers, comprising the steps of:
    applying, by an electrolytic process, a first material coating on a mandrel having a diameter that is substantially similar to the diameter of the optical fibers, the mandrel held in place by a plate to accept the coating material;
    depositing a second coating of material over the first coating of material to form the precision sleeve;
    removing the mandrel from the coating materials to produce the precision sleeve; and
    machining the precision sleeve to obtain a diameter and finish compatible with the ends of optical fibers to be coupled by the precision sleeve.

12. The method of claim 11, wherein the mandrel comprises one of a buffered optical fiber, an un-buffered optical fiber, or a metal wire.

13. The method of claim 12, wherein the step of removing the mandrel comprises:
    heating the optical fiber serving as the mandrel until degradation of a fiber buffer of the optical fiber; and
    removing the optical fiber from the first and second coating materials in response to degradation of the fiber buffer.

14. The method of claim 12, wherein the step of removing the mandrel comprises applying chemical composition to the optical fiber serving as the mandrel to degrade a fiber buffer of the optical fiber; and
    removing the optical fiber from the first and second coating materials in response to degradation of the fiber buffer.

15. The method of claim 11, wherein the step of machining comprises removing the first coating of material and increasing the diameter of the second coating by applying a chemical composition.

16. The method of claim 15, wherein the chemical composition comprises an acid.

17. The method of claim 8, wherein the step of chemically machining comprises removing the first coating material and increasing the diameter of the second coating by applying a chemical composition.

18. A method for producing a precision sleeve for the coupling of optical fibers, comprising the steps of:
    electrolytically depositing a platinum-based metal on one of an un-buffered optical fiber and a metal wire forming a mandrel having a diameter suitable for producing the precision sleeve compatible with the ends of optical fibers to be coupled by the precision sleeve; and
    removing the mandrel.

19. The method of claim 18, wherein in the mandrel is an un-buffered optical fiber, the method further comprising the step of heating the un-buffered optical fiber to a temperature such that the un-buffered fiber melts from the platinum-based metal forming the precision sleeve.

20. The method of claim 18, wherein the mandrel is a wire, the method further comprising the step of eroding the wire away from the platinum-based metal forming the precision sleeve.

* * * * *